(12) United States Patent
Shaikh et al.

(10) Patent No.: US 11,098,026 B2
(45) Date of Patent: Aug. 24, 2021

(54) FUSED BICYCLIC COMPOUNDS, COMPOSITIONS AND APPLICATIONS THEREOF

(71) Applicant: IMPETIS BIOSCIENCES LIMITED, Mumbai (IN)

(72) Inventors: Nadim Shaikh, Mumbai (IN); Mahesh Thakkar, Mumbai (IN); Shailesh Shinde, Mumbai (IN); Manoj Joshi, Mumbai (IN); Keshav Naik, Mumbai (IN); Amit Bhalerao, Mumbai (IN); Mayur Mukim, Mumbai (IN); Debnath Bhuniya, Mumbai (IN); Bheemashankar Kulkarni, Mumbai (IN); Kasim Mookhtiar, Mumbai (IN)

(73) Assignee: IMPETIS BIOSCIENCES LIMITED, Mumbai (IN)

( * ) Notice: Subject to any disclaimer, the term of this patent is extended or adjusted under 35 U.S.C. 154(b) by 0 days.

(21) Appl. No.: 16/494,239

(22) PCT Filed: Mar. 13, 2018

(86) PCT No.: PCT/IN2018/050136
§ 371 (c)(1),
(2) Date: Sep. 13, 2019

(87) PCT Pub. No.: WO2018/167800
PCT Pub. Date: Sep. 20, 2018

(65) Prior Publication Data
US 2020/0087281 A1    Mar. 19, 2020

(30) Foreign Application Priority Data

Mar. 13, 2017   (IN) ............................. 201741008624

(51) Int. Cl.
| | | |
|---|---|---|
| *C07D 401/12* | (2006.01) |
| *C07D 209/04* | (2006.01) |
| *C07D 215/233* | (2006.01) |
| *C07D 217/02* | (2006.01) |
| *C07D 231/56* | (2006.01) |
| *C07D 237/30* | (2006.01) |
| *C07D 239/74* | (2006.01) |
| *C07D 265/36* | (2006.01) |
| *C07D 319/16* | (2006.01) |
| *C07D 405/04* | (2006.01) |
| *C07D 417/04* | (2006.01) |
| *C07D 471/04* | (2006.01) |
| *A61K 45/06* | (2006.01) |

(52) U.S. Cl.
CPC ......... *C07D 401/12* (2013.01); *C07D 209/04* (2013.01); *C07D 215/233* (2013.01); *C07D 217/02* (2013.01); *C07D 231/56* (2013.01); *C07D 237/30* (2013.01); *C07D 239/74* (2013.01); *C07D 265/36* (2013.01); *C07D 319/16* (2013.01); *C07D 405/04* (2013.01); *C07D 417/04* (2013.01); *C07D 471/04* (2013.01); *A61K 45/06* (2013.01)

(58) Field of Classification Search
CPC ..................................................... C07D 401/12
USPC ......................................................... 546/139
See application file for complete search history.

(56) References Cited

U.S. PATENT DOCUMENTS

2014/0163025 A1   6/2014   Eckhardt

FOREIGN PATENT DOCUMENTS

WO      WO 97/025321      7/1997

OTHER PUBLICATIONS

International Application Status Report, dated Sep. 4, 2019, in International Patent Application No. PCT/IN2018/050136.
International Search Report & Written Opinion, dated May 3, 2018, in International Patent Application No. PCT/IN2018/050136.
Bhuniya, D. et al., Discovery of a potent and selective small molecule hGPR91 antagonist, Bioorganic & Medicinal Chemistry Letters, vol. 21, pp. 3596-3602, 2011.
De Castro Fonseca, M., et al., GPR91: expanding the frontiers of Krebs cycle intermediates, Cell Communication and Signaling, 14:3, 9 pages, 2016.
Correa, P.R.A.V., et al., Succinate is a paracrine signal for liver damage, Journal of Hepatology, vol. 47, pp. 262-269, 2007.
Favret, S., et al., Deficiency in the metabolite receptor SUCNR1 (GPR91) leads to outer retinal lesions, Aging, vol. 5, No. 6, pp. 427-444, 2013.
Hakak, Y., et al., The role of the GPR91 ligand succinate in hematopoiesis, Journal of Leukocyte Biology, vol. 85, pp. 837-843, 2009.
He, W., et al., Citric acid cycle intermediates as ligands for orphan G-protein-coupled receptors, Nature, vol. 429, pp. 188-193, 2004.
Hu, J., et al., Inhibition of high glucose-induced VEGF release in retinal ganglion cells by RNA interference targeting G protein-coupled receptor 91, Experimental Eye Research, vol. 109, pp. 31-39, 2013.
Montez, P., et al., Angiotensin Receptor Blockade Recovers Hepatic UCP2 Expression and Aconitase and SDH Activities and Ameliorates Hepatic Oxidative Damage in Insulin Resistant Rats, Endocrinology, vol. 153, No. 12, pp. 5746-5759, 2012.

(Continued)

*Primary Examiner* — Taofiq A Solola
(74) *Attorney, Agent, or Firm* — Knobbe, Martens, Olson & Bear LLP

(57) ABSTRACT

Fused bicyclic compounds are inhibitors of GPR91. The compounds, their stereoisomers, tautomers, prodrugs, polymorphs, solvates, pharmaceutically acceptable salts, and pharmaceutical compositions containing them are useful in the treatment, prevention, prophylaxis, management, or adjunct treatment of all medical conditions related to inhibition of GPR91.

11 Claims, No Drawings

(56) References Cited

OTHER PUBLICATIONS

Rubic, T., et al., Triggering the succinate receptor GPR91 on dendritic cells enhances immunity, Nature Immunology, vol. 9, No. 11, pp. 1261-1269, 2008.

Sapieha, P., et al., The succinate receptor GPR19 in neurons has a major role in retinal angiogenesis, Nature Medicine, vol. 14, No. 10, pp. 1067-1076, 2008.

FUSED BICYCLIC COMPOUNDS, COMPOSITIONS AND APPLICATIONS THEREOF

PRIORITY AND CROSS REFERENCE TO RELATED APPLICATIONS

This application is the U.S. National Stage Application under 35 U.S.C. § 371 of International Application No. PCT/IN2018/050136, filed Mar. 13, 2018, designating the U.S. and published in English as WO 2018/167800 A1 on Sep. 20, 2018, which claims the benefit of Indian Patent Application No. IN 201741008624, filed Mar. 13, 2017. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD OF THE INVENTION

The present invention relates to fused bicyclic compounds that are inhibitors of GPR91 also known as SUCNR1, their stereoisomers, tautomers, prodrugs, polymorphs, solvates, pharmaceutically acceptable salts, and pharmaceutical compositions containing them. These compounds are useful in the treatment, prevention, prophylaxis, management, or adjunct treatment of all medical conditions related to inhibition of GPR91. The disclosure also relates to the process of preparation of the fused bicyclic compounds, and to pharmaceutical compositions containing them.

BACKGROUND OF THE INVENTION

G-protein coupled receptor, known as GPR91 is expressed in kidney, liver, heart, retinal cells and possibly many other tissues, leading to a wide array of physiological and pathological effects. Succiante, a citric acid cycle intermediate act as an extracellular signaling molecule that binds to and activates GPR91. GPR91 interacts with multiple G-proteins. According to some studies using pertussis toxin, GPR91 can couple either with $G_i$ or $G_q$, triggering different pathways and initiating distinct cellular effects. In HEK293 and MDCK (kidney derived cells), succinate induces intracellular calcium release, inositol triphosphate formation, extracellular-signal-regulated kinases 1/2 (ERK1/2) activation and decrease of cyclic adenosine monophosphate (cAMP) concentration, which are signaling pathways induced by $G_q$ or $G_i$ coupling, depending only on succinate concentration (He et al, Nature. 2004 May 13; 429(6988): 188-93). In hematopoietic progenitor cells, however, signaling mediated exclusively by $G_{i/o}$ leads to proliferation due to ERK1/2 activation. In cardiomyocytes, succinate increases rather than decreases cAMP, leading to protein kinase A (PKA) activation, and suggesting that GPR91 coupling to $G_s$ is also possible. These distinct intracellular signaling pathways initiated by GPR91 activation indicate that succinate actions as a hormone can indeed be very diverse. Moreover, after triggering the signal transduction cascade, GPR91 is known to undergo internalization. Imaging studies indicated that GPR91 is located specifically on the plasma membrane, and is internalized and then desensitized as a result of ligand stimulation (de Castro Fonseca M et al, Cell Commun Signal. 2016 Jan. 12; 14:3).

GPR91 has been described in many cell types, and demonstrated to have a vast array of functions in the human body. In kidney, GPR91 is localized to the proximal tubule, juxtaglomerular apparatus (JGA), distal tubule, glomerulus (likely glomerular endothelial cells) and to the apical membranes of multiple distal segments, including the thick ascending limb, the macula densa (MD), and the principal cells of the cortical and medullary collecting ducts. Succinate is accumulated in extra-cellular spaces under ischemia to act on GPR91 to increase blood pressure, a mechanism to increase local $O_2$ supply. Succinate (SA) treatment leads to increase in blood pressure via renin-dependent activation of RAS system and this effect is abolished in GPR91$^{-/-}$ mice and with angiotensin converting enzyme inhibitor indicating its role in the regulation of blood pressure (He et al, Nature, 2004).

Human iMoDCs have high expression of GPR91 transcripts and GPR91 expression is induced specifically during the differentiation from monocyte to iMoDC. Succinate induces migration of iMoDCs in U937 cells (U937 is a human macrophage-like cell line which had substantial expression of GPR91 mRNA). Succinate mediates the chemotaxis of human iMoDCs and stimulates the production of inflammatory cytokines. Triggering GPR91 on human iMoDCs with succinate enhances SEA- or tetanus toxoid-induced production of cytokines by human CD4$^+$ T cells in a dose-dependent way. GPR91 mediates the immunomodulatory effects of succinate as GPR91 deletion impairs DC migration and immunity. GPR91$^{-/-}$ skin grafts elicit weaker allograft rejection responses in vivo than corresponding wild-type grafts indicating its role in immune disorders. (Rubic T et al, Nat immunol. 9(11):1261-9. 2008).

GPR91 is expressed in hematopoietic progenitor cell (HPCs). GPR91 mRNA and protein expression were detected in human bone marrow CD34 progenitor cells, as well as in erythroid and megakaryocyte cultures and the erythroleukemic cell line TF-1. Succinate stimulates the proliferation of cultured megakaryocyte and erythroid progenitor cells. Succinate stimulates TF-1 cell proliferation through GPR91 and requires activation of the Erk MAPK pathway. In vivo administration of succinate enhances multilineage blood cell recovery and was found to elevate the levels of hemoglobin, platelets, and neutrophils in a mouse model of chemotherapy-induced myelosuppression. These results suggest that succinate GPR91 signaling is capable of promoting HPC development and its role in Hematopoiesis (Hakak Y et al, J Leukoc Biol. 2009 May; 85(5):837-43).

Succinate levels rise in the ischemic retina of rodents and through GPR91 receptor it mediates vessel growth in normal retinal development and proliferative ischemic retinopathy. GPR91 is expressed in retinal ganglion neurons, retinal pigment epithelium and microglia. Intravitreal succinate injection increased mRNA expression of the proangiogenic factors VEGF, angiopoietin-1 (Ang-1) and Ang-2, whereas antiangiogenic thrombospondin-1 was repressed. siRNA-mediated knockdown of GPR91 diminished GPR91 mRNA and protein expression and vascular densities and abolished the effects of succinate on the angiogenic factors. siRNA to GPR91 attenuated retinal neovascularization during the ischemic phase of oxygen induced retinopathy (Sapieha et al, Nat Med. 2008 October; 14 (10): 1067-76). GPR91 knockdown protects against retinal neovascularization in ischemic proliferative retinopathy (Favret et al, Aging, 2013 June; 5(6):427-44). Exposure to high glucose induces VEGF expression in the RGC-5 cells. GPR91 shRNA inhibits high glucose-induced VEGF release as well as proliferation/migration of RF/6A cells. GPR91 modulates VEGF release possibly by ERK1/2 and JNK MAPK signaling (Hu J et al, Exp Eye Res. 2013 April; 109:31-9). All these data suggest role of GPR91 in retinal angiogenesis.

GPR91 was found to be expressed in quiescent hepatic stellate cells, and its expression was decreased with activation. Succinate levels are increased ~14 fold higher during hepatic ischemia and exposure to succinate leads to activation of HSCs (Correa P R et al, Journal of Hepatology 47: 262-269 (2007). C57BL6/J mice fed the MCD diet had elevated succinate levels in their plasma, decreased SDH activity and increased GPR91 and α-SMA expression in isolated HSCs. HSCs cultured in MCD media showed significantly decreased SDH activity and increased succinate concentration and GPR91 and α-smooth muscle actin (α-SMA) expression. Cultured HSCs treated with succinate showed increased protein expression of GPR91 and α-SMA, markers of fibrogenic response. Transfection of siRNA against GPR91 abrogated succinate-induced increases in α-SMA expression (Montez et al, Endocrinology. 2012 December; 153(12): 5746-5759). All these data suggests role of GPR91 in liver disease like liver fibrosis, non alcoholic steatohepatitis.

GPR91 antagonists are useful as preservation solution or mechanical perfusion strategies for transplantation for various organs such as liver, kidney, heart. It can prolong preservation time; minimize allograft rejection or complications associated with transplantation. GPR91 antagonists can be administered to mammals including humans orally /iv/ip route, acute or chronic regimen to decrease allograft rejection or transplant complications.

Therefore, GPR91 antagonists could be useful for therapeutic intervention of multiple pathologic conditions like retinal neovascularization, age-related macular degeneration (AMD), wet macular degeneration (WMD), diabetic retinopathy, nonalcoholic steatohepatitis (NASH), liver fibrosis, Immune disorders, cancer, hypertension, blood pressure, as perfusion fluids for preservation of organs for transplant, decrease allograft rejection or transplant complications.

There remains a need to find new compounds that are inhibitors of GPR91 useful for the treatment of disease states mediated by GPR91.

SUMMARY OF INVENTION

The present disclosure discloses a compound of Formula I,

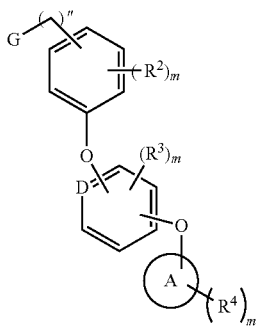

Formula (I)

their tautomers, polymorphs, stereoisomers, prodrugs, solvates, pharmaceutically acceptable salts thereof, wherein A is substituted or unsubstituted 5-10 membered bicyclic or polycyclic fully or partially unsaturated heterocyclic ring having 1-5 heteroatoms independently selected from O, N, or S; D is selected from $CR^1$ or N; G is selected from $-C(O)OR^1$, $-C(O)NR^aR^b$, $-SO_pR^1$, $-NR^1SO_2R^1$ or 5-7 membered monocyclic fully or partially unsaturated heterocyclic ring having 1-4 heteroatoms independently selected from O, N or S; $R^1$ is selected from hydrogen, $C_{1-6}$ haloalkyl, $C_{1-6}$ alkyl, $C_{6-10}$ aryl, $C_{5-10}$ heteroaryl, $C_{3-6}$ cycloalkyl or $C_{5-10}$ heterocyclyl, wherein $C_{6-10}$ aryl, $C_{3-6}$ cycloalkyl, $C_{5-10}$ heteroaryl, and $C_{5-10}$ heterocyclyl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{2-6}$ alkenyl, $C_{2-6}$ alkynyl, $C_{1-6}$ alkoxy, $C(O)R^1$, $R^1C(O)NR^aR^b$, $-OC(O)R^1$, $R^6$, $-(CR^aR^b)_mC(O)R^6$, $-(CR^aR^b)_mNR^7R^8$, $-NR^aC(O)-$, $-C_{1-6}$ alkoxy $C(O)NR^aR^b$, $-SO_2NR^aR^b-$, $-NR^aC(O)NR^aR^b$, $C_{1-6}$ alkoxyamino, azido, cyano, halogen, hydroxy, $C_{1-6}$ alkylhydroxy, $C_{1-6}$ haloalkyl, perhalo $C_{1-6}$ alkyl, $-C(S)R^a$, $-C(O)OR^1$, $C_{1-6}$ alkyl $C(O)OR^b$, $OC(O)$ $C_{1-6}$ alkyloxy, $OR_aC(O)OR_b$— $C_{1-6}$ alkylOC(O)OC$_{1-6}$ alkyloxy, $-SO_3H$, $-S(O)_pR^6$, $-S(O)_2NR^7R^8$ $C_{1-6}$ alkylthio or nitro; $R^6$ is selected from the group consisting of hydrogen, $-(CR^aR^b)_mOR^6$, halogen, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl, wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, $-C(O)OR^1$, $OR^5$, $-OC(O)R^6$, $-(CR^aR^b)_mC(O)NR^7R^8$, $-NR^6C(O)R^6$, $-SR^6$, $-S(O)_pR^6$, $-S(O)_2NR^7R^8$ or $-NR^6S(O)_2R^6$; $R^5$, $R^7$, and $R^8$ are independently selected from the group consisting of hydrogen, $-(CR^aR^b)_mOR^6$, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl, or $R^7$, and $R^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic saturated or partially unsaturated carbocyclyl or heterocyclyl ring is further optionally substituted with 1 to 4 substituents independently selected from halogen, $C_{1-6}$ alkyl, $C_{2-6}$ alkenyl, $C_{2-6}$ alkynyl, nitro, cyano, $-(CR^aR^b)_mOR^6$, $-SR^6$, $-(CR^aR^b)_mNR^7R^8$, oxo, $C_{1-6}$ alkylsulfonyl, $-(CR^aR^b)_mCOOR^6$, $-(CR^aR^b)_mC(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, $-OR^6$, halogen, $C_{1-6}$ haloalkyl, perhalo $C_{1-6}$ alkyl, $-SO_pR^1$, and $C_{1-6}$ alkyl; or $R^a$, and $R^b$ can be taken together to form a monocyclic or a bicyclic saturated or partially unsaturated carbocyclyl or heterocyclyl ring optionally having 1-5 heteroatoms selected from O, N, or S; m is 0 to 4; n is 0 to 3; p is 0-2.

The present disclosure further describes the process of preparation of compounds of Formula I or their polymorphs, stereoisomers, tautomers, prodrugs, solvates, and pharmaceutically acceptable salts thereof.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural Formulae given herein and throughout the present disclosure, the following terms have been indicated meaning, unless specifically stated otherwise.

Furthermore, the compound of Formula I can be its derivatives, analogs, stereoisomer's, diastereomers, geometrical isomers, polymorphs, solvates, co-crystals, intermediates, metabolites, prodrugs or pharmaceutically acceptable salts and compositions.

The compounds of Formula I and their polymorphs, stereoisomers, prodrugs, solvates, co-crystals, intermediates, pharmaceutically acceptable salts, and metabolites thereof can also be referred as "compounds of the present disclosure".

The compounds according to Formula I may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in Formula I or in any chemical structure illustrated herein, is not specified, the structure is intended to encompass any stereoisomer and all mixtures thereof. Thus, compounds according to Formula I containing one or more chiral centres may be used as racemic modifications including racemic mixtures and racemates, enantiomerically-enriched mixtures, or as enantiomerically-pure individual stereoisomers.

Individual stereoisomers of a compound according to Formula I which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form.

Alternatively, specific stereoisomers may be synthesized by asymmetric synthesis using optically active reagents, substrates, catalysts or solvents, or by converting one enantiomer to the other by asymmetric transformation.

It is to be understood that the references herein to compounds of Formula I and salts thereof covers the compounds of Formula I as free bases, or as salts thereof, for example as pharmaceutically acceptable salts thereof. Thus, in one embodiment, the invention is directed to compounds of Formula I as the free base. In another embodiment, the invention is directed to compounds of Formula I and salts thereof. In a further embodiment, the invention is directed to compounds of Formula I and pharmaceutically acceptable salts thereof.

It will be appreciated that pharmaceutically acceptable salts of the compounds according to Formula I may be prepared. Indeed, in certain embodiments of the invention, pharmaceutically acceptable salts of the compounds according to Formula I may be preferred over the respective free base because such salts impart greater stability or solubility to the molecule thereby facilitating Formulation into a dosage form. Accordingly, the invention is further directed to compounds of Formula I, and pharmaceutically acceptable salts thereof.

Included within the scope of the "compounds of the invention" are all solvates (including hydrates), complexes, polymorphs, prodrugs, radiolabelled derivatives, and stereoisomers of the compounds of Formula I, and salts thereof.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, isopropyl alcohol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The compounds of the present disclosure may have the ability to crystallize in more than one form, a characteristic known as polymorphism, and all such polymorphic forms ("polymorphs") are encompassed within the scope of the present disclosure.

The term "substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group. The term "optionally substituted" as used herein means that the group in question is either unsubstituted or substituted with one or more of the substituents specified. When the group in question is substituted with more than one substituent, the substituent may be same or different.

The term "prodrugs" refers to the precursor of the compound of Formula Ia, and Formula I which on administration undergoes chemical conversion by metabolic processes before becoming active pharmacological substances. In general, such prodrugs will be functional derivatives of a compound of the invention, which are readily convertible in vivo into a compound of the invention.

The term "alkyl" refers to a saturated hydrocarbon chain having the specified number of carbon atoms. For example, which are not limited, $C_{1-6}$ alkyl refers to an alkyl group having from 1-6 carbon atoms, or 1-4 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, isobutyl, and t-butyl.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1] heptene, and the like.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH$_2$C≡CH), homopropargyl (or but-1-yn-4-yl, —CH$_2$CH$_2$C≡CH) and the like.

The term "cycloalkyl" refers to unless otherwise mentioned, carbocyclic groups of from 3 to 6 carbon atoms having a single cyclic ring or multiple condensed rings or spirocyclic rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cycloheptyl, cyclohetynyl, cyclooctyl, and the like.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to an alkyl group attached via an oxygen linkage to the rest of the molecule, i.e., refers to the group R'''—O—, where R''' is optionally substituted alkyl or optionally substituted cycloalkyl, or optionally substituted alkenyl or optionally substituted alkynyl, wherein alkyl, alkenyl, alkynyl, and cycloalkyl are as defined herein. For example, $C_{1-6}$ alkoxy refers to an alkyl group having from 1-6 carbon atoms, or 1-4 carbon atoms attached via an oxygen linkage to the rest of the molecule. Preferred alkoxy groups include, without limitation, —OCH$_3$ (methoxy), —OC$_2$H$_5$ (ethoxy) and the like.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

The term "haloalkoxy" refers to an alkoxy group as defined above further attached via halo linkage. For example, $C_{1-6}$ haloalkoxy refers to an alkoxy group having from 1-6 carbon atoms, or 1-3 carbon atoms further attached via halo linkage. Preferred haloalkoxy groups include, without limitation, —OCH$_2$Cl, —OCHCl$_2$, and the like.

The term "aryl" refers to aromatic ring having a specified number of carbon atoms. For example, $C_{6-10}$ aryl refers to an aryl group having 6-10 member atoms, or 6 member atoms. $C_{6-10}$ aryl refers to an aryl group having 6 to 10 member atoms Preferred aryl groups include, without limitation, phenyl, and the like.

The term "heteroaryl" refers to aromatic rings containing from 1 to 4 heteroatoms in the ring. "Heteroaryl" groups may be substituted with one or one or more substituents if so defined herein. The "$C_{1-6}$ heteroaryl" rings having 1 or 6 carbon as member atoms. The term "5-10 membered heteroaryl" has 5 to 10 carbon as member atoms. The "heteroaryl" includes pyridinyl, tetrazolyl and pyrazolyl. "Heteroatom" refers to a nitrogen, sulfur, or oxygen atom, for example a nitrogen atom or an oxygen atom. Such heteroaryl groups can have a single ring (e.g. pyridinyl or furanyl) or multiple condensed rings (e.g. indolizinyl, benzooxazolyl, benzothiazolyl, or benzothienyl). Examples of heteroaryls include, but are not limited to, [1,2,4] oxadiazole, [1,3,4] oxadiazole, [1,2,4] thiadiazole, [1,3,4] thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heterocyclic" refer to saturated or unsaturated monocyclic aliphatic rings containing 5-10 ring members including 1 or 2 heteroatoms or to saturated or unsaturated bicyclic aliphatic rings containing 5, 6 or 7 ring members including 1 or 2 heteroatoms. In certain embodiments, "heterocyclic" groups are saturated. In other embodiments, "heterocyclic" groups are unsaturated. "heterocyclic" groups containing more than one heteroatom may contain different heteroatoms. "heterocyclic" groups may be substituted with one or more substituents as defined herein. "heterocyclic" includes piperidinyl, tetrahydropyranyl, azepinyl, oxazepinyl, azabicyclo[3.1.0]hexanyl.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring.

The term "heterocyclyl" refers to a saturated or partially unsaturated group having a single ring or multiple condensed rings or spirocyclic rings, unless otherwise mentioned, having from 1 to 10 carbon atoms having 1 to 5 hetero atoms, preferably 1, 2, 3, 4, or 5 heteroatoms, selected from nitrogen, sulphur, and/or oxygen within the ring. Heterocyclic groups can have a single ring or multiple condensed rings, and include dihydrofuranyl, tetrahydrofuranyl, morpholinyl, pyrrolidinyl, dihydropyrrole, dihydropyranyl, tetrahydropyranyl, pyrazolidinyl, imidazolidinyl, dihydropyridinyl, tetrahydropyridinyl, piperidinyl, dihydropyrazinyl, tetrahydropyrazinyl, piperazinyl, dihydropyridinyl, benzodioxolyl, tetrahydroquinolinyl, tetrahydroisoquinolinyl, tetrahydronaphthyridinyl, tetrahydrothienopyridinyl, 7-azaspiro[3,5]nonan-2-yl, 2,7-diazaspiro[3,5]nonan-2-yl, 9-azaspiro[5.5]undecan-4-yl, and the like.

The term "carbocyclyl" refers to a saturated or partially unsaturated group having a single ring or multiple condensed rings or spirocyclic rings, unless otherwise mentioned, having from 1 to 10 carbon atoms. Preferably cyclopropyl, cyclobutyl, cyclopentyl, cyclopentenyl, cyclohexyl, cyclohexenyl, cycloheptyl, cyclohetynyl, cyclooctyl, and the like, The term "thiol" refers to the group —SH.

The term "substituted alkylthio" refers to the group —S-substituted alkyl.

The phrase "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid.

Salts and solvates having non-pharmaceutically acceptable counter-ions or associated solvents are within the scope of the present invention, for example, for use as intermediates in the preparation of other compounds of Formula I, and their pharmaceutically acceptable salts. Thus, one embodiment of the invention embraces compounds of Formula I, and salts thereof. Compounds according to and Formula I contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenyl acetate, propionate, butyrate, iso-butyrate, valerate, maleate, hydroxymaleate, acrylate, fumarate, malate, tartrate, citrate, salicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), aminobenzenesulfonate, p-toluenesulfonate (tosylate), and naphthalene-2-sulfonate.

A term once described, the same meaning applies for it, throughout the disclosure.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the present disclosure are congeners, analogs, hydrolysis products, metabolites and precursor or prodrugs of the compound. In general, unless otherwise indicated, all physical forms are equivalent for the uses contemplated herein and are intended to be within the scope of the present invention.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the present disclosure are quaternary ammonium compounds wherein an equivalent of an anion (M–) is associated with the positive charge of the N atom. M– may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M– is preferably an anion selected from chloride, bromide, iodide, sulphate, nitrate, acetate, maleate, oxalate, succinate or trifluoroacetate. More preferably M– is chloride, bromide, trifluoroacetate or methanesulphonate.

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present disclosure are inert organic solvents. The term "q.s." means adding a quantity sufficient to achieve a stated function, e.g., to bring a solution to the desired volume (i.e., 100%).

Wherever desired or necessary, in any of the above mentioned processes, any of the compounds of Formula (I) is converted into a pharmaceutically acceptable salt or vice versa or converting one salt form into another pharmaceutically acceptable salt form.

In an aspect of the present disclosure, pharmaceutical compositions are provided comprising a compound of the invention, and a pharmaceutical carrier, excipient or diluent. The pharmaceutical composition can comprise one or more of the compounds described herein. In a further embodiment, the pharmaceutical compositions of the invention can comprise a compound in combination with one or more other compounds and/or compositions having a like therapeutic effect.

In another aspect of the present disclosure, methods are provided for treatment, prevention, prophylaxis, management, or adjunct treatment in a mammal, of all medical conditions related to modulation of GPR91 such as retinal neovascularization, age-related macular degeneration (AMD), wet macular degeneration (WMD), diabetic retinopathy, nonalcoholic steatohepatitis (NASH), liver fibrosis, Immune disorders, cancer, hypertension, blood pressure, as perfusion fluids for preservation of organs for transplant, decrease allograft rejection or transplant complications.

In yet another aspect of the present disclosure, methods are provided for treatment, prevention, prophylaxis, management, or adjunct treatment of retinal neovascularization, age-related macular degeneration (AMD), wet macular degeneration (WMD), diabetic retinopathy, nonalcoholic steatohepatitis (NASH), liver fibrosis, Immune disorders, cancer, hypertension, blood pressure, as perfusion fluids for preservation of organs for transplant, decrease allograft rejection or transplant complications.

In another aspect of the present disclosure, the compounds of Formula I described herein and their pharmaceutically acceptable compositions either alone or in combination with other therapeutic agents are useful in methods for treating or lessening the severity of retinal neovascularization, age-related macular degeneration (AMD), wet macular degeneration (WMD), diabetic retinopathy, nonalcoholic steatohepatitis (NASH), liver fibrosis, Immune disorders, cancer, hypertension, blood pressure, as perfusion fluids for preservation of organs for transplant, decrease allograft rejection or transplant complications.

In addition to the methods of treatment set forth above, the present invention extends to the use of any of the compounds of the invention for the preparation of medicaments that may be administered for such treatments, as well as to such compounds for the treatments disclosed and specified.

A still further object of the invention is to provide a method for the treatment of the disease states recited above, by the administration of a therapeutically effective amount of the compounds of the invention, and/or the pharmaceutical compositions of the invention.

A yet further object of the invention is to provide Formulations for the treatment of the diseases as aforesaid, by the combination of at least one of the compounds of the invention, a pharmaceutical composition of the invention, combinations thereof with other compounds and compositions having a like therapeutic effect.

In an embodiment of the present disclosure, there is provided a compound of Formula I,

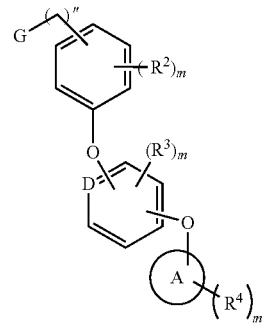

Formula (I)

their tautomers, polymorphs, stereoisomers, prodrugs, solvates, pharmaceutically acceptable salts thereof, wherein A is substituted or unsubstituted 5-10 membered bicyclic or polycyclic fully or partially unsaturated heterocyclic ring having 1-5 heteroatoms independently selected from O, N, or S; D is selected from $CR^1$ or N; G is selected from —C(O)$OR^1$, —C(O)$NR^aR^b$, —$SO_pR^1$, —$NR^1SO_2R^1$ or 5-7 membered monocyclic fully or partially unsaturated heterocyclic ring having 1-4 heteroatoms independently selected from O, N or S; $R^1$ is selected from hydrogen, $C_{1-6}$ haloalkyl, $C_{1-6}$ alkyl, $C_{6-10}$ aryl, $C_{5-10}$ heteroaryl, $C_{3-6}$ cycloalkyl or $C_{5-10}$ heterocyclyl, wherein $C_{6-10}$ aryl, $C_{3-6}$ cycloalkyl, $C_{5-10}$ heteroaryl, and $C_{5-10}$ heterocyclyl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{2-6}$ alkenyl, $C_{2-6}$ alkynyl, $C_{1-6}$ alkoxy, C(O)$R^1$, $R^1$C(O)$NR^aR^b$, —OC(O)$R^1$, $R^6$, —(C$R^aR^b$)$_m$C(O)$R^6$, —(C$R^aR^b$)$_m$$NR^7R^8$, —$NR^a$C(O)—, —$C_{1-6}$ alkoxy C(O)$NR^aR^b$, —$SO_2NR^aR^b$—, —$NR^a$C(O)$NR^aR^b$, $C_{1-6}$ alkoxyamino, azido, cyano, halogen, hydroxy, $C_{1-6}$ alkylhydroxy, $C_{1-6}$ haloalkyl, perhalo $C_{1-6}$ alkyl, —C(S)$R^a$, —C(O)$OR^1$, $C_{1-6}$ alkyl C(O)$OR^b$, OC(O) $C_{1-6}$ alkyloxy, O$R_a$C(O)$OR_b$— $C_{1-6}$ alkylOC(O)$OC_{1-6}$ alkyloxy, —$SO_3H$, —S(O)$_pR^6$, —S(O)$_2$$NR^7R^8$ $C_{1-6}$ alkylthio or nitro; $R^6$ is selected from the group consisting of hydrogen, —(C$R^aR^b$)$_m$$OR^6$, halogen, $C_{1-6}$ haloalkyl, —(C$R^aR^b$)$_m$C(O)$R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl, wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$; R$^5$, R$^7$, and R$^8$ are independently selected from the group consisting of hydrogen, —(CR$^a$R$^b$)$_m$OR$^6$, $C_{1-6}$ haloalkyl, —(CR$^a$R$^b$)$_m$C(O)R$^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl, or R$^7$, and R$^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic saturated or partially unsaturated carbocyclyl or heterocyclyl ring is further optionally substituted with 1 to 4 substituents independently selected from halogen, $C_{1-6}$ alkyl, $C_{2-6}$ alkenyl, $C_{2-6}$ alkynyl, nitro, cyano, —(CR$^a$R$^b$)$_m$OR$^6$, —SR$^6$, —(CR$^a$R$^b$)$_m$NR$^7$R$^8$, oxo, $C_{1-6}$ alkylsulfonyl, —(CR$^a$R$^b$)$_m$COOR$^6$, —(CR$^a$R$^b$)$_m$C(O)NR$^7$R$^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; R$^a$, and R$^b$ are independently selected from the group consisting of hydrogen, —OR$^6$, halogen, $C_{1-6}$ haloalkyl, perhalo $C_{1-6}$ alkyl, —SO$_p$R$^1$, and $C_{1-6}$ alkyl; or R$^a$, and R$^b$ can be taken together to form a monocyclic or a bicyclic saturated or partially unsaturated carbocyclyl or heterocyclyl ring optionally having 1-5 heteroatoms selected from O, N, or S; m is 0 to 4; n is 0 to 3; p is 0-2.

In an embodiment of the present disclosure, there is provided a compound of Formula I,

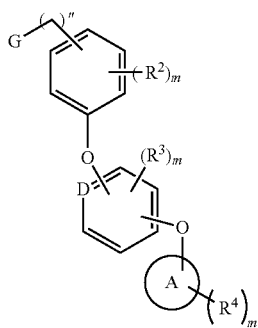

Formula (I)

their tautomers, polymorphs, stereoisomers, prodrugs, solvates, pharmaceutically acceptable salts thereof, wherein A is substituted or unsubstituted 5-10 membered bicyclic or polycyclic fully or partially unsaturated heterocyclic ring having 1-5 heteroatoms independently selected from O, N, or S; D is selected from CR$^1$ or N; G is selected from —C(O)OR$^1$, —C(O)NR$^a$R$^b$, —SO$_p$R$^1$, —NR$^1$SO$_2$R$^1$ or 5-6 membered monocyclic fully or partially unsaturated heterocyclic ring having 1-4 heteroatoms independently selected from O, N or S; R$^1$ is selected from hydrogen, $C_{1-6}$ haloalkyl, $C_{1-6}$ alkyl, $C_{6-10}$ aryl, $C_{5-10}$ heteroaryl, $C_{3-6}$ cycloalkyl or $C_{5-10}$ heterocyclyl, wherein $C_{6-10}$ aryl, $C_{3-6}$ cycloalkyl, $C_{5-10}$ heteroaryl, and $C_{5-10}$ heterocyclyl are optionally substituted with $C_{1-6}$ alkyl; R$^2$, R$^3$, and R$^4$ are independently selected from hydrogen, $C_{1-6}$ alkyl, $C_{3-6}$ cycloalkyl, $C_{2-6}$ alkenyl, $C_{2-6}$ alkynyl, $C_{1-6}$ alkoxy, C(O)R$^1$, R$^1$C(O)NR$^a$R$^b$, —OC(O)R$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —SO$_2$NR$^a$R$^b$—, —NR$^a$C(O)NR$^a$R$^b$, $C_{1-6}$ alkoxyamino, azido, cyano, halogen, hydroxy, $C_{1-6}$ alkylhydroxy, $C_{1-6}$ haloalkyl, perhalo $C_{1-6}$ alkyl, —C(S)R$^a$, —C(O)OR$^1$, $C_{1-6}$ alkyl C(O)OR$^b$, OC(O) $C_{1-6}$ alkyloxy, OR$_a$C(O)R$_b$—$C_{1-6}$ alkylOC(O)OC$_{1-6}$ alkyloxy, —SO$_3$H, —S(O)$_p$R$^6$, —S(O)$_2$NR$^7$R$^8$ $C_{1-6}$ alkylthio or nitro; R$^6$ is selected from the group consisting of hydrogen, —(CR$^a$R$^b$)$_m$OR$^6$, halogen, $C_{1-6}$ haloalkyl, —(CR$^a$R$^b$)$_m$C(O)R$^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl, wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$; R$^5$, R$^7$, and R$^8$ are independently selected from the group consisting of hydrogen, —(CR$^a$R$^b$)$_m$OR$^6$, $C_{1-6}$ haloalkyl, —(CR$^a$R$^b$)$_m$C(O)R$^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl, or R$^7$, and R$^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic saturated or partially unsaturated carbocyclyl or heterocyclyl ring is further optionally substituted with 1 to 4 substituents independently selected from halogen, $C_{1-6}$ alkyl, $C_{2-6}$ alkenyl, $C_{2-6}$ alkynyl, nitro, cyano, —(CR$^a$R$^b$)$_m$OR$^6$, —SR$^6$, —(CR$^a$R$^b$)$_m$NR$^7$R$^8$, oxo, $C_{1-6}$ alkylsulfonyl, —(CR$^a$R$^b$)$_m$COOR$^6$, —(CR$^a$R$^b$)$_m$C(O)NR$^7$R$^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; R$^a$, and R$^b$ are independently selected from the group consisting of hydrogen, —OR$^6$, halogen, $C_{1-6}$ haloalkyl, perhalo $C_{1-6}$ alkyl, —SO$_p$R$^1$, and $C_{1-6}$ alkyl; or R$^a$, and R$^b$ can be taken together to form a monocyclic or a bicyclic saturated or partially unsaturated carbocyclyl or heterocyclyl ring optionally having 1-5 heteroatoms selected from O, N, or S; m is 0 to 4; n is 0 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic fully or partially unsaturated heterocyclic ring having 1-5 heteroatoms independently selected from O, N, or S; D is selected from CR$^1$, or N; G is selected from —C(O)OR$^1$, —C(O)NR$^a$R$^b$, —NR$^1$SO$_2$R$^1$ or 5 membered monocyclic fully or partially unsaturated heterocyclic ring having 1-4 heteroatoms independently selected from O, N, or S; R$^1$ is selected from hydrogen, $C_{1-6}$ haloalkyl, $C_{1-6}$ alkyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{3-6}$ cycloalkyl, $C_{5-10}$ heteroaryl, and $C_{5-10}$ heterocyclyl are optionally substituted with $C_{1-6}$ alkyl; R$^2$, R$^3$, and R$^4$ are independently selected from hydrogen, $C_{1-6}$ alkyl, $C_{3-6}$ cycloalkyl, $C_{2-6}$ alkenyl, $C_{2-6}$ alkynyl, $C_{1-6}$ alkoxy, C(O)R$^1$, R$^1$C(O)NR$^a$R$^b$, —OC (O)R$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —SO$_2$NR$^a$R$^b$—, —NR$^a$C(O)NR$^a$R$^b$, NR$^a$OH, C$_{1-6}$ alkoxyamino, azido, cyano, halogen, hydroxy, C$_{1-6}$ alkylhydroxy, C$_{1-6}$ haloalkyl, perhalo C$_{1-6}$ alkyl, —C(S)R$^a$, C(O)OR$^1$, C$_{1-6}$ alkyl C(O)OR$^b$, OC(O) C$_{1-6}$ alkyloxy, OR$_a$C(O)OR$_b$— C$_{1-6}$ alkylOC(O)OC$_{1-6}$ alkyloxy, —SO$_3$H, —S(O)$_p$R$^6$, —S(O)$_2$NR$^7$R$^8$ C$_{1-6}$ alkylthio or nitro; R$^6$ is selected from the group consisting of hydrogen, —(CR$^a$R$^b$)$_m$OR$^6$, halogen, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, or C$_{5-10}$ heterocyclyl, wherein C$_{6-10}$ aryl, C$_{5-10}$ heteroaryl, C$_{3-6}$ cycloalkyl, C$_{5-10}$ heterocyclyl are optionally substituted with C$_{1-6}$ alkyl, wherein C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, and C$_{5-10}$ heterocyclyl are optionally substituted with one or more substituents selected from hydroxy, C$_{1-6}$ alkyl, C$_{1-6}$ alkoxy, C$_{1-6}$ alkoxyalkyl, halogen, C$_{1-6}$ haloalkyl, perhalo-C$_{1-6}$ alkyl, cyano, -cyano C$_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$, or —NR$^6$S(O)$_2$R$^6$; R$^5$, R$^7$, and R$^8$ are independently selected from the group consisting of hydrogen, —(CR$^a$R$^b$)$_m$OR$^6$, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, C$_{5-10}$ heterocyclyl, wherein, C$_{6-10}$ aryl, C$_{5-10}$ heteroaryl, C$_{3-6}$ cycloalkyl, and C$_{5-10}$ heterocyclyl are optionally substituted with C$_{1-6}$ alkyl or R$^5$, R$^7$ and R$^8$ can be taken together to form a monocyclic or a bicyclic saturated or partially unsaturated carbocyclyl or heterocyclyl ring optionally having 1-5 heteroatoms selected from O, N, S, wherein the monocyclic or a bicyclic ring carbocyclyl or heterocyclyl is further optionally substituted with 1 to 4 substituents independently selected from halogen, C$_{1-6}$ alkyl, C$_{2-6}$ alkenyl, C$_{2-6}$ alkynyl, nitro, cyano, —(CR$^a$R$^b$)$_m$OR$^6$, —SR$^6$, —(CR$^a$R$^b$)$_m$NR$^7$R$^8$, oxo, C$_{1-6}$ alkylsulfonyl, —(CR$^a$R$^b$)$_m$COOR$^6$, —(CR$^a$R$^b$)$_m$C(O)NR$^7$R$^8$, C$_{3-6}$ cycloalkyl, C$_{6-10}$ aryl, C$_{5-10}$ heterocyclyl, or C$_{5-10}$ heteroaryl, wherein C$_{3-6}$ cycloalkyl, C$_{6-10}$ aryl, C$_{5-10}$ heterocyclyl, and C$_{5-10}$ heteroaryl are optionally substituted with C$_{1-6}$ alkyl; R$^a$, and R$^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl; or R$^a$, and R$^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic fully or partially unsaturated heterocyclic ring having 1-5 heteroatoms independently selected from O, N, or S; D is selected from CR$^1$, or N; G is selected from —C(O)OR$^1$, —C(O)NR$^a$R$^b$, —NR$^1$SO$_2$R$^1$ or 5 membered monocyclic fully or partially unsaturated heterocyclic ring having 1-4 heteroatoms independently selected from O, N, or S; R$^1$ is selected from hydrogen, C$_{1-6}$ haloalkyl, C$_{1-6}$ alkyl, C$_{6-10}$ aryl, C$_{5-10}$ heteroaryl, or C$_{3-6}$ cycloalkyl, wherein C$_{6-10}$ aryl, C$_{3-6}$ cycloalkyl, and C$_{5-10}$ heteroaryl, are optionally substituted with C$_{1-6}$ alkyl; R$^2$, R$^3$, and R$^4$ are independently selected from hydrogen, C$_{1-6}$ alkyl, C$_{3-6}$ cycloalkyl, C$_{2-6}$ alkenyl, C$_{2-6}$ alkynyl, C$_{1-6}$ alkoxy, C(O)R$^1$, R$^1$C(O)NR$^a$R$^b$, —OC(O)R$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —SO$_2$NR$^a$R$^b$—, —NR$^a$C(O)NR$^a$R$^b$, NR$^a$OH, C$_{1-6}$ alkoxyamino, azido, cyano, halogen, hydroxy, C$_{1-6}$ alkylhydroxy, C$_{1-6}$ haloalkyl, perhalo C$_{1-6}$ alkyl, —C(S)R$^a$, C(O)OR$^1$, C$_{1-6}$ alkyl C(O)OR$^b$, OC(O) C$_{1-6}$ alkyloxy, OR$_a$C(O)OR$_b$—C$_{1-6}$ alkylOC(O)OC$_{1-6}$ alkyloxy, —SO$_3$H, —S(O)$_p$R$^6$, —S(O)$_2$NR$^7$R$^8$ C$_{1-6}$ alkylthio or nitro; R$^6$ is selected from the group consisting of hydrogen, —(CR$^a$R$^b$)$_m$OR$^6$, halogen, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, or C$_{5-10}$ heterocyclyl, wherein C$_{6-10}$ aryl, C$_{5-10}$ heteroaryl, C$_{3-6}$ cycloalkyl, C$_{5-10}$ heterocyclyl are optionally substituted with C$_{1-6}$ alkyl, wherein C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, and C$_{5-10}$ heterocyclyl are optionally substituted with one or more substituents selected from hydroxy, C$_{1-6}$ alkyl, C$_{1-6}$ alkoxy, C$_{1-6}$ alkoxyalkyl, halogen, C$_{1-6}$ haloalkyl, perhalo-C$_{1-6}$ alkyl, cyano, -cyano C$_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$, or —NR$^6$S(O)$_2$R$^6$; R$^5$, R$^7$, and R$^8$ are independently selected from the group consisting of hydrogen, —(CR$^a$R$^b$)$_m$OR$^6$, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, C$_{5-10}$ heterocyclyl, wherein, C$_{6-10}$ aryl, C$_{5-10}$ heteroaryl, C$_{3-6}$ cycloalkyl, and C$_{5-10}$ heterocyclyl are optionally substituted with C$_{1-6}$ alkyl or R$^5$, R$^7$ and R$^8$ can be taken together to form a monocyclic or a bicyclic saturated or partially unsaturated carbocyclyl or heterocyclyl ring optionally having 1-5 heteroatoms selected from O, N, S, wherein the monocyclic or a bicyclic ring carbocyclyl or heterocyclyl is further optionally substituted with 1 to 4 substituents independently selected from halogen, C$_{1-6}$ alkyl, C$_{2-6}$ alkenyl, C$_{2-6}$ alkynyl, nitro, cyano, —(CR$^a$R$^b$)$_m$OR$^6$, —SR$^6$, —(CR$^a$R$^b$)$_m$NR$^7$R$^8$, oxo, C$_{1-6}$ alkylsulfonyl, —(CR$^a$R$^b$)$_m$COOR$^6$, —(CR$^a$R$^b$)$_m$C(O)NR$^7$R$^8$, C$_{3-6}$ cycloalkyl, C$_{6-10}$ aryl, C$_{5-10}$ heterocyclyl, or C$_{5-10}$ heteroaryl, wherein C$_{3-6}$ cycloalkyl, C$_{6-10}$ aryl, C$_{5-10}$ heterocyclyl, and C$_{5-10}$ heteroaryl are optionally substituted with C$_{1-6}$ alkyl; R$^a$, and R$^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl; or R$^a$, and R$^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic fully or partially unsaturated heterocyclic ring having 1-5 heteroatoms independently selected from O, N, or S; D is selected from CR$^1$, or N; G is selected from —C(O)OR$^1$, —C(O)NR$^a$R$^b$, —NR$^1$SO$_2$R$^1$ or 5 membered monocyclic fully or partially unsaturated heterocyclic ring having 1-4 heteroatoms independently selected from O, N, or S; R$^1$ is selected from hydrogen, C$_{1-6}$ haloalkyl, C$_{1-6}$ alkyl, C$_{5-10}$ heteroaryl, C$_{3-6}$ cycloalkyl, or C$_{5-10}$ heterocyclyl, wherein C$_{3-6}$ cycloalkyl, C$_{5-10}$ heteroaryl, and C$_{5-10}$ heterocyclyl are optionally substituted with C$_{1-6}$ alkyl; R$^2$, R$^3$, and R$^4$ are independently selected from hydrogen, C$_{1-6}$ alkyl, C$_{3-6}$ cycloalkyl, C$_{2-6}$ alkenyl, C$_{2-6}$ alkynyl, C$_{1-6}$ alkoxy, C(O)R$^1$, R$^1$C(O)NR$^a$R$^b$, —OC(O)R$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —SO$_2$NR$^a$R$^b$—, —NR$^a$C(O)NR$^a$R$^b$, NR$^a$OH, C$_{1-6}$ alkoxyamino, azido, cyano, halogen, hydroxy, C$_{1-6}$ alkylhydroxy, C$_{1-6}$ haloalkyl, perhalo C$_{1-6}$ alkyl, —C(S)R$^a$, C(O)OR$^1$, C$_{1-6}$ alkyl C(O)OR$^b$, OC(O) C$_{1-6}$ alkyloxy, OR$_a$C(O)OR$_b$— C$_{1-6}$ alkylOC(O)OC$_{1-6}$ alkyloxy, —SO$_3$H, —S(O)$_p$R$^6$, —S(O)$_2$NR$^7$R$^8$ C$_{1-6}$ alkylthio or nitro; $R^6$ is selected from the group consisting of hydrogen, $-(CR^aR^b)_mOR^6$, halogen, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl, wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, $-C(O)OR^1$, $OR^5$, $-OC(O)R^6$, $-(CR^aR^b)_mC(O)NR^7R^8$, $-NR^6C(O)R^6$, $-SR^6$, $-S(O)_pR^6$, $-S(O)_2NR^7R^8$, or $-NR^6S(O)_2R^6$; $R^5$, $R^7$, and $R^8$ are independently selected from the group consisting of hydrogen, $-(CR^aR^b)_m OR^6$, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or $R^5$, $R^7$ and $R^8$ can be taken together to form a monocyclic or a bicyclic saturated or partially unsaturated carbocyclyl or heterocyclyl ring optionally having 1-5 heteroatoms selected from O, N, S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, $-(CR^aR^b)_m OR^6$, $-SR^6$, $(CR^aR^b)_mNR^7R^8$, oxo, $C_{1-6}$ alkylsulfonyl, $-(CR^aR^b)_mCOOR^6$, $-(CR^aR^b)_mC(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, $-OR^6$, halogen, $C_{1-6}$ haloalkyl, perhalo $C_{1-6}$ alkyl, $-SO_pR^1$, and $C_{1-6}$ alkyl; or $R^a$, and $R^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic fully or partially unsaturated heterocyclic ring having 1-5 heteroatom independently selected from O, N, or S; D is selected from $CR^1$, or N; G is selected from $-C(O)OR^1$, $-C(O)NR^aR^b$, $-NR^1SO_2R^1$, or 5 membered monocyclic fully or partially unsaturated heterocyclic ring having 1-4 heteroatoms independently selected from O, N or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{2-6}$ alkenyl, $C_{2-6}$ alkynyl, $C_{1-6}$ alkoxy, $C(O)R^1$, $R^1C(O)NR^aR^b$, $-OC(O)R^1$, $R^6$, $-(CR^aR^b)_mC(O)R^6$, $-(CR^aR^b)_mNR^7R^8$, $-NR^aC(O)-$, $-C_{1-6}$ alkoxy $C(O)NR^aR^b$, $-SO_2NR^aR^b-$, $-NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $-C(S)R^a$, $C(O)OR^1$, $C_{1-6}$ alkyl $C(O)OR^b$, $OC(O)$ $C_{1-6}$ alkyloxy, $OR_aC(O)OR_b-C_{1-6}$ alkylOC(O)OC$_{1-6}$ alkyloxy, $-SO_3H$, $-S(O)_pR^6$, $-S(O)_2NR^7R^8$ $C_{1-6}$ alkylthio or nitro; $R^6$ is selected from the group consisting of hydrogen, $-(CR^aR^b)_mOR^6$, halogen, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, $-C(O)OR^1$, $OR^5$, $-OC(O)R^6$, $-(CR^aR^b)_mC(O)NR^7R^8$, $-NR^6C(O)R^6$, $-SR^6$, $-S(O)_pR^6$, $-S(O)_2NR^7R^8$, or $-NR^6S(O)_2R^6$; $R^5$, $R^7$, and $R^8$ are independently selected from the group consisting of hydrogen, $-(CR^aR^b)_mOR^6$, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or $R^7$ and $R^8$ can be taken together to form a monocyclic or a bicyclic saturated or partially unsaturated carbocyclyl or heterocyclyl ring optionally having 1-5 heteroatoms selected from O, N or S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, $-(CR^aR^b)_mOR^6$, $-SR^6$, $-(CR^aR^b)_mNR^7R^8$, oxo, $C_{1-6}$ alkylsulfonyl, $-(CR^aR^b)_mCOOR^6$, $-(CR^aR^b)_mC(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$, and $C_{5-10}$ heteroaryl are optionally substituted with $C_{1-6}$ alkyl; $R^a$, and $R^b$ are independently selected from the group consisting of hydrogen, $-OR^6$, halogen, $C_{1-6}$ haloalkyl, perhalo $C_{1-6}$ alkyl, $-SO_pR^1$, and $C_{1-6}$ alkyl or $R^a$, and $R^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic fully or partially unsaturated heterocyclic ring having 1-5 heteroatom independently selected from O, N, or S; D is selected from $CR^1$, or N; G is selected from $-C(O)OR^1$, $-C(O)NR^aR^b$, $-NR^1SO_2R^1$, or 5 membered monocyclic fully or partially unsaturated heterocyclic ring having 1-4 heteroatoms independently selected from O, N or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NR^aR^b$, $-OC(O)R^1$, $R^6$, $-(CR^aR^b)_mC(O)R^6$, $-(CR^aR^b)_mNR^7R^8$, $-NR^aC(O)-$, $-C_{1-6}$ alkoxy $C(O)NR^aR^b$, $-SO_2NR^aR^b-$, $-NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $-C(S)R^a$, $C(O)OR^1$, $C_{1-6}$ alkyl $C(O)OR^b$, $OC(O)$ $C_{1-6}$ alkyloxy, $OR_aC(O)OR_b-C_{1-6}$ alkylOC(O)OC$_{1-6}$ alkyloxy, $-SO_3H$, $-S(O)_p R^6$, $-S(O)_2NR^7R^8$ $C_{1-6}$ alkylthio or nitro; $R^6$ is selected from the group consisting of hydrogen, $-(CR^aR^b)_mOR^6$, halogen, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, $-C(O)OR^1$, $OR^5$, $-OC(O)R^6$, $-(CR^aR^b)_mC(O)NR^7R^8$, $-NR^6C(O)R^6$, $-SR^6$, $-S(O)_pR^6$, $-S(O)_2NR^7R^8$, or $-NR^6S(O)_2R^6$; $R^5$, $R^7$, and $R^8$ are independently selected from the group consisting of hydrogen, $-(CR^aR^b)_mOR^6$, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or $R^7$ and $R^8$ can be taken together to form a monocyclic or a bicyclic saturated or partially unsaturated carbocyclyl or heterocyclyl ring optionally having 1-5 heteroatoms selected from O, N or S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, $-(CR^aR^b)_mOR^6$, $-SR^6$, $-(CR^aR^b)_mNR^7R^8$, oxo, $C_{1-6}$ alkylsulfonyl, $-(CR^aR^b)_mCOOR^6$, $-(CR^aR^b)_mC(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$, and $C_{5-10}$ heteroaryl are optionally substituted with $C_{1-6}$ alkyl; $R^a$, and $R^b$ are independently selected from the group consisting of hydrogen, $-OR^6$, halogen, $C_{1-6}$ haloalkyl, perhalo $C_{1-6}$ alkyl, $-SO_pR^1$, and $C_{1-6}$ alkyl or $R^a$, and $R^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N or S; D is selected from $CR^1$ or N; G is selected from $-C(O)OR^1$, $-C(O)NR^aR^b$, $-NR^1SO_2R^1$ or 5 membered monocyclic fully or partially unsaturated heterocyclic ring having 1-4 heteroatoms independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NR^aR^b$, $-OC(O)R^1$, $R^6$, $-(CR^aR^b)_mC(O)R^6$, $-(CR^aR^b)_mNR^7R^8$, $-NR^aC(O)-$, $-C_{1-6}$ alkoxy $C(O)NR^aR^b$, $-NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C(O)OR^1$, $C_{1-6}$ alkyl $C(O)OR^b$, $OC(O)$ $C_{1-6}$ alkyloxy, $OR_aC(O)OR_b-$ $C_{1-6}$ alkylOC(O)OC$_{1-6}$ alkyloxy, or nitro; $R^6$ is selected from the group consisting of hydrogen, $-(CR^aR^b)_mOR^6$, halogen, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, $-C(O)OR^1$, $OR^5$, $-OC(O)R^6$, $-(CR^aR^b)_mC(O)NR^7R^8$, $-NR^6C(O)R^6$, $-SR^6$, $-S(O)_pR^6$, $-S(O)_2NR^7R^8$, or $-NR^6S(O)_2R^6$; $R^5$, $R^7$, and $R^8$ are independently selected from the group consisting of hydrogen, $-(CR^aR^b)_mOR^6$, $C_{1-6}$ haloalkyl, $-(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or $R^7$ and $R^8$ can be taken together to form a monocyclic or a bicyclic saturated or partially unsaturated carbocyclyl or heterocyclyl ring optionally having 1-5 heteroatoms selected from O, N or S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, —$(CR^aR^b)_m OR^6$, —$SR^6$, —$(CR^aR^b)_m NR^7R^8$, oxo, $C_{1-6}$ alkylsulfonyl, —$(CR^aR^b)_m COOR^6$, —$(CR^aR^b)_m C(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl or $R^a$, and $R^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N or S; D is selected from $CR^1$ or N; G is selected from —$C(O)OR^1$, —$C(O)NR^aR^b$, —$NR^1SO_2R^1$ or 5 membered monocyclic fully or partially unsaturated heterocyclic ring having 1-4 heteroatoms independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NR^aR^b$, —$OC(O)R^1$, $R^6$, —$(CR^aR^b)_m C(O) R^6$, —$(CR^aR^b)_m NR^7R^8$, —$NR^aC(O)$—, —$C_{1-6}$ alkoxy $C(O) NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C(O)OR^1$, $C_{1-6}$ alkyl $C(O) OR^b$, $OC(O)$ $C_{1-6}$ alkyloxy, $OR_aC(O)OR_b$— $C_{1-6}$ alkylOC $(O)OC_{1-6}$ alkyloxy, or nitro; $R^6$ is selected from the group consisting of hydrogen, —$(CR^aR^b)_m OR^6$, halogen, $C_{1-6}$ haloalkyl, —$(CR^aR^b)_m C(O)R^6$, $C_{1-6}$ alkyl, $C_{2-6}$ alkenyl, $C_{2-6}$ alkynyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_m C(O) NR^7R^8$, —$NR^6C(O)R^6$, —$SR^6$, —$S(O)_pR^6$, —$S(O)_2NR^7R^8$, or —$NR^6S(O)_2R^6$; $R^5$, $R^7$, and $R^8$ are independently selected from the group consisting of hydrogen, —$(CR^aR^b)_m$ $OR^6$, $C_{1-6}$ haloalkyl, —$(CR^aR^b)_m C(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or $R^7$ and $R^8$ can be taken together to form a monocyclic or a bicyclic saturated or partially unsaturated carbocyclyl or heterocyclyl ring optionally having 1-5 heteroatoms selected from O, N or S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, —$(CR^aR^b)_m OR^6$, —$SR^6$, —$(CR^aR^b)_m NR^7R^8$, oxo, $C_{1-6}$ alkylsulfonyl, —$(CR^aR^b)_m COOR^6$, —$(CR^aR^b)_m C(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl or R$^a$, and R$^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N or S; D is selected from CR$^1$ or N; G is selected from —C(O)OR$^1$, —C(O)NR$^a$R$^b$, —NR$^1$SO$_2$R$^1$ or 5 membered monocyclic fully unsaturated or partially unsaturated heterocyclic ring having 1-4 heteroatom independently selected from O, N, or S; R$^1$ is selected from hydrogen, C$_{1-6}$ haloalkyl, C$_{1-6}$ alkyl, C$_{5-10}$ heteroaryl, or C$_{3-6}$ cycloalkyl, wherein C$_{3-6}$ cycloalkyl, and C$_{5-10}$ heteroaryl are optionally substituted with C$_{1-6}$ alkyl; R$^2$, R$^3$, and R$^4$ are independently selected from hydrogen, C$_{1-6}$ alkyl, C$_{3-6}$ cycloalkyl, C$_{1-6}$ alkoxy, C(O)R$^1$, R$^1$C(O)NH$_2$, —OC(O)R$^1$, C(O)OR$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —NR$^a$C(O)NR$^a$R$^b$, NR$^a$OH, C$_{1-6}$ alkoxyamino, azido, cyano, halogen, hydroxy, C$_{1-6}$ alkyl hydroxy, C$_{1-6}$ haloalkyl, perhalo C$_{1-6}$ alkyl, C$_{1-6}$ alkyl C(O)OR$^b$, OC(O) C$_{1-6}$ alkyloxy, OR$_a$C(O)OR$_b$— C$_{1-6}$ alkylOC(O) OC$_{1-6}$ alkyloxy, or nitro; R$^6$ is selected from the group consisting of hydrogen, —(CR$^a$R$^b$)$_m$OR$^6$, halogen, C$_{1-6}$ haloalkyl, —(CR$^a$R$^b$)$_m$C(O)R$^6$, C$_{1-6}$ alkyl, C$_{5-10}$ heteroaryl, C$_{3-6}$ cycloalkyl, or C$_{5-10}$ heterocyclyl, wherein C$_{5-10}$ heteroaryl, C$_{3-6}$ cycloalkyl, C$_{5-10}$ heterocyclyl are optionally substituted with C$_{1-6}$ alkyl; wherein C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, and C$_{5-10}$ heterocyclyl are optionally substituted with one or more substituents selected from hydroxy, C$_{1-6}$ alkyl, C$_{1-6}$ alkoxy, C$_{1-6}$ alkoxyalkyl, halogen, C$_{1-6}$ haloalkyl, perhalo-C$_{1-6}$ alkyl, cyano, -cyano C$_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$; R$^5$, R$^7$, and R$^8$ are independently selected from the group consisting of hydrogen, —(CR$^a$R$^b$)$_m$OR$^6$, C$_{1-4}$ haloalkyl, —(CR$^a$R$^b$)$_m$C(O)R$^6$, C$_{1-4}$ alkyl, C$_{2-4}$ alkenyl, C$_{2-4}$ alkynyl, C$_{6-8}$ aryl, C$_{5-10}$ heteroaryl, C$_{3-5}$ cycloalkyl, C$_{5-10}$ heterocyclyl, wherein, C$_{6-8}$ aryl, C$_{5-10}$ heteroaryl, C$_{3-5}$ cycloalkyl, and C$_{5-10}$ heterocyclyl are optionally substituted with C$_{1-6}$ alkyl or R$^7$ and R$^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halogen, C$_{1-6}$ alkyl, C$_{2-6}$ alkenyl, C$_{2-6}$ alkynyl, nitro, cyano, —(CR$^a$R$^b$)$_m$OR$^6$, —SR$^6$, —(CR$^a$R$^b$)$_m$NR$^7$R$^8$, oxo, C$_{1-6}$ alkylsulfonyl, —(CR$^a$R$^b$)$_m$COOR$^6$, —(CR$^a$R$^b$)$_m$C(O)NR$^7$R$^8$, C$_{3-6}$ cycloalkyl, C$_{6-10}$ aryl, C$_{5-10}$ heterocyclyl, or C$_{5-10}$ heteroaryl, wherein C$_{3-6}$ cycloalkyl, C$_{6-10}$ aryl, C$_{5-10}$ heterocyclyl, and C$_{5-10}$ heteroaryl are optionally substituted with C$_{1-6}$ alkyl; R$^a$, and R$^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl or R$^a$, and R$^b$ can be taken together to form a monocyclic or a bicyclic ring saturated or partially unsaturated optionally having 1-5 heteroatoms selected from O, N, or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N or S; D is selected from CR$^1$ or N; G is selected from —C(O)OR$^1$, —C(O)NR$^a$R$^b$, —NR$^1$SO$_2$R$^1$ or 5 membered monocyclic fully unsaturated or partially unsaturated heterocyclic ring having 1-4 heteroatom independently selected from O, N, or S; R$^1$ is selected from hydrogen, C$_{1-6}$ haloalkyl, C$_{1-6}$ alkyl, C$_{5-10}$ heteroaryl, or C$_{3-6}$ cycloalkyl, wherein C$_{3-6}$ cycloalkyl, and C$_{5-10}$ heteroaryl are optionally substituted with C$_{1-6}$ alkyl; R$^2$, R$^3$, and R$^4$ are independently selected from hydrogen, C$_{1-6}$ alkyl, C$_{3-6}$ cycloalkyl, C$_{1-6}$ alkoxy, C(O)R$^1$, R$^1$C(O)NH$_2$, —OC(O)R$^1$, C(O)OR$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —NR$^a$C(O)NR$^a$R$^b$, NR$^a$OH, C$_{1-6}$ alkoxyamino, azido, cyano, halogen, hydroxy, C$_{1-6}$ alkyl hydroxy, C$_{1-6}$ haloalkyl, perhalo C$_{1-6}$ alkyl, C$_{1-6}$ alkyl C(O)OR$^b$, OC(O) C$_{1-6}$ alkyloxy, OR$_a$C(O)OR$_b$— C$_{1-6}$ alkylOC(O) OC$_{1-6}$ alkyloxy, or nitro; R$^6$ is selected from the group consisting of hydrogen, —(CR$^a$R$^b$)$_m$OR$^6$, halogen, C$_{1-6}$ haloalkyl, —(CR$^a$R$^b$)$_m$C(O)R$^6$, C$_{1-6}$ alkyl, C$_{5-10}$ heteroaryl, C$_{3-6}$ cycloalkyl, or C$_{5-10}$ heterocyclyl, wherein C$_{5-10}$ heteroaryl, C$_{3-6}$ cycloalkyl, C$_{5-10}$ heterocyclyl are optionally substituted with C$_{1-6}$ alkyl; wherein C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, and C$_{5-10}$ heterocyclyl are optionally substituted with one or more substituents selected from hydroxy, C$_{1-6}$ alkyl, C$_{1-6}$ alkoxy, C$_{1-6}$ alkoxyalkyl, halogen, C$_{1-6}$ haloalkyl, perhalo-C$_{1-6}$ alkyl, cyano, -cyano C$_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$, or —NR$^6$S(O)$_2$R$^6$; R$^5$, R$^7$, and R$^8$ are independently selected from the group consisting of hydrogen, —(CR$^a$R$^b$)$_m$OR$^6$, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-7}$ heteroaryl, C$_{3-6}$ cycloalkyl, C$_{5-7}$ heterocyclyl, wherein, C$_{6-10}$ aryl, C$_{5-7}$ heteroaryl, C$_{3-6}$ cycloalkyl, and C$_{5-7}$ heterocyclyl are optionally substituted with C$_{1-6}$ alkyl or R$^7$ and R$^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halogen, C$_{1-6}$ alkyl, C$_{2-6}$ alkenyl, C$_{2-6}$ alkynyl, nitro, cyano, —(CR$^a$R$^b$)$_m$OR$^6$, —SR$^6$, —(CR$^a$R$^b$)$_m$NR$^7$R$^8$, oxo, C$_{1-6}$ alkylsulfonyl, —(CR$^a$R$^b$)$_m$COOR$^6$, —(CR$^a$R$^b$)$_m$C(O)NR$^7$R$^8$, C$_{3-6}$ cycloalkyl, C$_{6-10}$ aryl, C$_{5-10}$ heterocyclyl, or C$_{5-10}$ heteroaryl, wherein C$_{3-6}$ cycloalkyl, C$_{6-10}$ aryl, C$_{5-10}$ heterocyclyl, and C$_{5-10}$ heteroaryl are optionally substituted with C$_{1-6}$ alkyl; R$^a$, and R$^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl or R$^a$, and R$^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N or S; D is selected from CR$^1$ or N; G is selected from —C(O)OR$^1$, —C(O)NR$^a$R$^b$, —NR$^1$SO$_2$R$^1$ or 5 membered monocyclic fully unsaturated or partially unsaturated heterocyclic ring having 1-4 heteroatom independently selected from O, N, or S; R$^1$ is selected from hydrogen, C$_{1-6}$ haloalkyl, C$_{1-6}$ alkyl, C$_{5-10}$ heteroaryl, or C$_{3-6}$ cycloalkyl, wherein C$_{3-6}$ cycloalkyl, and C$_{5-10}$ heteroaryl are optionally substituted with C$_{1-6}$ alkyl; R$^2$, R$^3$, and R$^4$ are independently selected from hydrogen, C$_{1-6}$ alkyl, C$_{3-6}$ cycloalkyl, C$_{1-6}$ alkoxy, C(O)R$^1$, R$^1$C(O)NH$_2$, —OC(O)R$^1$, R$^6$, C(O)OR$^1$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —NR$^a$C(O)NR$^a$R$^b$, NR$^a$OH, C$_{1-6}$ alkoxyamino, azido, cyano, halogen, hydroxy, C$_{1-6}$ alkyl hydroxy, $C_{1-6}$ haloalkyl, perhalo $C_{1-6}$ alkyl, $C_{1-6}$ alkyl $C(O)OR^b$, $OC(O)\ C_{1-6}$ alkyloxy, $OR_aC(O)OR_b$—$C_{1-6}$ alkylOC(O) $OC_{1-6}$ alkyloxy, or nitro; $R^6$ is selected from the group consisting of hydrogen, —$(CR^aR^b)_mOR^6$, halogen, $C_{1-6}$ haloalkyl, —$(CR^aR^b)_mC(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$, or —$NR^6S(O)_2R^6$; $R^5$, $R^7$, and $R^8$ are independently selected from the group consisting of hydrogen, —$(CR^aR^b)_mOR^6$, $C_{1-4}$ haloalkyl, —$(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl or $R^7$ and $R^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halo, $C_1$-6 alkyl, cyano, —$(CR^aR^b)_mOR^6$, —$SR^6$, —$(CR^aR^b)_mNR^7R^8$, oxo, $C_{1-6}$ alkylsulfonyl, —$(CR^aR^b)_mCOOR^6$, —$(CR^aR^b)_mC(O)NR^7R^8$, $C_{3-6}$ cycloalkyl, $C_{6-10}$ aryl, $C_{5-10}$ heteroaryl, or $C_{5-10}$ heterocyclyl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl or $R^a$, and $R^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N or S; D is selected from $CR^1$ or N; G is selected from —$C(O)OR^1$, —$C(O)NR^aR^b$, —$NR^1SO_2R^1$ or 5 membered monocyclic fully unsaturated or partially unsaturated heterocyclic ring having 1-4 heteroatom independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NH_2$, —$OC(O)R^1$, $R^6$, $C(O)OR^1$, —$(CR^aR^b)_mC(O)R^6$, —$(CR^aR^b)_mNR^7R^8$, —$NR^aC(O)$—, —$C_{1-6}$ alkoxy $C(O)NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C_{1-6}$ alkyl $C(O)OR^b$, $OC(O)\ C_{1-6}$ alkyloxy, $OR_aC(O)OR_b$—$C_{1-6}$ alkylOC(O)$OC_{1-6}$ alkyloxy, or nitro; $R^6$ is selected from the group consisting of hydrogen, —$(CR^aR^b)_mOR^6$, halogen, $C_{1-6}$ haloalkyl, —$(CR^aR^b)_mC(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$ or —$NR^6S(O)_2R^6$; $R^5$, $R^7$, and $R^8$ are independently selected from the group consisting of hydrogen, —$(CR^aR^b)_mOR^6$, $C_{1-4}$ haloalkyl, —$(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl or $R^7$ and $R^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halo, $C_1$-6 alkyl, $C_{2-6}$ alkenyl, $C_{2-6}$ alkynyl, nitro, cyano, —$(CR^aR^b)_mOR^6$, —$SR^6$, oxo, —$(CR^aR^b)_mCOOR^6$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl or $R^a$, and $R^b$ can be taken together to form a monocyclic or a bicyclic ring saturated or partially unsaturated optionally having 1-5 heteroatoms selected from O, N or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted $C_{5-10}$ bicyclic or polycyclic unsaturated or partially unsaturated heterocyclic ring having 1-5 heteroatom independently selected from O, N or S; D is selected from $CR^1$ or N; G is selected from —$C(O)OR^1$, —$C(O)NR^aR^b$, —$NR^1SO_2R^1$ or 5 membered monocyclic fully unsaturated or partially unsaturated heterocyclic ring having 1-4 heteroatom independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NH_2$, —$OC(O)R^1$, $R^6$, $C(O)OR^1$, —$(CR^aR^b)_mC(O)R^6$, —$(CR^aR^b)_mNR^7R^8$, —$NR^aC(O)$—, —$C_{1-6}$ alkoxy $C(O)NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C_{1-6}$ alkyl $C(O)OR^b$, $OC(O)\ C_{1-6}$ alkyloxy, $OR_aC(O)OR_b$—$C_{1-6}$ alkylOC(O)$OC_{1-6}$ alkyloxy, or nitro; $R^6$ is selected from the group consisting of hydrogen, —$(CR^aR^b)_mOR^6$, halogen, $C_{1-6}$ haloalkyl, —$(CR^aR^b)_mC(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$ or —$NR^6S(O)_2R^6$; $R^5$, $R^7$, and $R^8$ are independently selected from the group consisting of hydrogen, —$(CR^aR^b)_mOR^6$, $C_{1-4}$ haloalkyl, —$(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl; or $R^7$ and $R^8$ can be taken together to form a monocyclic or a bicyclic saturated or partially unsaturated carbocyclyl or heterocyclyl ring optionally having 1-4 heteroatoms selected from O, N, or S, wherein the monocyclic or a bicyclic ring carbocyclyl or heterocyclyl is further optionally substituted with 1 to 4 substituents independently selected from halo, $C_{1-6}$ alkyl, cyano, —$(CR^aR^b)_mOR^6$, —$SR^6$, oxo, —$(CR^aR^b)_m$ $COOR^6$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl; or $R^a$, and $R^b$ can be taken together to form a monocyclic or a bicyclic ring saturated or partially unsaturated optionally having 1-5 heteroatoms selected from O, N, or S; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted $C_{5-10}$ bicyclic or polycyclic unsaturated or partially unsaturated heterocyclic ring having 1-5 heteroatom independently selected from O, N or S; D is selected from $CR^1$ or N; G is selected from —$C(O)OR^1$, —$C(O)NR^aR^b$, —$NR^1SO_2R^1$ or 5 membered monocyclic fully unsaturated or partially unsaturated heterocyclic ring having 1-4 heteroatom independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NH_2$, —$OC(O)R^1$, $R^6$, $C(O)OR^1$, —$(CR^aR^b)_mC(O)R^6$, —$(CR^aR^b)_mNR^7R^8$, —$NR^aC(O)$—, —$C_{1-6}$ alkoxy $C(O)$ $NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C_{1-6}$ alkyl $C(O)OR^b$, $OC(O)$ $C_{1-6}$ alkyloxy, $OR_aC(O)OR_b$— $C_{1-6}$ alkylOC(O)OC$_{1-6}$ alkyloxy, or nitro; $R^6$ is selected from the group consisting of hydrogen, —$(CR^aR^b)_mOR^6$, halogen, $C_{1-6}$ haloalkyl, —$(CR^aR^b)_mC(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$ or —$NR^6S(O)_2R^6$; $R^5$, $R^7$, and $R^8$ are independently selected from the group consisting of hydrogen, —$(CR^aR^b)_mOR^6$, $C_{1-4}$ haloalkyl, —$(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl; or $R^7$ and $R^8$ can be taken together to form a monocyclic or a bicyclic saturated or partially unsaturated carbocyclyl or heterocyclyl ring optionally having 1-4 heteroatoms selected from O, N, or S, wherein the monocyclic or a bicyclic ring carbocyclyl or heterocyclyl is further optionally substituted with 1 to 4 substituents independently selected from halo, $C_{1-6}$ alkyl, cyano, —$(CR^aR^b)_mOR^6$, —$SR^6$, oxo, —$(CR^aR^b)_m$ $COOR^6$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl; m is 0 to 4; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted $C_{5-10}$ bicyclic or polycyclic unsaturated or partially unsaturated heterocyclic ring having 1-5 heteroatom independently selected from O, N or S; D is selected from $CR^1$ or N; G is selected from —$C(O)OR^1$, —$C(O)NR^aR^b$, —$NR^1SO_2R^1$ or 5 membered monocyclic fully unsaturated or partially unsaturated heterocyclic ring having 1-4 heteroatom independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NH_2$, —$OC(O)R^1$, $R^6$, $C(O)OR^1$, —$(CR^aR^b)_mC(O)R^6$, —$(CR^aR^b)_mNR^7R^8$, —$NR^aC(O)$—, —$C_{1-6}$ alkoxy $C(O)$ $NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C_{1-6}$ alkyl $C(O)OR^b$, $OC(O)$ $C_{1-6}$ alkyloxy, $OR_aC(O)OR_b$— $C_{1-6}$ alkylOC(O) 0 $C_{1-6}$ alkyloxy, or nitro; $R^6$ is selected from the group consisting of hydrogen, —$(CR^aR^b)_mOR^6$, halogen, $C_{1-6}$ haloalkyl, —$(CR^aR^b)_mC(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$ or —$NR^6S(O)_2R^6$; $R^5$, $R^7$, and $R^8$ are independently selected from the group consisting of hydrogen, —$(CR^aR^b)_mOR^6$, $C_{1-4}$ haloalkyl, —$(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl; or $R^7$ and $R^8$ can be taken together to form a monocyclic or a bicyclic saturated or partially unsaturated carbocyclyl or heterocyclyl ring optionally having 1-4 heteroatoms selected from O, N, or S, wherein the monocyclic or a bicyclic ring carbocyclyl or heterocyclyl is further optionally substituted with 1 to 4 substituents independently selected from halo, $C_{1-6}$ alkyl, cyano, —$(CR^aR^b)_mOR^6$, —$SR^6$, oxo, —$(CR^aR^b)_m$ $COOR^6$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl; or $R^a$, and $R^b$ can be taken together to form a monocyclic or a bicyclic ring saturated or partially unsaturated optionally having 1-5 heteroatoms selected from O, N, or S; m is 0 to 3; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N, or S; D is selected from $CR^1$ or N; G is selected from —$C(O)OR^1$, —$C(O)NR^aR^b$, —$NR^1SO_2R^1$ or 5 membered monocyclic fully unsaturated or partially unsaturated heterocyclic ring having 1-4 heteroatom independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NH_2$, —$OC(O)R^1$, $R^6$, $C(O)OR^1$, —$(CR^aR^b)_mC(O)R^6$, —$(CR^aR^b)_mNR^7R^8$, —$NR^aC(O)$—, —$C_{1-6}$ alkoxy $C(O)NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C_{1-6}$ alkyl $C(O)OR^b$, $OC(O)$ $C_{1-6}$ alkyloxy, $OR_aC(O)OR_b$— $C_{1-6}$ alkylOC(O) O $C_{1-6}$ alkyloxy, or nitro; $R^6$ is selected from the group consisting of hydrogen, —$(CR^aR^b)_mOR^6$, halogen, $C_{1-6}$ haloalkyl, —$(CR^aR^b)_mC(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl; wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$, or —$NR^6S(O)_2R^6$; $R^5$, $R^7$, and $R^8$ are independently selected from the group consisting of hydrogen, —$(CR^aR^b)_mOR^6$, $C_{1-4}$ haloalkyl, —$(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl; or $R^7$ and $R^8$ can be taken together to form a monocyclic or a bicyclic saturated or partially unsaturated carbocyclyl or heterocyclyl ring optionally having 1-4 heteroatoms selected from O, N, or S, wherein the monocyclic or a bicyclic ring carbocyclyl or heterocyclyl is further optionally substituted with 1 to 4 substituents independently selected from halo, $C_{1-6}$ alkyl, cyano, —$(CR^aR^b)_mOR^6$, —$SR^6$, oxo, —$(CR^aR^b)_m$ $COOR^6$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl; $R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl; or m is 0 to 3; n is 1 to 3; p is 0-2.

In an embodiment of the present disclosure, there is provided a compound of Formula I, their tautomers, polymorphs, stereoisomers, prodrugs, solvates, pharmaceutically acceptable salts thereof as described herein, wherein A is substituted or unsubstituted 5-10 membered bicyclic or polycyclic unsaturated or partially unsaturated heterocyclic ring having 1-5 heteroatom independently selected from O, N, or S; D is selected from $CR^1$ or N; G is selected from —$C(O)OR^1$, —$C(O)NR^aR^b$, —$NR^1SO_2R^1$ or 5 membered monocyclic fully unsaturated or partially unsaturated heterocyclic ring having 1-4 heteroatom independently selected from O, N, or S; $R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl; $R^2$, $R^3$, and $R^4$ are independently selected from hydrogen, $C_{1-6}$ alkyl, $C_{3-6}$ cycloalkyl, $C_{1-6}$ alkoxy, $C(O)R^1$, —$OC(O)R^1$, $R^6$, $C(O)OR^1$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $C_{1-6}$ alkyl $C(O)$ OR$^b$, OC(O) C$_{1-6}$ alkyloxy, OR$_a$C(O)OR$_b$— C$_{1-6}$ alkylOC(O)OC$_{1-6}$ alkyloxy, or nitro; R$^6$ is selected from the group consisting of hydrogen, —(CR$^a$R$^b$)$_m$OR$^6$, halogen, C$_{1-6}$ haloalkyl, —(CR$^a$R$^b$)$_m$C(O)R$^6$, C$_{1-6}$ alkyl, C$_{5-10}$ heteroaryl, C$_{3-6}$ cycloalkyl, or C$_{5-10}$ heterocyclyl, wherein C$_{5-10}$ heteroaryl, C$_{3-6}$ cycloalkyl, C$_{5-10}$ heterocyclyl are optionally substituted with C$_{1-6}$ alkyl; wherein C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, and C$_{5-10}$ heterocyclyl are optionally substituted with one or more substituents selected from hydroxy, C$_{1-6}$ alkyl, C$_{1-6}$ alkoxy, C$_{1-6}$ alkoxyalkyl, halogen, C$_{1-6}$ haloalkyl, perhalo-C$_{1-6}$ alkyl, cyano, -cyano C$_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$, or —NR$^6$S(O)$_2$R$^6$; R$^5$, R$^7$, and R$^8$ are independently selected from the group consisting of hydrogen, —(CR$^a$R$^b$)$_m$OR$^6$, C$_{1-4}$ haloalkyl, —(CR$^a$R$^b$)$_m$C(O)R$^6$, C$_{1-4}$ alkyl, C$_{2-4}$ alkenyl, C$_{2-4}$ alkynyl, C$_{6-8}$ aryl, 5-7 membered heteroaryl, C$_{3-5}$ cycloalkyl, 5-7 membered heterocyclyl, wherein, C$_{6-8}$ aryl, 5-7 membered heteroaryl, C$_{3-5}$ cycloalkyl, and 5-7 membered heterocyclyl are optionally substituted with C$_{1-6}$ alkyl; or R$^7$ and R$^8$ can be taken together to form a monocyclic or a bicyclic saturated or partially unsaturated carbocyclyl or heterocyclyl ring optionally having 1-4 heteroatoms selected from O, N, or S, wherein the monocyclic or a bicyclic ring carbocyclyl or heterocyclyl is further optionally substituted with 1 to 4 substituents independently selected from halo, C$_{1-6}$ alkyl, cyano, —(CR$^a$R$^b$)$_m$OR$^6$, —SR$^6$, oxo, —(CR$^a$R$^b$)$_m$COOR$^6$, C$_{3-6}$ cycloalkyl, C$_{6-10}$ aryl, C$_{5-10}$ heterocyclyl, or C$_{5-10}$ heteroaryl, wherein C$_{3-6}$ cycloalkyl, C$_{6-10}$ aryl, C$_{5-10}$ heterocyclyl, and C$_{5-10}$ heteroaryl are optionally substituted with C$_{1-6}$ alkyl; R$^a$, and R$^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl; or m is 1; n is 1 or 2; p is 0-2.

In an embodiment of the present disclosure, there is provided a compound of Formula I, their tautomers, polymorphs, stereoisomers, prodrugs, solvates, pharmaceutically acceptable salts thereof as described herein, which is selected from a group consisting of:

2-[3-[4-(8-isoquinolyloxy)-2-(trifluoromethyl)phenoxy]phenyl]acetic acid (A1),
2-[3-[4-phthalazin-5-yloxy-2-(trifluoromethyl)phenoxy]phenyl]acetic acid (A2),
3-[3-[4-phthalazin-5-yloxy-2-(trifluoromethyl)phenoxy]phenyl]propanoic acid (A3),
2-[3-[4-(8-chlorophthalazin-5-yl)oxy-2-(trifluoromethyl)phenoxy]phenyl]acetic acid (A4),
2-[3-[4-(1-methylindazol-7-yl)oxy-2-(trifluoromethyl)phenoxy]phenyl]acetic acid (A5),
2-[3-[4-(6-quinolyloxy)-2-(trifluoromethyl)phenoxy]phenyl]acetic acid (A6),
3-[3-[4-imidazo[1,2-a]pyridin-8-yloxy-2-(trifluoromethyl)phenoxy]phenyl]propanoic acid (A7),
2-[3-[4-[(5-fluoro-8-isoquinolyl)oxy]-2-(trifluoromethyl)phenoxy]phenyl]acetic acid (A8),
2-[3-[4-quinazolin-5-yloxy-2-(trifluoromethyl)phenoxy]phenyl]acetic acid (A9),
3-[3-[4-[(2-methyl-3,4-dihydro-1H-isoquinolin-8-yl)oxy]-2-(trifluoromethyl) phenoxy]phenyl]propanoic acid (A10),
3-[3-[4-(2,3-dihydro-1,4-benzodioxin-5-yloxy)-2-(trifluoromethyl)phenoxy]phenyl]propanoic acid (A11),
3-[3-[4-(8-quinolyloxy)-2-(trifluoromethyl)phenoxy]phenyl]propanoic acid (A12),
3-[3-[4-(4-quinolyloxy)-2-(trifluoromethyl)phenoxy]phenyl]propanoic acid (A13), 3-[3-[4-(5-isoquinolyloxy)-2-(trifluoromethyl)phenoxy]phenyl]propanoic acid (A14),
2-[3-[4-(2-methylindazol-4-yl)oxy-2-(trifluoromethyl)phenoxy]phenyl]acetic acid (A15),
2-[3-[4-(1-methylindazol-4-yl)oxy-2-(trifluoromethyl)phenoxy]phenyl]acetic acid (A16),
2-[3-[4-([1,2,4]triazolo[4,3-a]pyridin-5-yloxy)-2-(trifluoromethyl)phenoxy]phenyl]acetic acid (A17),
2-[3-[4-(3,4-dihydro-2H-1,4-benzoxazin-6-yloxy)-2-(trifluoromethyl)phenoxy]phenyl]acetic acid (A18),
2-[3-[4-([1,2,4]triazolo[4,3-a]pyridin-7-yloxy)-2-(trifluoromethyl)phenoxy]phenyl]acetic acid (A19),
2-[3-[4-[1-(oxetan-3-yl)indol-6-yl]oxy-2-(trifluoromethyl)phenoxy]phenyl]acetic acid (A20),
2-[3-[4-[1-(oxetan-3-yl)indazol-6-yl]oxy-2-(trifluoromethyl)phenoxy]phenyl]acetic acid (A21),
2-[3-[4-[2-(oxetan-3-yl)indazol-6-yl]oxy-2-(trifluoromethyl)phenoxy]phenyl]acetic acid (A22),
2-[3-[4-[1-(oxetan-3-yl)indazol-5-yl]oxy-2-(trifluoromethyl)phenoxy]phenyl]acetic acid (A23),
2-[3-[4-[2-(oxetan-3-yl)indazol-5-yl]oxy-2-(trifluoromethyl)phenoxy]phenyl]acetic acid (A24),
2-[3-[4-[3-(oxetan-3-yl)benzotriazol-5-yl]oxy-2-(trifluoromethyl) phenoxy]phenyl]acetic acid (A25),
2-[3-[4-[3-(oxetan-3-yl)benzimidazol-5-yl]oxy-2-(trifluoromethyl)phenoxy]phenyl]acetic acid (A26),
2-[3-[4-[2-methyl-3-(oxetan-3-yl)benzimidazol-5-yl]oxy-2-(trifluoromethyl) phenoxy]phenyl]acetic acid (A27),
2-[3-[2-(difluoromethyl)-4-[2-methyl-3-(oxetan-3-yl)benzimidazol-5-yl]oxy-phenoxy]phenyl]acetic acid (A28),
2-[3-[4-[1-(oxetan-3-yl)imidazo[4,5-b]pyridin-6-yl]oxy-2-(trifluoromethyl) phenoxy]phenyl]acetic acid (A29),
2-[3-[4-[1-(oxetan-3-yl)pyrrolo[2,3-b]pyridin-6-yl]oxy-2-(trifluoromethyl) phenoxy]phenyl]acetic acid (A30),
6-[4-[3-(carboxymethyl)phenoxy]-3-(trifluoromethyl)phenoxy]imidazo[1,5-a]pyridine-3-carboxylic acid (A31),
2-[3-[4-[1-(carboxymethyl)indol-5-yl]oxy-2-(trifluoromethyl)phenoxy]phenyl]acetic acid (A32),
2-[3-[4-[1-(carboxymethyl)indol-6-yl]oxy-2-(trifluoromethyl)phenoxy]phenyl]acetic acid (A33),
3-[4-[4-(8-isoquinolyloxy)-2-(trifluoromethyl)phenoxy]phenyl]propanoic acid (A34),
3-[3-[4-(2-methylindazol-5-yl)oxy-2-(trifluoromethyl)phenoxy]phenyl]propanoic acid (A35),
2-[3-[[5-(8-isoquinolyloxy)-3-(trifluoromethyl)-2-pyridyl]oxy]phenyl]acetic acid (A36),
3-[3-[4-imidazo[1,2-a]pyridin-5-yloxy-2-(trifluoromethyl)phenoxy]phenyl]propanoic acid (A37),
2-[3-[2-cyclopropyl-4-(8-isoquinolyloxy)phenoxy]phenyl]acetic acid (A38),
2-[3-[2-cyclopropyl-4-[2-methyl-3-(oxetan-3-yl)benzimidazol-5-yl]oxy-phenoxy]phenyl]acetic acid (A39),
2-[3-[4-[(1-chloro-8-isoquinolyl)oxy]-2-(trifluoromethyl)phenoxy]phenyl]acetic acid (A40),
2-[3-[4-[(1-methyl-8-isoquinolyl)oxy]-2-(trifluoromethyl)phenoxy]phenyl]acetic acid (A41),
3-[3-[4-(8-isoquinolyloxy)-2-(trifluoromethyl)phenoxy]phenyl]propanoic acid (A42),
3-[3-[4-(1,2,3,4-tetrahydroisoquinolin-8-yloxy)-2-(trifluoromethyl) phenoxy]phenyl]propanoic acid (A43), 3-[3-[4-indan-1-yloxy-2-(trifluoromethyl)phenoxy]phenyl] propanoic acid (A44), 3-[3-[4-(1H-indazol-5-yloxy)-2-(trifluoromethyl) phenyl]]propanoic acid (A45), 2-[3-[4-[(3-cyano-1H-indazol-5-yl)oxy]-2-(trifluoromethyl) phenoxy]phenyl]acetic acid (A46), 5-[4-[3-(carboxymethyl)phenoxy]-3-(trifluoromethyl)phenoxy]-1H-indazole-3-carboxylic acid (A47), 2-[3-[4-(1H-indazol-4-yloxy)-2-(trifluoromethyl)phenoxy] phenyl]acetic acid (A48), 2-[3-[4-imidazo[1,5-a]pyridin-5-yloxy-2-(trifluoromethyl) phenoxy]phenyl]acetic acid (B1), 2-[3-[4-imidazo[1,5-a]pyridin-8-yloxy-2-(trifluoromethyl) phenoxy]phenyl]acetic acid (B2), 2-[3-[4-(3-methylimidazo[1,5-a]pyridin-5-yl)oxy-2-(trifluoromethyl)phenoxy]phenyl]acetic acid (B3), 2-[3-[4-(3-methylimidazo[1,5-a]pyridin-8-yl)oxy-2-(trifluoromethyl)phenoxy]phenyl]acetic acid (B4), 2-[3-[4-[3-(oxetan-3-yl)imidazo[1,5-a]pyridin-6-yl]oxy-2-(trifluoromethyl) phenoxy]phenyl]acetic acid (B5), 2-[3-[4-(8-isoquinolyloxy)-2-(trifluoromethyl)phenoxy] phenyl]-N-methylsulfonyl-acetamide (C1), 3-[3-[4-(8-isoquinolyloxy)-2-(trifluoromethyl)phenoxy] phenyl]propanamide (C2), 2-[3-[4-(8-isoquinolyloxy)-2-(trifluoromethyl)phenoxy] phenyl]acetamide (C3), 8-[4-[3-[2-(4H-1,2,4-triazol-3-yl)ethyl]phenoxy]-3-(trifluoromethyl)phenoxy]isoquinoline (D1), 8-[4-[3-[2-(1H-tetrazol-5-yl)ethyl]phenoxy]-3-(trifluoromethyl)phenoxy]isoquinoline (D2), 8-[4-[3-(1H-tetrazol-5-ylmethyl)phenoxy]-3-(trifluoromethyl) phenoxy]isoquinoline (D3), and 2-[3-[4-(8-isoquinolyloxy)-3-(trifluoromethyl)phenoxy] phenyl]acetic acid (E1).

In an embodiment of the present disclosure there is provided a process of preparation of compounds of Formula (I) or its tautomers, polymorphs, stereoisomers, prodrugs, solvate, co-crystals or pharmaceutically acceptable salts thereof.

In an embodiment of the present disclosure there is provided a process of preparation of compounds of Formula (I) or its tautomers, polymorphs, stereoisomers, prodrugs, solvate, co-crystals or pharmaceutically acceptable salts thereof, wherein the compounds of Formula I are obtained by reacting compounds of Formula II, and compounds of Formula III.

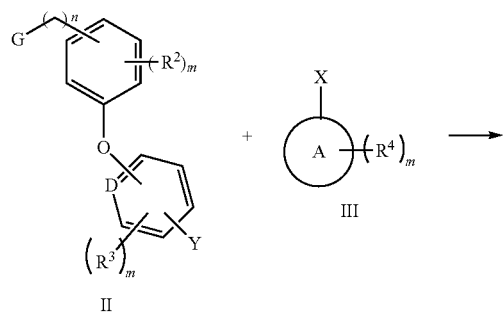

II

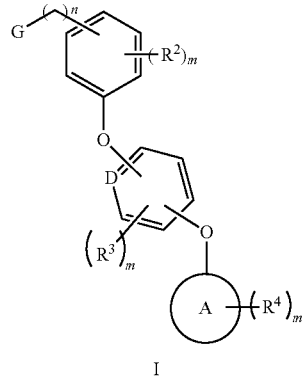

I

In an embodiment of the present disclosure, there is provided a process of preparation of compounds of Formula (I) or its tautomers, polymorphs, stereoisomers, prodrugs, solvate, co-crystals or pharmaceutically acceptable salts thereof, wherein the G of Formula II is selected from —C(O)OR$^1$, —C(O)NR$^a$R$^b$, —NR$^1$SO$_2$R$^1$ or 5-7 membered monocyclic fully or partially unsaturated heterocyclic ring having 1-4 heteroatom independently selected from O, N, or S; R$^1$ is selected from hydrogen, C$_{1-6}$ haloalkyl, C$_{1-6}$ alkyl, C$_{6-10}$ aryl, C$_{5-10}$ heteroaryl, C$_{3-6}$ cycloalkyl, or C$_{5-10}$ heterocyclyl, wherein C$_{6-10}$ aryl, C$_{3-6}$ cycloalkyl, C$_{5-10}$ heteroaryl, and C$_{5-10}$ heterocyclyl are optionally substituted with C$_{1-6}$ alkyl; R$^2$, and R$^3$ are independently selected from hydrogen, C$_{1-6}$ alkyl, C$_{3-6}$ cycloalkyl, C$_{2-6}$ alkenyl, C$_{2-6}$ alkynyl, C$_{1-6}$ alkoxy, C(O)R$^1$, R$^1$C(O)NH$_2$, —OC(O)R$^1$, R$^6$, C(O)OR$^1$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —SO$_2$NR$^a$R$^b$—, —NR$^a$C(O)NR$^a$R$^b$, NR$^a$OH, C$_{1-6}$ alkoxyamino, azido, cyano, halogen, hydroxy, C$_{1-6}$ alkyl hydroxy, C$_{1-6}$ haloalkyl, perhalo C$_{1-6}$ alkyl, —C(S)R$^a$, C$_{1-6}$ alkyl C(O)OR$^b$, OC(O) C$_{1-6}$ alkyloxy, OR$_a$C(O)OR$_b$— C$_{1-6}$ alkylOC(O)OC$_{1-6}$ alkyloxy, —SO$_3$H, —S(O)$_p$R$^6$, —S(O)$_2$NR$^7$R$^8$ C$_{1-6}$ alkylthio, or nitro; R$^6$ is selected from the group consisting of hydrogen, —(CR$^a$R$^b$)$_m$OR$^6$, halogen, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, or C$_{5-10}$ heterocyclyl, wherein C$_{6-10}$ aryl, C$_{5-10}$ heteroaryl, C$_{3-6}$ cycloalkyl, C$_{5-10}$ heterocyclyl are optionally substituted with C$_{1-6}$ alkyl; wherein C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, and C$_{5-10}$ heterocyclyl are optionally substituted with one or more substituents selected from hydroxy, C$_{1-6}$ alkyl, C$_{1-6}$ alkoxy, C$_{1-6}$ alkoxyalkyl, halogen, C$_{1-6}$ haloalkyl, perhalo-C$_{1-6}$ alkyl, cyano, -cyano C$_{1-6}$ alkyl-, amino, —C(O)OR$^1$, OR$^5$, —OC (O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$, or —NR$^6$S(O)$_2$R$^6$; R$^5$, R$^7$, and R$^8$ are independently selected from the group consisting of hydrogen, —(CR$^a$R$^b$)$_m$OR$^6$, C$_{1-6}$ haloalkyl, —(CR$^a$R$^b$)$_m$C (O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, C$_{5-10}$ heterocyclyl, wherein, C$_{6-10}$ aryl, C$_{5-10}$ heteroaryl, C$_{3-6}$ cycloalkyl, and C$_{5-10}$ heterocyclyl are optionally substituted with C$_{1-6}$ alkyl; or R$^7$ and R$^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halo, C$_{1-6}$ alkyl, C$_{2-6}$ alkenyl, C$_{2-6}$ alkynyl, nitro, cyano, —(CR$^a$R$^b$)$_m$OR$^6$, —SR$^6$, —(CR$^a$R$^b$)$_m$NR$^7$R$^8$, oxo, C$_{1-6}$ alkylsulfonyl, —(CR$^a$R$^b$)$_m$COOR$^6$, —(CR$^a$R$^b$)$_m$C(O)NR$^7$R$^8$, C$_{3-6}$ cycloalkyl, C$_{6-10}$ aryl, C$_{5-10}$ heterocyclyl, or C$_{5-10}$ heteroaryl, wherein C$_{3-6}$ cycloalkyl, C$_{6-10}$ aryl, C$_{5-10}$ heterocyclyl, and C$_{5-10}$ heteroaryl are optionally substituted with C$_{1-6}$ alkyl; R$^a$, and R$^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl; or R$^a$, and R$^b$ can be taken together to form a monocyclic or a bicyclic ring saturated or partially unsaturated optionally having 1-5 heteroatoms selected from O, N, or S; m is 0 to 4; n is 0 to 3; p is 0-2; and A of Formula III is substituted or unsubstituted 5-10 membered bicyclic or polycyclic fully or partially unsaturated heterocyclic ring having 1-5 heteroatoms independently selected from O, N or S; R$^4$ of Formula III is independently selected from hydrogen, C$_{1-6}$ alkyl, C$_{3-6}$ cycloalkyl, C$_{2-6}$ alkenyl, C$_{2-6}$ alkynyl, C$_{1-6}$ alkoxy, C(O)R$^1$, R$^1$C(O)NH$_2$, —OC(O)R$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —SO$_2$NR$^a$R$^b$—, —NR$^a$C(O)NR$^a$R$^b$, NR$^a$OH, C$_{1-6}$ alkoxyamino, azido, cyano, halogen, hydroxy, C$_{1-6}$ alkyl hydroxy, C$_{1-6}$ haloalkyl, perhalo C$_{1-6}$ alkyl, —C(S)R$^a$, C$_{1-6}$ alkyl C(O)OR$^b$, OC(O) C$_{1-6}$ alkyloxy, OR$_a$C(O)OR$_b$— C$_{1-6}$ alkylOC(O)OC$_{1-6}$ alkyloxy, —SO$_3$H, —S(O)$_p$R$^6$, —S(O)$_2$NR$^7$R$^8$ C$_{1-6}$ alkylthio, or nitro; R$^6$ is selected from the group consisting of hydrogen, —(CR$^a$R$^b$)$_m$OR$^6$, halogen, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, or C$_{5-10}$ heterocyclyl, wherein C$_{6-10}$ aryl, C$_{5-10}$ heteroaryl, C$_{3-6}$ cycloalkyl, C$_{5-10}$ heterocyclyl are optionally substituted with C$_{1-6}$ alkyl, wherein C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, and C$_{5-10}$ heterocyclyl are optionally substituted with one or more substituents selected from hydroxy, C$_{1-6}$ alkyl, C$_{1-6}$ alkoxy, C$_{1-6}$ alkoxyalkyl, halogen, C$_{1-6}$ haloalkyl, perhalo-C$_{1-6}$ alkyl, cyano, -cyano C$_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$, or —NR$^6$S(O)$_2$R$^6$; R$^5$, R$^7$, and R$^8$ are independently selected from the group consisting of hydrogen, —(CR$^a$R$^b$)$_m$OR$^6$, C$_{1-6}$ haloalkyl, —(CR$^a$R$^b$)$_m$C(O)R$^6$, C$_{1-6}$ alkyl, C$_{2-6}$ alkenyl, C$_{2-6}$ alkynyl, C$_{6-10}$ aryl, C$_{5-10}$ heteroaryl, C$_{3-6}$ cycloalkyl, C$_{5-10}$ heterocyclyl, wherein, C$_{6-10}$ aryl, C$_{5-10}$ heteroaryl, C$_{3-6}$ cycloalkyl, and C$_{5-10}$ heterocyclyl are optionally substituted with C$_{1-6}$ alkyl; or R$^7$, and R$^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halo, C$_{1-6}$ alkyl, C$_{2-6}$ alkenyl, C$_{2-6}$ alkynyl, nitro, cyano, —(CR$^a$R$^b$)$_m$OR$^6$, —SR$^6$, —(CR$^a$R$^b$)$_m$NR$^7$R$^8$, oxo, C$_{1-6}$ alkylsulfonyl, —(CR$^a$R$^b$)$_m$COOR$^6$, —(CR$^a$R$^b$)$_m$C(O)NR$^7$R$^8$, C$_{3-6}$ cycloalkyl, C$_{6-10}$ aryl, C$_{5-10}$ heterocyclyl, or C$_{5-10}$ heteroaryl, wherein C$_{3-6}$ cycloalkyl, C$_{6-10}$ aryl, C$_{5-10}$ heterocyclyl, and C$_{5-10}$ heteroaryl are optionally substituted with C$_{1-6}$ alkyl; R$^a$, and R$^b$ are independently selected from the group consisting of hydrogen, —OR$^6$, halogen, C$_{1-6}$ haloalkyl, perhalo C$_{1-6}$ alkyl, —SO$_p$R$^1$, and C$_{1-6}$ alkyl; or R$^a$, and R$^b$ can be taken together to form a monocyclic or a bicyclic ring saturated or partially unsaturated optionally having 1-5 heteroatoms selected from O, N or S; and m is 0 to 4; and X and Y is independently selected from halogen, CF$_3$SO$_3$—, boronate ester or boronic acid, provided X and Y cannot be the same.

In an embodiment of the present disclosure, there is provided a pharmaceutical composition comprising a compound of Formula (I), their tautomers, polymorphs, stereoisomers, prodrugs, solvates, or a pharmaceutically acceptable salt thereof as described herein, together with a pharmaceutically acceptable carrier, optionally in combination with one or more other pharmaceutical compositions.

In an embodiment of the present disclosure, there is provided a pharmaceutical composition comprising a compound of Formula (I), their tautomers, polymorphs, stereoisomers, prodrugs, solvates, or a pharmaceutically acceptable salt thereof as described herein, wherein the composition is in the form of a tablet, capsule, powder, syrup, solution, aerosol, or suspension.

In an embodiment of the present disclosure, there is provided a compound of Formula I, their tautomers, polymorphs, stereoisomers, prodrugs, solvates, pharmaceutically acceptable salts thereof as described herein, for use in the manufacture of a medicament of disease states mediated by GPR91.

In an embodiment of the present disclosure, there is provided a method for the treatment and/or prevention of various diseases, including cancer and infectious diseases, comprising administering to a subject suffering from the proliferative disorder or cancer, a therapeutically effective amount of the compounds of Formula I, their tautomers, polymorphs, stereoisomers, prodrugs, solvates, pharmaceutically acceptable salts thereof as described herein, or the pharmaceutical composition comprising a compound of Formula (I), their tautomers, polymorphs, stereoisomers, prodrugs, solvates, or a pharmaceutically acceptable salt thereof as described herein, with other clinically relevant cytotoxic agents or non-cytotoxic agents to a subject in need thereof.

In an embodiment of the present disclosure, there is provided a use of the compounds of Formula I, their tautomers, polymorphs, stereoisomers, prodrugs, solvates, pharmaceutically acceptable salts thereof as described herein, or the pharmaceutical composition comprising a compound of Formula (I), their tautomers, polymorphs, stereoisomers, prodrugs, solvates, or a pharmaceutically acceptable salt thereof as described herein, for the treatment and/or prevention of various diseases including proliferative disorder or cancer; or treatment of cancer together with other clinically relevant cytotoxic agents or non-cytotoxic agents.

In an embodiment of the present disclosure there is provided a method for the treatment of neovascularization, macular degeneration, diabetic nephropathy, liver diseases, inflammation, cancer, metabolic diseases, cardiovascular disease, hypertension, non alcoholic steatohepetitis (NAASH), fatty liver disease (FLD), non alcoholic fatty liver disease (NAFLD), retinal angiogenesis, said method comprising administering a combination of the compound of Formula (I), their tautomers, polymorphs, stereoisomers, prodrugs, solvates, or a pharmaceutically acceptable salt thereof as described herein, or the pharmaceutical composition comprising a compound of Formula (I), their tautomers, polymorphs, stereoisomers, prodrugs, solvates, or a pharmaceutically acceptable salt thereof as described herein, with other clinically relevant cytotoxic agents or non-cytotoxic agents to a subject in need thereof.

In an embodiment of the present disclosure there is provided a method for the treatment of neovascularization, macular degeneration, diabetic nephropathy, liver diseases, inflammation, cancer, metabolic diseases, cardiovascular disease, hypertension, non alcoholic steatohepetitis (NAASH), fatty liver disease (FLD), non alcoholic fatty liver disease (NAFLD), retinal angiogenesis, said method comprising administering a combination of the compounds of Formula I as described herein, or the pharmaceutical composition as described herein, with other clinically relevant immune modulators agents to a subject in need of thereof.

EXAMPLES

As used herein the symbols and conventions used in these processes, schemes and examples are consistent with those used in the contemporary scientific literature, for example, the *Journal of the American Chemical Society* or the *Journal of OrganicChemistry*, or *Journal of Biological chemistry*, or *Organic Letters*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Abbreviations:
Ac Acetyl;
$Ac_2O$ Acetic anhydride;
ACN Acetonitrile;
AIBN Azobis(isobutyronitrile);
BINAP 2,2'-Bis(diphenylphosphino)-1,1'-binaphthyl;
BMS Borane-dimethyl sulfide complex;
Bn Benzyl;
Boc Tert-Butoxycarbonyl;
$Boc_2O$ Di-tert-butyl dicarbonate;
BuLi Butyllithium;
CsF Cesium fluoride;
DCE 1,2-Dichloroethane;
DCM Dichloromethane;
DDQ 2,3-Dichloro-5,6-dicyano-1,4-benzoquinone;
DMS Dimethyl sufide;
ATP Adenosine triphosphate;
Bis-pinacolatodiboron 4,4,4',4',5,5,5',5'-Octamethyl-2,2'-bi-1,3,2-dioxaborolane;
BSA Bovine serum albumin;
C18 Refers to 18-carbon alkyl groups on silicon in HPLC stationary phase;
$CH_3CN$ Acetonitrile;
Cy Cyclohexyl;
DIPEA Hünig's base, N-ethyl-N-(1-methylethyl)-2-propanamine;
Dioxane 1,4-Dioxane;
DMAP 4Ddimethylaminopyridine;
DME 1,2-Dimethoxyethane;
DMF N,N-Dimethylformamide;
DMSO Dimethylsulfoxide;
DPPA Diphenyl phosphoryl azide;
EtOAc Ethyl acetate;
EtOH Ethanol;
$Et_2O$ Diethyl ether;
HOAc Acetic acid;
HPLC High pressure liquid chromatography;
HMDS Hexamethyldisilazide;
IPA Isopropylalcohol;
LAH Lithium aluminum hydride;
LDA Lithium diisopropylamide;
LHMDS Lithium hexamethyldisilazide;
MeOH Methanol;
MPLC Medium pressure liquid chromatography;
MTBE Methyl tert-butyl ether;
mCPBA m-Chloroperbezoic acid;
NaHMDS Sodium hexamethyldisilazide;
NBS N-bromosuccinimide;
NMR Nuclear magnetic resonance;
$Pd_2(dba)_3$ Tris(dibenzylideneacetone)dipalladium(0);
$Pd(dppf)Cl_2$.DCMComplex [1,1'-Bis(diphenylphosphino) ferrocene]dichloropalladium(II). dichloromethane complex;
RPHPLC Reverse phase high pressure liquid chromatography;
RT Room temperature;
Sat. Saturated;
SGC Silica gel chromatography;
SM Starting material;
TCL Thin layer chromatography;
TEA Triethylamine;
TFA Trifluoroacetic acid; and
THF Tetrahydrofuran.

The following examples provide the details about the synthesis, activities, and applications of the compounds of the present disclosure. It should be understood the following is representative only, and that the invention is not limited by the details set forth in these examples.

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention.

The compounds of the present disclosure are prepared using the reactions and techniques described below, together with conventional techniques known to those skilled in the art of organic synthesis, or variations thereon as appreciated by those skilled in the art.

The reactions are performed in solvents appropriate to the reagents and materials employed and are suitable for the transformations being affected. Preferred methods include, but not limited to those described below, where all symbols are as defined earlier and otherwise defined below.

Example 1

General Procedures for the Synthesis of Compounds Disclosed in Formula (I):

The compounds of Formula (I) is prepared following independent general synthetic routes as outlined in the Schemes below:

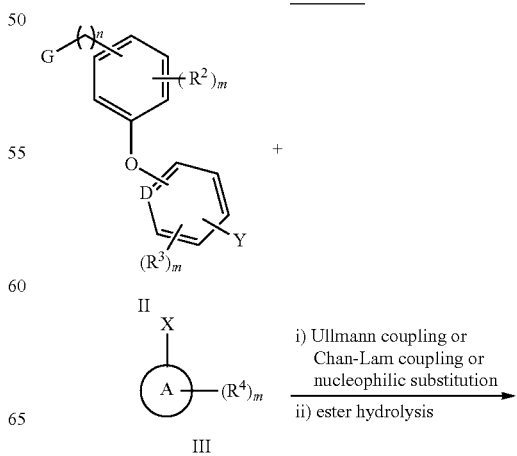

Scheme-1

-continued

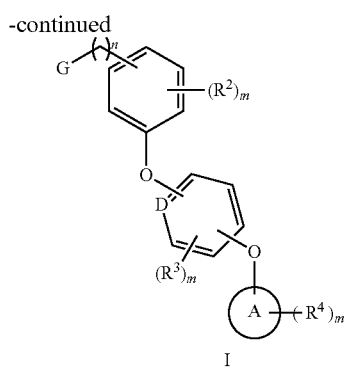

I

Y, X=I, Br, Cl, OH, OTs, Boronate, Boronic acid, etc

General synthetic route (1) for the preparation of compounds of Formula (I): Compounds of Formula (I) may be prepared from intermediate (II) and (III) using step (i) as Ullmann coupling reaction or Chan Lam coupling reaction or nucleophilic aromatic substitution reaction or Suzuki reaction or any other coupling reaction mediated by transition metal by selecting appropriate coupling partners followed by step (ii) as ester hydrolysis (If $R_1$ is —OMe or —OEt) as shown in Scheme-1, wherein Y can be halogen or —OTf or boronate ester or boronic acid and Y≠X.

General synthetic route (2) for the preparation of compounds of Formula (I):

Scheme-1a

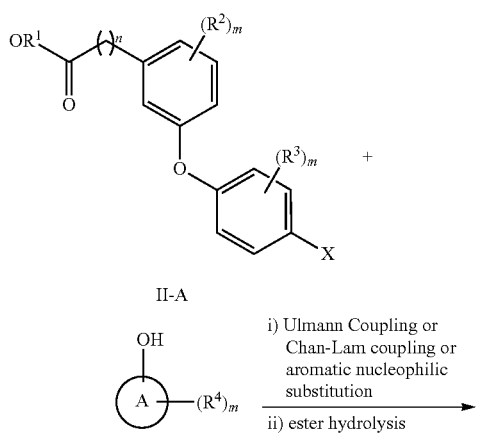

I

Compounds of Formula (I) may be prepared from intermediate (II-A) and (III-A) using Ullmann coupling reaction or Chan-Lam coupling reaction or nucleophilic aromatic substitution reaction followed by ester hydrolysis (If $R_1$ is —OMe or —OEt) as shown in scheme-1, wherein X can be halogen or —OTf or boronate ester or boronic acid.

General synthetic route (3) for the preparation of compounds of Formula (I):

Scheme-1b

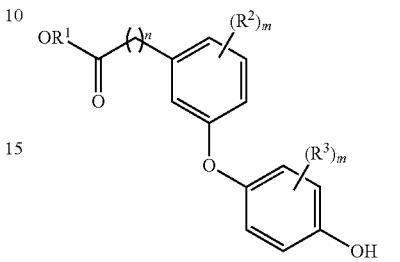

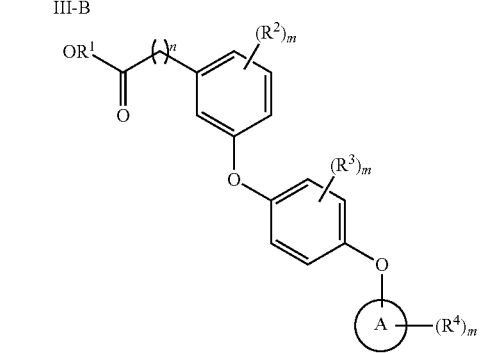

I

Alternatively, compounds of Formula (I) may be prepared from intermediate (II-B) and (III-B) using Ullmann coupling reaction or nucleophilic aromatic substitution reaction followed by ester hydrolysis (If $R_1$ is —OMe or —OEt) as shown in scheme-2 wherein X can be halogen or —OTf or boronate ester or boronic acid.

Scheme-2
General preparation of compound having Formula (II-A) and (II-B)

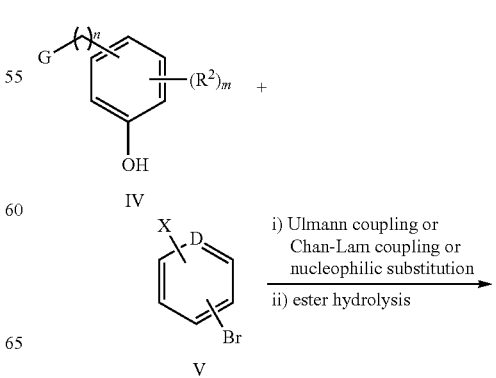

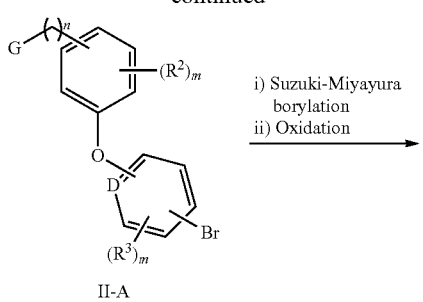

II-A

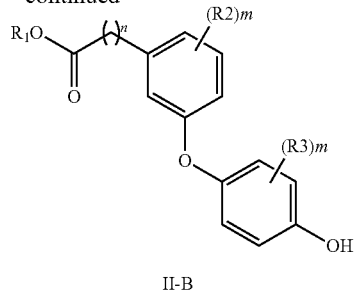

II-B

Intermediates of general Formula II-A may be prepared from IV and V using Ullmann coupling or Chan-Lam coupling or nucleophilic aromatic substitution reaction wherein X can be halogen (Br, I, F) or OTf or boronate ester or boronic acid. Intermediate II-B may be prepared from II-A using Suzuki-Miyaura borylation followed by oxidation.

Example 2

Synthesis of Intermediates II-A and II-B

Synthesis of methyl 2-[3-[4-bromo-2-(trifluoromethyl)phenoxy]phenyl]acetate (II-A-1) and methyl 2-[3-[4-hydroxy-2-(trifluoromethyl)phenoxy]phenyl]acetate (II-B-1)

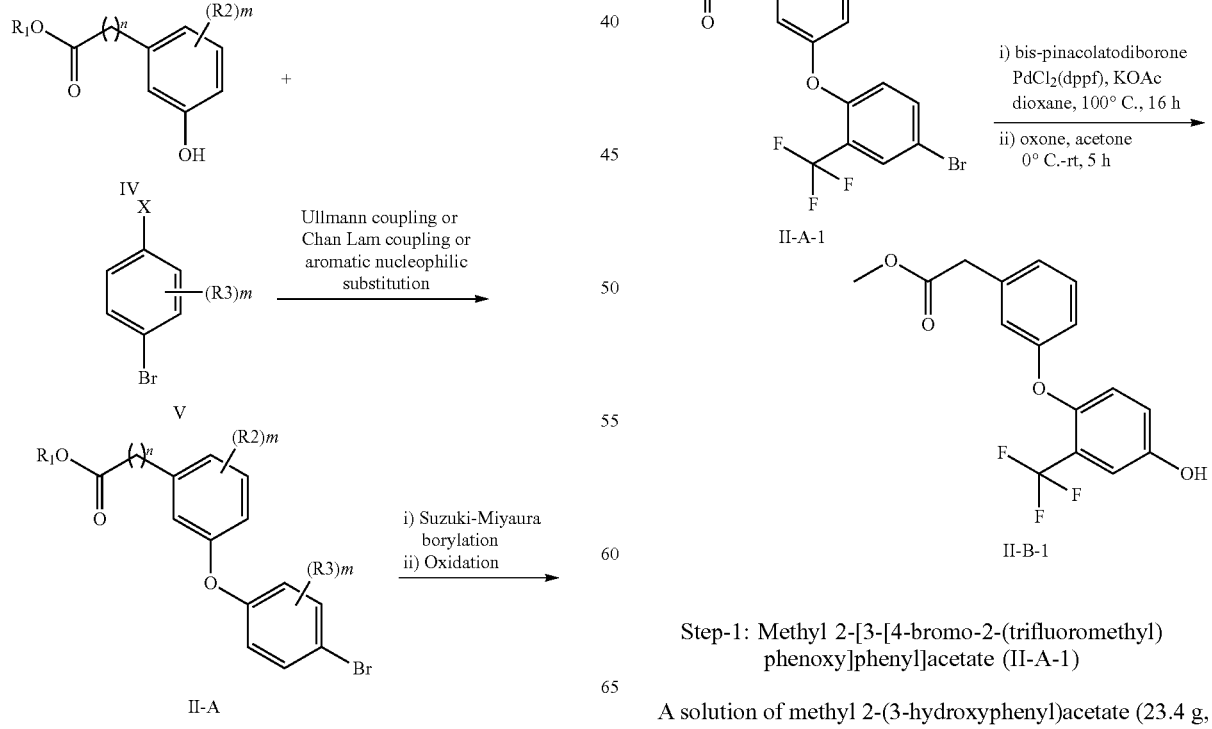

Step-1: Methyl 2-[3-[4-bromo-2-(trifluoromethyl)phenoxy]phenyl]acetate (II-A-1)

A solution of methyl 2-(3-hydroxyphenyl)acetate (23.4 g, 141 mmol), 5-bromo-2-fluorobenzotrifluoride (44.5 g, 183.3

Intermediates of general Formula II-A may be prepared from IV and V using Ullmann coupling or Chan-Lam coupling or nucleophilic aromatic substitution reaction wherein X can be halogen (Br, I, F) or OTf or boronate ester or boronic acid. Intermediate II-B may be prepared from II-A using Suzuki-Miyaura borylation followed by oxidation.

Scheme-2a Preparation of compound having Formula (II-A) and (II-B)

mmol) and cesium carbonate (91.9 g, 282 mmol) in DMF (250 mL) was stirred at 100° C. for 5-7 h. After completion of the reaction, it was cooled to room temperature and diluted using water (1 l). Extraction was carried out using EtOAc (300 mL×3); the combined organic layers were washed with water (500 mL×3); brine (500 mL); dried over anhydrous $Na_2SO_4$, filtered and concentrated under reduced pressure. The residue obtained was purified using silica gel column chromatography (product eluted using 5-10% EtOAc in hexane) to provide desired intermediate II-A-1 (30 g, 55% yield). $^1$H NMR (DMSO-$d_6$; 400 MHz) 3.62 (s, 3H); 3.72 (s, 2H); 6.95-7.01 (aromatics, 2H); 7.02-7.06 (aromatics, 1H); 7.14 (d, J=8.0 Hz, 1H); 7.37-7.41 (aromatics, 1H); 7.84 (dd, $J_1$=2.7 Hz, $J_2$=9.2 Hz, 1H); 7.95 (d, J=2.7 Hz, 1H).

Step-2: Methyl 2-[3-[4-hydroxy-2-(trifluoromethyl) phenoxy]phenyl]acetate (II-B-1)

Argon was purged through a solution of intermediate II-A-1 (15 g, 38.6 mmol), (bis-pinacolato)diboron (11.4 g, 57.9 mmol), KOAc (7.57 g, 77.1 mmol) and $PdCl_2$(dppf)-$CH_2Cl_2$ (1.57 g, 19.3 mmol) in anhydrous 1,4-dioxane (160 mL) for 30 min. It was then stirred at 100° C. for 16 h. After completion of the reaction, it was filtered through celite and dioxane was removed under reduced pressure. The residue obtained was diluted using EtOAc (600 mL) and it was washed using water (300 mL); brine (300 mL); dried over anhydrous $Na_2SO_4$, filtered and concentrated under reduced pressure. The residue obtained was purified using silica gel column chromatography to provide corresponding boronate ester (20 g) [$^1$H NMR (DMSO-$d_6$; 400 MHz) 1.31 (s, 12H); 3.62 (s, 3H); 3.73 (s, 2H); 6.97 (d, J=8.4 Hz, 1H); 6.99-7.02 (aromatics, 1H); 7.03-7.06 (aromatics, 1H); 7.16 (d, J=7.6 Hz, 1H); 7.38-7.42 (aromatics, 1H); 7.88-7.91 (aromatics, 1H); 7.93 (s, 1H)]. Two such batches of boronate ester were combined and subjected to oxidation using oxone. The boronate ester intermediate (~40 g) was dissolved in acetone-water (1:1, 240 mL) and oxone (21.4 g, 141 mmol) was added to it portion wise at room temperature. After stirring for 2 h, acetone was removed under reduced pressure. The residue obtained was dissolved in EtOAc (700 mL) and it was washed using water (500 mL); brine (500 mL); dried over anhydrous $Na_2SO_4$, filtered and concentrated under reduced pressure. The residue obtained was purified using silica gel column chromatography (10-20% EtOAc in hexane) to provide desired intermediate II-B-1 (20 g, 65%). $^1$H NMR (DMSO-$d_6$; 400 MHz) 3.62 (s, 3H); 3.67 (s, 2H); 6.79 (dd, $J_1$=1.9 Hz, $J_2$=8.3 Hz, 1H); 6.86-6.92 (aromatics, 2H); 6.97-7.06 (aromatics, 2H); 7.05 (dd, $J_1$=3.0 Hz, $J_2$=8.6 Hz, 1H); 7.10 (d, J=2.9 Hz, 1H); 7.27-7.31 (aromatics, 1H); 10.00 (bs, 1H).

Following intermediates were synthesized using similar experimental procedures as described for II-A-1 and II-B-1.

| No. | Structure & IUPAC name | Analytical Data |
|---|---|---|
| II-A-2 | 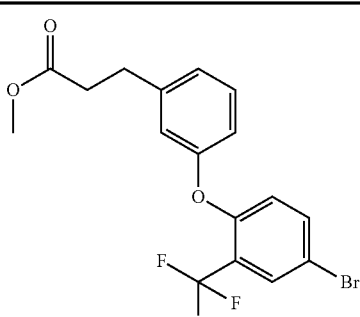<br>Methyl 3-[3-[4-bromo-2-(trifluoromethyl)phenoxy]phenyl]propanoate | $^1$H NMR (CDCl$_3$; 400 MHz) 2.62 (t, J = 7.8 Hz, 2H); 2.95 (t, J = 8.3 Hz, 2H); 3.66 (s, 3H); 6.79 (d, J = 9.0 Hz, 1H); 6.84-6.89 (aromatics, 2H); 7.02 (d, J = 7.8 Hz, 1H); 2.28-7.31 (aromatics, 1H); 7.54 (dd, $J_1$ = 2.8 Hz, $J_2$ = 8.6 Hz, 1H), 7.78 (dd, J = 2.4 Hz, 1H). |
| II-A-3 | 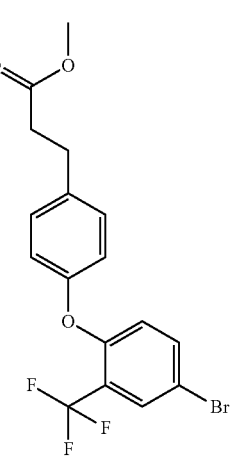<br>Methyl 3-[4-[4-bromo-2-(trifluoromethyl)phenoxy] phenyl]propanoate | $^1$H NMR (CDCl$_3$; 400 MHz) 2.63 (t, J = 7.4 Hz, 2H); 2.95 (t, J = 7.8 Hz, 2H); 3.68 (s, 3H); 6.78 (d, J = 8.8 Hz, 1H); 6.94-6.97 (aromatics, 2H); 7.19-7.21 (aromatics, 2H); 7.50-7.51 (aromatics, 1H); 7.77 (d, J = 2.5 Hz, 1H). |

| No. | Structure & IUPAC name | Analytical Data |
|---|---|---|
| II-B-2 | 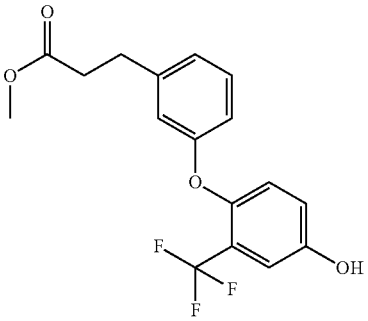

Methyl 3-[3-[4-hydroxy-2-(trifluoromethyl)phenoxy]phenyl]propanoate | $^1$H NMR (DMSO-$d_6$; 400 MHz) 2.60 (t, J = 7.3 Hz, 2H); 2.82 (t, J = 7.9 Hz, 2H); 3.56 (s, 3H); 6.71 (dd, $J_1$ = 1.9 Hz, $J_2$ = 7.8 Hz, 1H); 6.79-6.81 (aromatics, 1H); 6.95-6.97 (aromatics, 2H); 7.02-7.09 (aromatics, 2H); 7.23-7.27 (aromatics, 1H); 9.97 (bs, 1H). |
| II-B-3 | 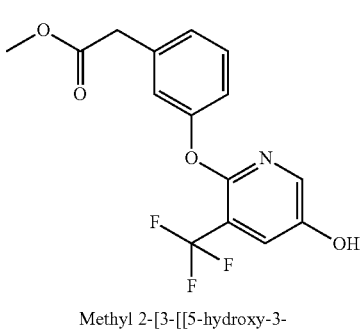

Methyl 2-[3-[[5-hydroxy-3-(trifluoromethyl)-2-pyridyl]oxy]phenyl]acetate | LCMS: m/z; 327.9 (M + 1)$^+$. $^1$H NMR (DMSO-$d_6$; 400 MHz) 3.63 (s, 2H); 3.70 (s, 3H); 7.01 (dd, $J_1$ = 2.0 Hz, $J_2$ = 8.6 Hz, 1H); 7.04-7.06 (aromatics, 1H); 7.10 (d, J = 7.6 Hz, 1H); 7.30-7.34 (aromatics, 1H); 7.49 (d, J = 2.7 Hz, 1H); 7.86 (d, J = 2.7 Hz, 1H). |

Synthesis of methyl 2-[3-(2-cyclopropyl-4-hydroxy-phenoxy)phenyl]acetate (II-B-4)

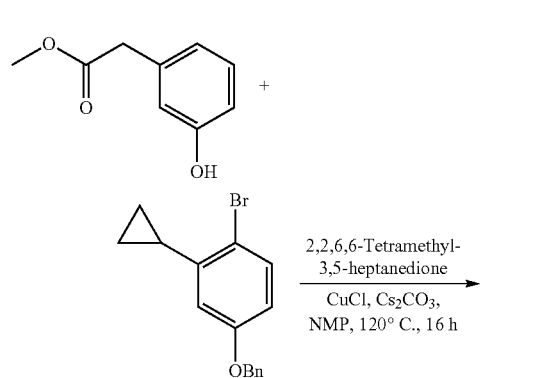

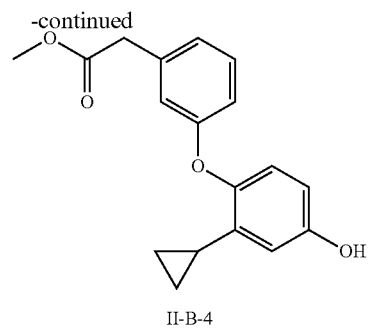

II-B-4

Synthesis of methyl 2-[3-(4-benzyloxy-2-cyclopropyl-phenoxy)phenyl]acetate (II-B-4a)

Argon was purged through a solution of methyl 2-(3-hydroxyphenyl)acetate (2 g, 12 mmol), 4-benzyloxy-1-bromo-2-cyclopropyl-benzene (4.7 g, 15.5 mmol) and Cs$_2$CO$_3$ (7.1 g, 22 mmol) in NMP (20 mL) for 15 min. CuCl (1.63 g, 16.5 mmol) and 2,2,6,6-tetramethyl-3,5-heptanedione (2.5 mL, 12 mmol) were added to the reaction mixture and purging was continued for 15 min more. The reaction mixture was then stirred at 120° C. for 24 h. Finally, it was cooled to room temperature and diluted using water (100 mL). Extraction was carried out using EtOAc (100 mL×3); the combined organic layers were washed with water (150 mL); brine (150 mL); dried over anhydrous Na$_2$SO$_4$, filtered and concentrated under reduced pressure. The residue obtained was purified using silica gel column chromatography to provide desired intermediate II-B-4a (0.9 g, 19% yield). ¹H NMR (DMSO-d₆; 400 MHz) 0.64-0.68 (m, 2H); 0.78-0.84 (m, 2H); 1.85-1.92 (m, 1H); 3.60 (s, 3H); 3.64 (s, 2H); 5.07 (s, 2H); 6.57 (d, J=2.9 Hz, 1H); 6.72 (dd, J₁=2.4 Hz, J₂=8.3 Hz, 1H); 6.77-6.80 (aromatics, 1H); 6.83 (dd, J₁=3.0 Hz, J₂=8.8 Hz, 1H); 6.91 (d, J=8.8 Hz, 2H); 7.22-7.27 (aromatics, 1H); 7.32-7.47 (aromatics, 5H).

Synthesis of methyl 2-[3-(2-cyclopropyl-4-hydroxyphenoxy)phenyl]acetate (II-B-4)

Intermediate II-B-4a (0.85 g) was dissolved in MeOH, to which 10% Pd/C (0.08 g) was added. The reaction mixture was stirred under H₂ atmosphere (bladder pressure) for 5 h. After completion of the reaction, it was filtered through celite and washed with MeOH. The combined organic layers were removed under reduced pressure and the residue was purified using silica gel column chromatography to provide desired intermediate II-B-4 (0.4 g, 61% yield). ¹H NMR (DMSO-d₆; 400 MHz) 0.54-0.58 (m, 2H); 0.76-0.81 (m, 2H); 1.80-1.86 (m, 1H); 3.59 (s, 3H); 3.63 (s, 2H); 6.31 (d, J=2.9 Hz, 1H); 6.57 (dd, J₁=2.5 Hz, J₂=8.8 Hz, 1H); 6.69 (dd, J₁=1.9 Hz, J₂=8.3 Hz, 1H); 6.75-6.80 (aromatics, 2H); 6.88 (d, J=7.3 Hz, 1H); 7.20-7.25 (aromatics, 1H); 9.25 (s, 1H).

Synthesis of methyl 2-[3-[2-(difluoromethyl)-4-hydroxy-phenoxy]phenyl]acetate (II-B-5)

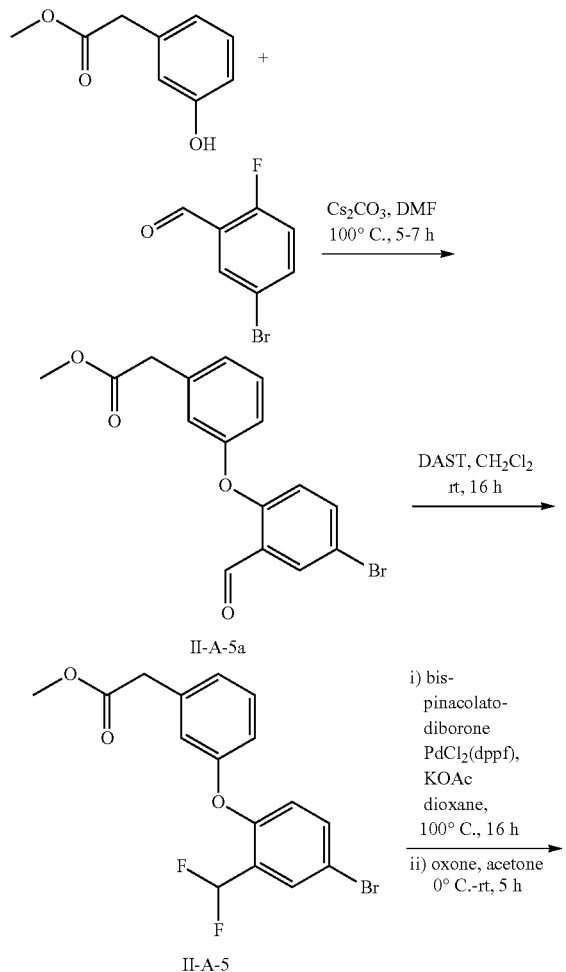

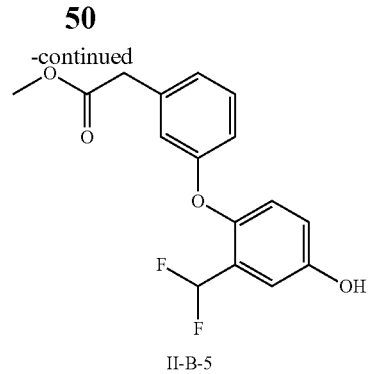

Step-1: Synthesis of methyl 2-[3-(4-bromo-2-formyl-phenoxy)phenyl]acetate (II-A-5a)

II-A-5a (1.5 g, 9% yield) was synthesized using methyl 2-(3-hydroxyphenyl)acetate (8 g) and 5-bromo-2-fluorobenzaldehyde (7.8 g), following procedure as described for the synthesis of II-A-1. ¹H NMR (DMSO-d₆; 400 MHz) 3.61 (s, 3H); 3.73 (s, 2H); 6.91 (d, J=8.8 Hz, 1H); 7.07 (dd, J₁=2.4 Hz, J₂=8.3 Hz, 1H); 7.09-7.11 (aromatics, 1H); 7.15 (d, J=7.8 Hz, 1H); 7.38-7.43 (aromatics, 1H); 7.83 (dd, J₁=2.9 Hz, J₂=8.8 Hz, 1H); 7.91 (d, J=2.4 Hz, 1H); 10.32 (s, 1H).

Step-2: Synthesis of methyl 2-[3-[4-bromo-2-(difluoromethyl)phenoxy]phenyl]acetate (II-A-5)

To a solution of II-A-5a (1.5 g, 4.3 mmol) in anhydrous CH₂Cl₂ (15 mL) was added DAST (1.3 g, 8.3 mmol) and the reaction mixture was stirred at room temperature for 16 h. After completion of the reaction, volatiles were removed under reduced pressure and it was diluted using water (30 mL). Extraction was carried out using EtOAc (30 mL×3); the combined organic layers were washed with saturated NaHCO₃ solution (50 mL); brine (50 mL); dried over anhydrous Na₂SO₄, filtered and concentrated under reduced pressure. The residue obtained was purified using silica gel column chromatography (0-20% EtOAc in hexane) to provide desired intermediate II-A-5 (1.5 g, 94% yield). ¹H NMR (DMSO-d₆; 400 MHz) 3.61 (s, 3H); 3.72 (s, 2H); 6.87 (d, J=8.8 Hz, 1H); 6.98 (dd, J₁=2.5 Hz, J₂=8.3 Hz, 1H); 7.02-7.04 (aromatics, 1H); 7.12 (d, J=7.3 Hz, 1H); 7.21 (t, J=54.3 Hz, 1H); 7.36-7.40 (aromatics, 1H); 7.71 (dd, J₁=1.9 Hz, J₂=8.8 Hz, 1H); 7.80 (d, J=2.4 Hz, 1H).

Step-3, 4: Synthesis of methyl 2-[3-[2-(difluoromethyl)-4-hydroxy-phenoxy]phenyl]acetate (II-B-5)

II-B-5 (0.9 g, 72% yield) was synthesized using II-A-5 (1.5 g) following procedure as described for the synthesis of II-B-1. ¹H NMR (DMSO-d₆; 400 MHz) 3.60 (s, 3H); 3.67 (s, 2H); 6.78 (dd, J₁=2.4 Hz, J₂=8.3 Hz, 1H); 6.84-7.02 (aromatics, 5H); 7.00 (t, J=55.2 Hz, 1H); 7.26-7.31 (aromatics, 1H); 9.78 (s, 1H).

Synthesis of 5-bromo-8-chloro-phthalazine (III-B-1)

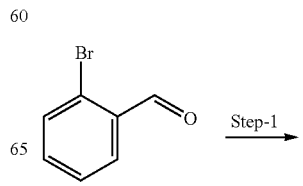

-continued

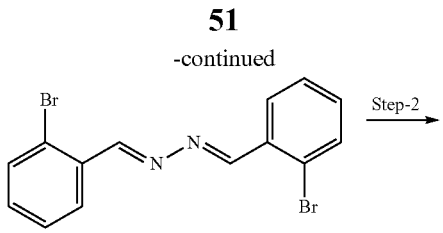

III-B-1a

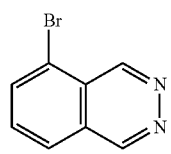

III-B-1

Step-1: 1-(2-bromophenyl)-N—[(E)-(2-bromophenyl)methyleneamino]methanimine (III-B-1a)

A solution of 2-bromobenzaldehyde (4.9 mL, 40 mmol) and hydrazine-hydrate (1 mL, 20 mmol) in MeOH (100 mL) was stirred at 80° C. for 3 h. It was then cooled to room temperature and the precipitated solid was filtered. It was washed with MeOH (10 mL×2) and dried to provide desired intermediate III-B-1a (4 g).LCMS: m/z; 364.7 (M+1)+.

Step-2: 5-bromo-8-chloro-phthalazine (III-B-1)

III-B-1a (4 g, 10.9 mmol) and anhydrous $AlCl_3$ (28.9 g, 217 mmol) were stirred at 200° C. for 1 h. After completion of the reaction, it was cooled to 0° C. and slowly quenched using ice (highly exothermic). An aqueous solution of 1N HCl was added to it and stirred for 10 min. It was then made alkaline using aqueous solution of 10% KOH. Extraction was carried out using EtOAc (50 mL×3), the combined organic layers were washed with water (100 mL×2), brine (100 mL), dried over anhydrous $Na_2SO_4$, filtered and concentrated under reduced pressure. The residue obtained was purified using silica gel column chromatography (0-40% EtOAc in hexane) to provide desired intermediate III-B-1 (0.4 g, 17% yield). LCMS: m/z; 208.8 (M+1)+. $^1H$ NMR (DMSO-$d_6$; 400 MHz) 7.98 (apparent t, J=8.3 Hz, 1H); 8.22-8.25 (aromatics, 1H); 8.35-8.37 (aromatics, 1H); 9.72-9.75 (aromatics, 2H).

Following intermediate was synthesized using similar experimental procedure as described for the synthesis of III-B-1.

| No. | Structure & IUPAC name | Analytical Data |
|---|---|---|
| III-B-2 | 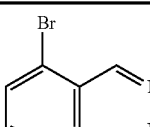 5-bromo-8-chloro-phthalazine | LCMS: m/z; 242.9 (M + 1)+ |

Synthesis of 8-bromo-5-fluoro-isoquinoline (III-B-3)

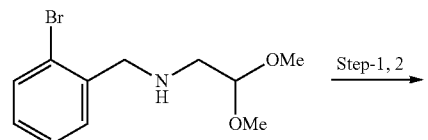

III-B-3a

III-B-3

Step-1, 2

Intermediate III-B-3a (10 g, 34 mmol) (synthesized from 2-bromo-5-fluorobenzaldehyde) was dissolved in anhydrous $CH_2Cl_2$ (100 mL); to which triethylamine (14.2 mL, 102 mmol) and p-toluenesulfonyl chloride (7.2 g, 37 mmol) were added at 0° C. The reaction mixture was monitored by TLC. After completion of the reaction, water (100 mL) was added to it and extraction was carried out using $CH_2Cl_2$ (30 mL×2). The combined organic layers were washed with water (100 mL); dried over anhydrous $Na_2SO_4$, filtered and concentrated under reduced pressure to provide desired corresponding tosyl intermediate (12 g, 81% yield), which was carried forward without any purification. A solution of corresponding tosyl intermediate (5 g, 11.2 mmol) in anhydrous $CH_2Cl_2$ (50 mL) was added slowly to a suspension of anhydrous $AlCl_3$ (7.45 g, 56 mmol) in $CH_2Cl_2$ (100 mL) at 0° C. The reaction mixture was stirred at room temperature for 24 h, before it was quenched using ice-water (100 mL). Extraction was carried out using $CH_2Cl_2$ (30 mL×2); the combined organic layers were washed with saturated $NaHCO_3$ solution (100 mL); water (100 mL); dried over anhydrous $Na_2SO_4$, filtered and concentrated under reduced pressure. The residue obtained was purified using silica gel column chromatography (0-20% EtOAc in hexane) to provide desired intermediate III-B-3 (1.2 g, 46% yield).LCMS: m/z; 226 (M+1)+. $^1H$ NMR (DMSO-$d_6$; 400 MHz) 7.61-7.66 (aromatics, 1H); 7.99 (dd, $J_1$=0.7 Hz, $J_2$=4.9 Hz, 1H); 8.03 (dd, $J_1$=4.9 Hz, $J_2$=8.3 Hz, 1H); 8.76 (d, J=5.8 Hz, 1H); 9.51 (s, 1H).

Synthesis of 6-bromo-1-(oxetan-3-yl)indazole (III-B-4) and 6-bromo-2-(oxetan-3-yl)indazole (III-B-5)

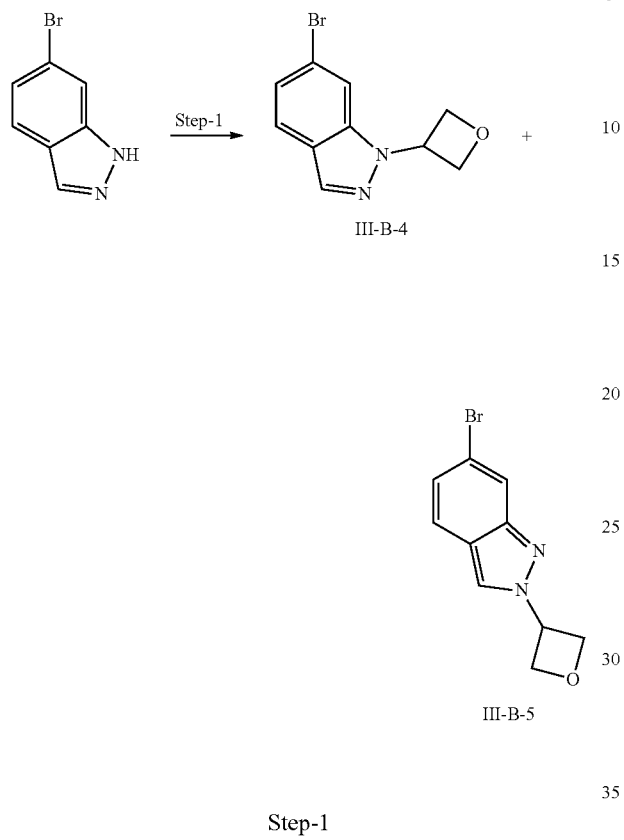

Step-1

A solution of 6-bromo-1H-indazole (2 g, 10.2 mmol), 3-bromooxetane (2.7 g, 20.4 mmol) and anhydrous $K_2CO_3$ (2.8 g, 20.4 mmol) in DMF (15 mL) was stirred at 85° C. for 16 h. It was then cooled to room temperature and diluted using water (50 mL). Extraction was carried out using EtOAc (30 mL×3); the combined organic layers were washed with water (50 mL×2); brine (50 mL); dried over anhydrous $Na_2SO_4$, filtered and concentrated under reduced pressure. The residue obtained was purified using silica gel column chromatography (0-30% EtOAc in hexane) to provide desired intermediates III-B-4 (non-polar spot) (0.6 g) and III-B-5 (polar spot) (0.6 g).

III-B-4: LCMS: m/z; 253 (M+1)+. 1H NMR (CDCl3; 400 MHz) 5.11-5.15 (m, 2H); 5.25-5.29 (m, 2H); 5.69-5.76 (m, 1H); 7.26-7.30 (aromatics, 1H); 7.61 (d, J=8.8 Hz, 1H); 7.71 (s, 1H); 8.06 (s, 1H).

III-B-5: LCMS: m/z; 253 (M+1)+. 1H NMR (CDCl3; 400 MHz) 5.14-5.21 (m, 4H); 5.66-5.73 (m, 1H); 7.19 (dd, J1=1.5 Hz, J2=8.9 Hz, 1H); 7.54 (d, J=8.8 Hz, 1H); 7.93 (s, 1H); 8.09 (s, 1H).

Following intermediates were synthesized using similar experimental procedures as described for the synthesis of III-B-4 and III-B-5.

| No. | Structure & IUPAC name | Analytical Data |
|---|---|---|
| III-B-6 | 5-bromo-1-(oxetan-3-yl)indazole | LCMS: m/z; 253 (M + 1)+. 1H NMR (CDCl3; 400 MHz) 5.12-5.16 (m, 2H); 5.25-5.30 (m, 2H); 5.72-5.79 (m, 1H); 7.42 (d, J = 8.8 Hz, 1H); 7.49 (dd, J1 = 1.4 Hz, J2 = 8.8 Hz, 1H); 7.90 (d, J = 1.5 Hz, 1H); 8.03 (s, 1H). |
| III-B-7 | 5-bromo-2-(oxetan-3-yl)indazole | LCMS: m/z; 253 (M + 1)+. 1H NMR (CDCl3; 400 MHz) 5.14-5.21 (m, 4H); 5.66-5.72 (m, 1H); 7.37 (dd, J1 = 1.9 Hz, J2 = 9.2 Hz, 1H); 7.64 (d, J = 9.3 Hz, 1H); 7.82 (d, J = 1.0 Hz, 1H); 8.05 (s, 1H). |
| III-B-8 | 6-bromo-1-(oxetan-3-yl)imidazo[4,5-b]pyridine | LCMS: m/z; 254 (M + 1)+. 1H NMR (CDCl3; 400 MHz) 4.94-4.98 (m, 2H); 5.10-5.14 (m, 2H); 5.75-5.82 (m, 1H); 8.39 (d, J = 2.0 Hz, 1H); 8.46 (d, J = 2.0 Hz, 1H); 8.75 (s, 1H). |
| III-B-9 | 6-bromo-1-(oxetan-3-yl)pyrrolo[2,3-b]pyridine | LCMS: m/z; 253 (M + 1)+. |

Synthesis of 6-bromo-1-(oxetan-3-yl)benzotriazole (III-B-10)

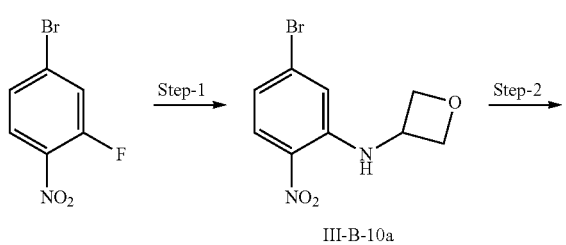

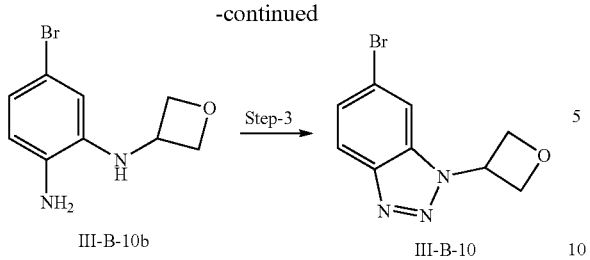

Step-1: N-(5-bromo-2-nitro-phenyl)oxetan-3-amine (III-B-10a)

To a solution of 4-bromo-2-fluoronitrobenzene (5 g, 22.8 mmol) and triethylamine (4.8 mL, 34.2 mmol) in EtOH (40 mL) was added 3-aminooxetane (2 g, 27.4 mmol) at 0° C.; and the reaction mixture was stirred at room temperature for 16 h. After completion of the reaction, volatiles were removed under reduced pressure and water (50 mL) was added. Extraction was carried out using EtOAc (50 mL×3); the combined organic layers were washed with water (50 mL×2); brine (50 mL); dried over anhydrous $Na_2SO_4$, filtered and concentrated under reduced pressure to provide desired intermediate III-B-10a (6.3 g, 91% yield). LCMS: m/z; 273 $(M+1)^+$.

Step-2: 4-bromo-N2-(oxetan-3-yl)benzene-1,2-diamine (III-B-10b)

To a solution of III-B-10a (0.4 g, 1.47 mmol) and ammonium chloride (0.39 g, 7.35 mmol) in THF:MeOH (1:1, 8 mL) was added zinc dust (0.48 g, 7.35 mmol) at 0° C.; and the reaction mixture was stirred at room temperature for 3 h. After completion of the reaction, it was filtered through celite and washed with EtOAc (10 mL×3). The combined organic layers were washed with water (30 mL×2); brine (30 mL); dried over anhydrous $Na_2SO_4$, filtered and concentrated under reduced pressure to provide desired intermediate III-B-10b (0.37 g, quantitative yield) as brown oil. LCMS: m/z; 243 $(M+1)^+$.

Step-3: 6-bromo-1-(oxetan-3-yl)benzotriazole (III-B-10)

To a solution of III-B-10b (0.4 g, 1.65 mmol) in $CH_2Cl_2$ (6 mL) was added 50% aqueous AcOH (4 mL) followed by portion wise addition of $NaNO_2$ (0.23 g, 3.3 mmol) at 0° C. The reaction mixture was stirred at 0° C. for 1 h before it was made alkaline using saturated $NaHCO_3$ solution (20 mL). Extraction was carried out using $CH_2Cl_2$ (15 mL×3); the combined organic layers were washed with water (30 mL); brine (30 mL); dried over anhydrous $Na_2SO_4$, filtered and concentrated under reduced pressure. The residue obtained was dissolved in minimum $CH_2Cl_2$. To this was added pentane, and the resultant precipitates were filtered to provide desired intermediate III-B-10 (0.37 g, 88% yield). LCMS: m/z; 254 $(M+1)^+$. $^1$H NMR ($CDCl_3$; 400 MHz) 5.27-5.29 (m, 4H); 5.98-6.05 (m, 1H); 7.52 (dd, $J_1$=1.9 Hz, $J_2$=8.8 Hz, 1H); 7.98 (d, J=8.8 Hz, 1H); 8.02 (d, J=1.4 Hz, 1H).

Synthesis of 6-bromo-1-(oxetan-3-yl)benzimidazole (III-B-11)

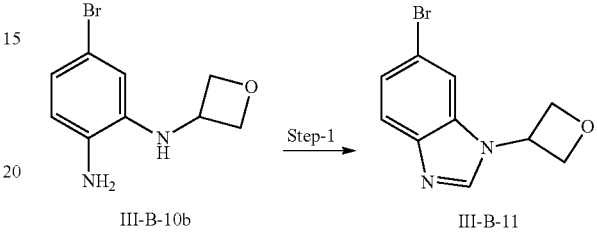

Step-1

A solution of III-B-10b (1 g, 4.1 mmol), triethylorthoformate (6.5 mL, 41 mmol) and p-toluenesulfonic acid (0.077 g, 0.41 mmol) in THF (20 mL) was stirred at 80° C. for 2 h. After completion of the reaction, it was diluted using EtOAc (30 mL). The combined organic layers were washed with saturated $NaHCO_3$ solution (30 mL); brine (30 mL); dried over anhydrous $Na_2SO_4$, filtered and concentrated under reduced pressure. The residue obtained was purified using silica gel column chromatography (0-5% MeOH in $CH_2Cl_2$) to provide desired intermediate III-B-11 (0.8 g, 77% yield). LCMS: m/z; 253 $(M+1)^+$. $^1$H NMR (DMSO-$d_6$; 400 MHz) 4.94-4.98 (m, 2H); 5.05-5.09 (m, 2H); 5.73-5.77 (m, 1H); 7.39 (dd, $J_1$=1.5 Hz, $J_2$=8.3 Hz, 1H); 7.65 (d, J=8.3 Hz, 1H); 7.98 (d, J=1.9 Hz, 1H); 8.58 (s, 1H).

Following intermediate was synthesized as described for the synthesis of III-B-11.

| No. | Structure & IUPAC name | Analytical Data |
|---|---|---|
| III-B-12 | 6-bromo-2-methyl-1-(oxetan-3-yl)benzimidazole | LCMS: m/z; 267 $(M + 1)^+$. $^1$H NMR (DMSO-$d_6$; 400 MHz) 2.52 (s, 3H); 4.96-5.00 (m, 2H); 5.08-5.13 (m, 2H); 5.61-5.68 (m, 1H); 7.35 (dd, $J_1$ = 1.6 Hz, $J_2$ = 8.4 Hz, 1H); 7.54 (d, J = 8.4 Hz, 1H); 8.07 (d, J = 1.2 Hz, 1H). |

Example A-1: Synthesis of 2-[3-[4-(8-isoquinolyloxy)-2-(trifluoromethyl)phenoxy]phenyl]acetic Acid Method-A:

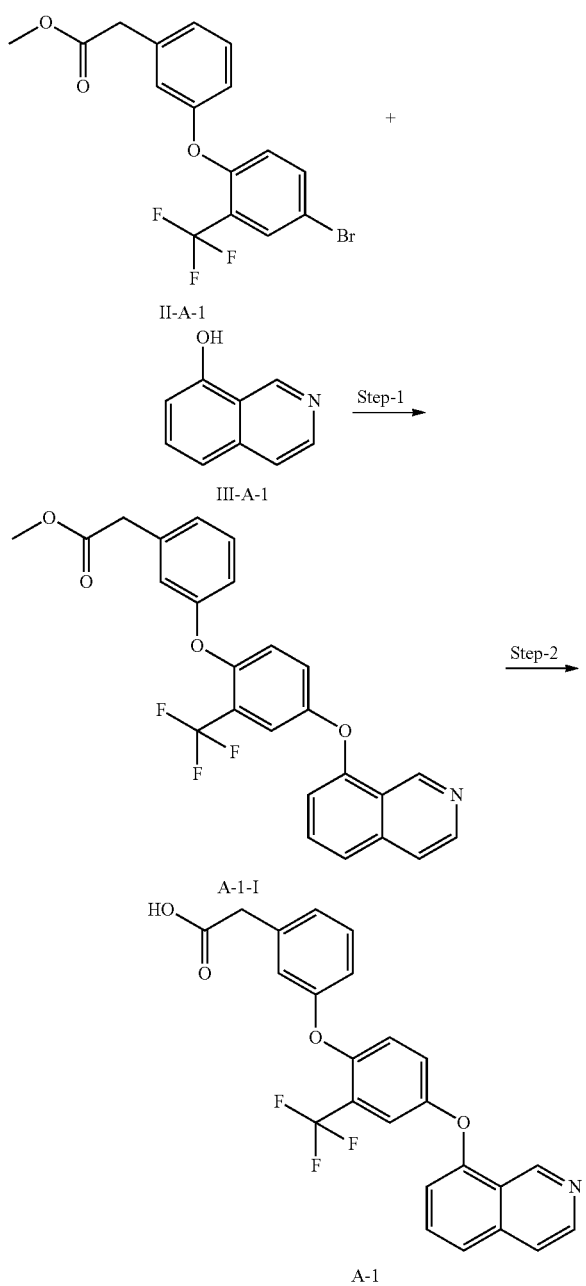

Step-1: Methyl 2-[3-[4-(8-isoquinolyloxy)-2-(trifluoromethyl)phenoxy]phenyl]acetate (A-1-I)

Argon was purged through a solution of intermediate II-A-1 (2.6 g, 6.68 mmol), 8-hydroxyisoquinoline (1.26 g, 8.68 mmol) and $Cs_2CO_3$ (4.35 g, 13.4 mmol) in 1,4-dioxane (30 mL) for 15 min. Then, CuI (0.65 g, 3.35 mmol) and N,N-dimethylglycine (1 g, 10.2 mmol) were added and purging was continued for 15 min more. It was then stirred at 120° C. for 24 h in a sealed tube. It was then cooled to room temperature and filtered through celite. 1,4-Dioxane was removed under reduced pressure and the residues were washed with EtOAc (100 mL). The combined organic layers were washed with water (50 mL); brine (50 mL); dried over anhydrous $Na_2SO_4$, filtered and concentrated under reduced pressure. The residue obtained was purified using silica gel column chromatography to provide desired intermediate A-1-I (0.39 g, 12% yield). LCMS: m/z; 453.9 $(M+1)^+$. $^1$H NMR ($CDCl_3$; 400 MHz) 3.63 (s, 2H); 3.71 (s, 3H); 6.91 (dd, $J_1$=2.5 Hz, $J_2$=6.9 Hz, 1H); 6.94 (dd, $J_1$=1.5 Hz, $J_2$=8.3 Hz, 1H); 6.99-7.02 (aromatics, 2H); 7.08 (d, J=6.9 Hz, 1H); 7.23 (dd, $J_1$=3.0 Hz, $J_2$=8.8 Hz, 1H); 7.30-7.34 (aromatics, 1H); 7.46 (d, J=2.9 Hz, 1H); 7.57-7.59 (aromatics, 2H); 7.68 (dd, $J_1$=1.0 Hz, $J_2$=5.9 Hz, 1H); 8.62 (d, J=5.9 Hz, 1H); 9.68 (s, 1H).

Step-2: 2-[3-[4-(8-isoquinolyloxy)-2-(trifluoromethyl)phenoxy]phenyl]acetic Acid (A-1)

A-1-I (0.39 g, 0.86 mmol) was dissolved in THF-MeOH (3:1, 4 mL), to which a solution of LiOH (0.1 g, 0.58 mmol) in water (1 mL) was added. After completion of the reaction, it was acidified using 10% citric acid solution (pH: 2-4) and extraction was carried out using EtOAc (30 mL×2). The combined organic layers were washed with water (30 mL); brine (30 mL); dried over anhydrous $Na_2SO_4$, filtered and concentrated under reduced pressure. The residue obtained was purified using silica gel column chromatography to provide desired compound A-1 (0.15 g, 40% yield). LCMS: m/z; 440.1 $(M+1)^+$. $^1$H NMR (DMSO-$d_6$; 400 MHz) 3.59 (s, 2H); 6.94 (dd, $J_1$=2.5 Hz, $J_2$=8.4 Hz, 1H); 7.01 (s, 1H); 7.04-7.13 (aromatics, 3H); 7.32-7.36 (aromatics, 1H); 7.46 (dd, $J_1$=2.9 Hz, $J_2$=9.3 Hz, 1H); 7.65 (d, J=2.9 Hz, 1H); 7.71-7.73 (aromatics, 2H); 7.89 (d, J=5.4 Hz, 1H); 8.59 (d, J=5.9 Hz, 1H); 9.57 (s, 1H); 12.32 (bs, 1H).

Method-B:

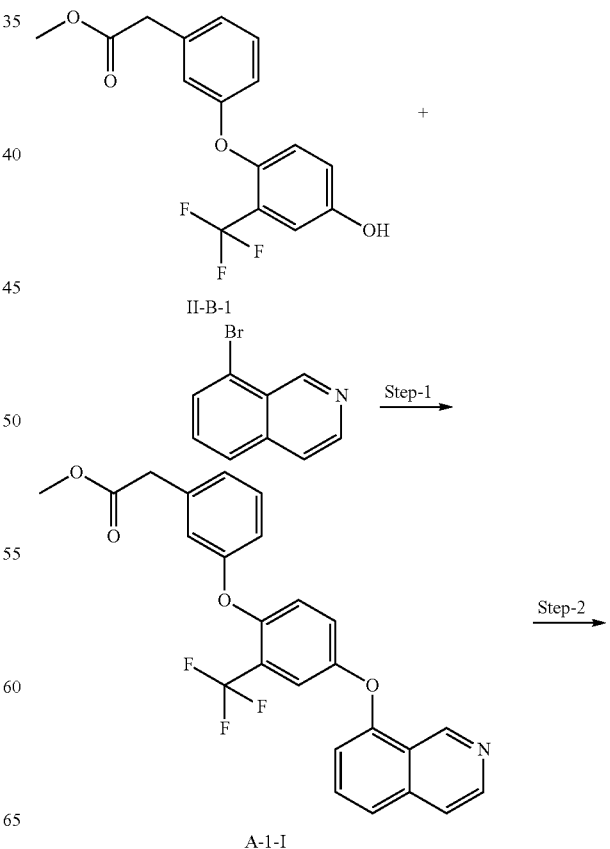

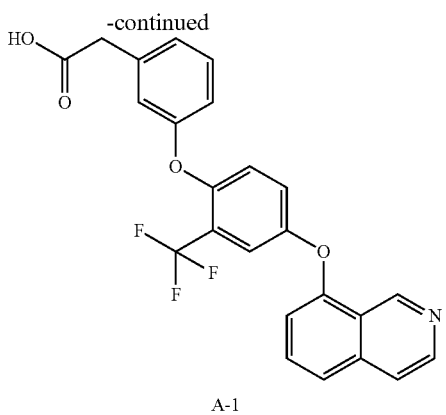

A-1

Step-1: Methyl 2-[3-[4-(8-isoquinolyloxy)-2-(trifluoromethyl)phenoxy]phenyl]acetate (A-1-I)

Argon was purged through a solution of intermediate II-B-1 (3 g, 9.2 mmol), 8-bromoisoquinoline (2.5 g, 11.9 mmol) and Cs₂CO₃ (8.9 g, 27.6 mmol) in NMP (30 mL) for 15 min. CuCl (1.36 g, 13.8 mmol) and 2,2,6,6-tetramethyl-3,5-heptanedione (1.8 mL, 9.2 mmol) were added to the reaction mixture and purging was continued for 15 min more. The reaction mixture was then stirred at 120° C. for 24 h. Finally, it was cooled to room temperature and diluted using water (150 mL). Extraction was carried out using EtOAc (100 mL×3); the combined organic layers were washed with water (150 mL); brine (150 mL); dried over anhydrous Na₂SO₄, filtered and concentrated under reduced pressure. The residue obtained was purified using silica gel column chromatography to provide desired intermediate A-1-I (2.3 g, 55% yield).

Step-2: 2-[3-[4-(8-isoquinolyloxy)-2-(trifluoromethyl)phenoxy]phenyl]acetic Acid (A-1)

As described in step-2, method-A. 2.7 g of A-1 obtained starting from 3.2 g of A-1-I.

Following compounds were synthesized following similar procedures as described for the synthesis of A-1.

| No. | Structure & IUPAC name | Method/ Intermediates used | Analytical data |
|---|---|---|---|
| A-2 | ![structure] 2-[3-[4-phthalazin-5-yloxy-2-(trifluoromethyl)phenoxy]phenyl]acetic acid | Method-B/ II-B-1 & III-B-1 (5-bromophthalazine) | LCMS: m/z; 441.1 (M + 1)⁺. ¹H NMR (DMSO-d₆; 400 MHz) 3.61 (s, 2H); 6.97 (dd, J₁ = 2.2 Hz, J₂ = 8.0 Hz, 1H); 7.04-7.06 (aromatics, 1H); 7.11 (d, J = 7.6 Hz, 1H); 7.16 (d, J = 9.0 Hz, 1H); 7.35-7.41 (aromatics, 2H); 7.54 (dd, J₁ = 3.0 Hz, J₂ = 9.1 Hz, 1H); 7.75 (d, J = 2.9 Hz, 1H); 7.90-7.98 (aromatics, 2H); 9.78 (s, 1H); 9.88 (s, 1H); 12.38 (bs, 1H). |
| A-3 | ![structure] 3-[3-[4-phthalazin-5-yloxy-2-(trifluoromethyl)phenoxy]phenyl]propanoic acid | Method-B/ II-B-2 & III-B-1 (5-bromophthalazine) | LCMS: m/z; 455.2 (M + 1)⁺. ¹H NMR (DMSO-d₆; 400 MHz) 2.55 (t, J = 7.1 Hz, 2H); 2.84 (t, J = 7.3 Hz, 2H); 6.90 (d, J = 7.8 Hz, 1H); 7.02 (bs, 1H); 7.09 (d, J = 8.3 Hz, 1H); 7.14 (d, J = 8.8 Hz, 1H); 7.32-7.36 (aromatics, 1H); 7.40 (d, J = 7.6 Hz, 1H); 7.53 (d, J = 8.8 Hz, 1H); 7.73 (bs, 1H); 7.90-8.00 (aromatics, 2H); 9.78 (s, 1H); 9.94 (s, 1H); 12.18 (bs, 1H). |

| No. | Structure & IUPAC name | Method/ Intermediates used | Analytical data |
|---|---|---|---|
| A-4 | 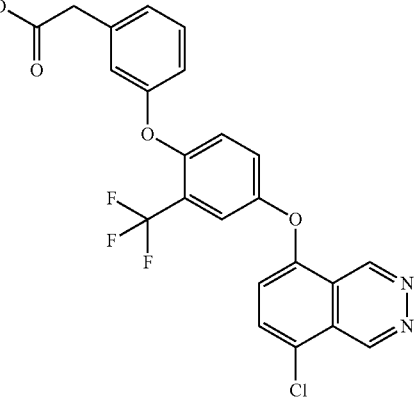<br>2-[3-[4-(8-chlorophthalazin-5-yl)oxy-2-(trifluoromethyl)phenoxy]phenyl]acetic acid | Method-B/ II-B-1 & III-B-2 (5-bromo-8-chloro-phthalazine) | LCMS: m/z; 475.1 $(M + 1)^+$. $^1$H NMR (DMSO-$d_6$; 400 MHz) 3.59 (s, 2H); 6.96 (dd, $J_1$ = 2.5 Hz, $J_2$ = 7.6 Hz, 1H); 7.03-7.60 (aromatics, 1H); 7.11 (d, J = 7.4 Hz, 1H); 7.17 (d, J = 8.8 Hz, 1H); 7.35-7.40 (aromatics, 2H); 7.58 (dd, $J_1$ = 2.9 Hz, $J_2$ = 9.0 Hz, 1H); 7.78 (d, J = 2.9 Hz, 1H); 8.07 (d, J = 8.6 Hz, 1H); 9.86 (s, 1H); 9.98 (s, 1H). |
| A-5 | 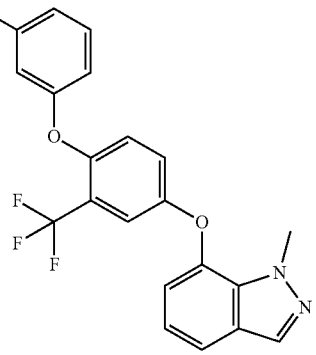<br>2-[3-[4-(1-methylindazol-7-yl)oxy-2-(trifluoromethyl)phenoxy]phenyl]acetic acid | Method-B/ II-B-1 & 7-bromo-1-methyl-1H-indazole | LCMS: m/z; 443 $(M + 1)^+$. $^1$H NMR (DMSO-$d_6$; 400 MHz) 3.60 (s, 2H); 4.16 (s, 3H); 6.89-6.94 (aromatics, 2H); 7.00-7.04 (aromatics, 1H); 7.06-7.14 (aromatics, 3H); 7.33-7.38 (aromatics, 2H); 7.55-7.58 (aromatics, 2H); 8.11 (s, 1H); 12.38 (bs, 1H). |
| A-6 | 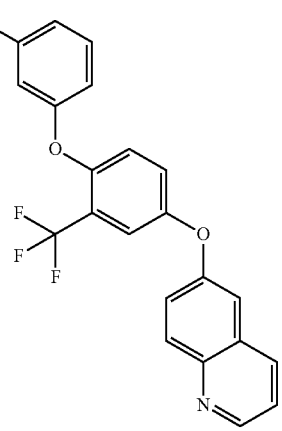<br>2-[3-[4-(6-quinolyloxy)-2-(trifluoromethyl)phenoxy]phenyl]acetic acid | Method-B/ II-B-1 & 6-bromoquinoline | LCMS: m/z; 440.1 $(M + 1)^+$. $^1$H NMR (DMSO-$d_6$; 400 MHz) 3.61 (s, 2H); 6.94 (dd, $J_1$ = 1.7 Hz, $J_2$ = 7.6 Hz, 1H); 7.02 (s, 1H); 7.09-7.14 (aromatics, 2H); 7.34-7.39 (aromatics, 1H); 7.43 (dd, $J_1$ = 2.9 Hz, $J_2$ = 9.1 Hz, 1H); 7.51-7.56 (aromatics, 3H); 7.60 (dd, $J_1$ = 2.7 Hz, $J_2$ = 9.3 Hz, 1H); 8.08 (d, J = 9.3 Hz, 1H); 8.32 (d, J = 8.1 Hz, 1H); 8.84 (dd, $J_1$ = 1.7 Hz, $J_2$ = 4.2 Hz, 1H); 12.25 (bs, 1H). |

-continued

| No. | Structure & IUPAC name | Method/ Intermediates used | Analytical data |
|---|---|---|---|
| A-7 | 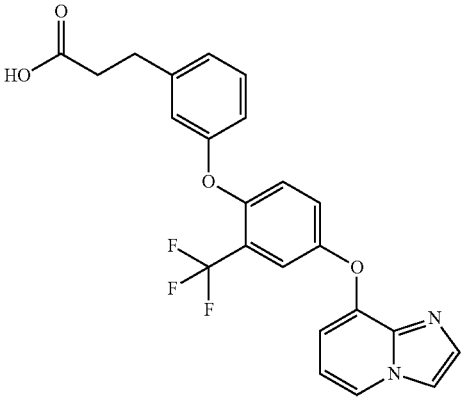<br>3-[3-[4-imidazo[1,2-a]pyridin-8-yloxy-2-(trifluoromethyl)phenoxy] phenyl]propanoic acid | Method-A/ II-A-2 & imidazo[1,2-a]pyridin-8-ol | LCMS: m/z; 443.2 (M + 1)$^+$. $^1$H NMR (DMSO-d$_6$; 400 MHz) 2.53 (t, J = 7.6 Hz, 2H); 2.82 (t, J = 7.6 Hz, 2H); 6.82-6.87 (aromatics, 3H); 6.96-6.98 (aromatics, 1H); 7.04-7.08 (aromatics, 2H); 7.29-7.34 (aromatics, 2H); 7.47 (d, J = 2.9 Hz, 1H); 7.55 (d, J = 0.7 Hz, 1H); 8.04 (d, J = 1.2 Hz, 1H); 8.42 (dd, J$_1$ = 2.9 Hz, J$_2$ = 4.6 Hz, 1H); 12.18 (bs, 1H). |
| A-8 | 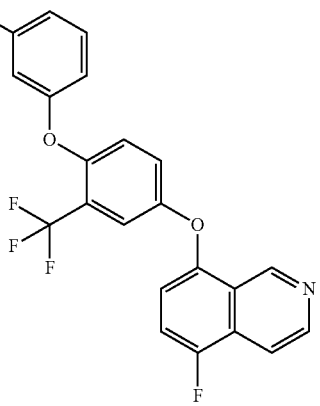<br>2-[3-[(5-fluoro-8-isoquinolyl)oxy]-2-(trifluoromethyl)phenoxy] phenyl]acetic acid | Method-B/ II-B-1 & III-B-3 (8-bromo-5-fluoro-isoquinoline) | LCMS: m/z; 458.1 (M + 1)$^+$. $^1$H NMR (DMSO-d$_6$; 400 MHz) 3.57 (s, 2H); 6.93 (dd, J$_1$ = 2.1 Hz, J$_2$ = 7.0 Hz, 1H); 7.00-7.02 (aromatics, 1H); 7.08-7.16 (aromatics, 3H); 7.35-7.38 (aromatics, 1H); 7.45 (dd, J$_1$ = 2.9 Hz, J$_2$ = 8.8 Hz, 1H); 7.59 (dd, J$_1$ = 8.5 Hz, J$_2$ = 10.1 Hz, 1H); 7.65 (d, J = 2.7 Hz, 1H); 7.97 (d, J = 5.9 Hz, 1H); 8.73 (d, J = 5.9 Hz, 1H); 9.58 (s, 1H). |
| A-9 | 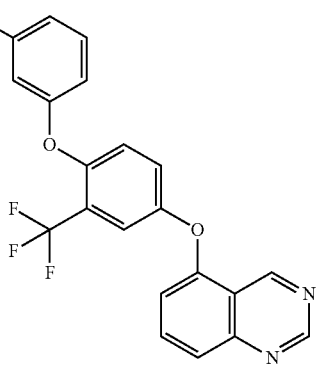<br>2-[3-[4-quinazolin-5-yloxy-2-(trifluoromethyl)phenoxy] phenyl]acetic acid | Method-B/ II-B-1 & 5-bromoquinazoline | LCMS: m/z; 441.1 (M + 1)$^+$. $^1$H NMR (DMSO-d$_6$; 400 MHz) 3.60 (s, 2H); 6.96 (dd, J$_1$ = 2.0 Hz, J$_2$ = 8.1 Hz, 1H); 7.02-7.05 (aromatics, 1H); 7.08-7.12 (aromatics, 2H); 7.16 (d, J = 9.0 Hz, 1H); 7.34-7.39 (aromatics, 1H); 7.55 (dd, J$_1$ = 3.0 Hz, J$_2$ = 9.1 Hz 1H); 7.74 (d, J = 2.7 Hz, 1H); 7.78 (d, J = 8.6 Hz, 1H); 7.93-7.97 (aromatics, 1H); 9.40 (s, 1H); 9.82 (s, 1H). |

| No. | Structure & IUPAC name | Method/ Intermediates used | Analytical data |
|---|---|---|---|
| A-10 | 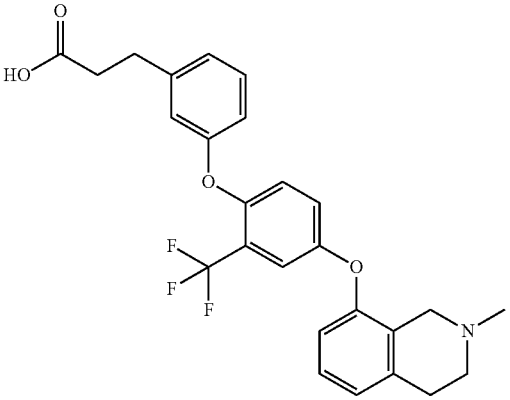<br>3-[3-[4-[(2-methyl-3,4-dihydro-1H-isoquinolin-8-yl)oxy]-2-(trifluoromethyl)phenoxy]phenyl]propanoic acid | Method-B/ II-B-2 & 8-bromo-2-methyl-1,2,3,4-tetrahydroisoquinoline | Note: Ulmann coupling using CuI $K_3PO_4$, picolinic acid in DMSO LCMS: m/z; 472.2 (M + 1)$^+$. $^1$H NMR (DMSO-$d_6$; 400 MHz) 2.33-2.42 (m, 2H); 2.59 (t, J = 5.8 Hz, 2H); 2.78 (t, J = 7.3 Hz, 2H); 2.87 (t, J = 5.4 Hz, 2H); 3.44 (s, 2H); 6.75 (d, J = 8.3 Hz, 1H); 7.79 (dd, $J_1$ = 2.0 Hz, $J_2$ = 8.3 Hz, 1H); 6.93 (bs, 1H); 6.98 (d, J = 7.3 Hz, 1H); 7.02-7.07 (aromatics, 2H); 7.15-7.20 (aromatics, 2H); 7.26-7.32 (aromatics, 2H). |
| A-11 | 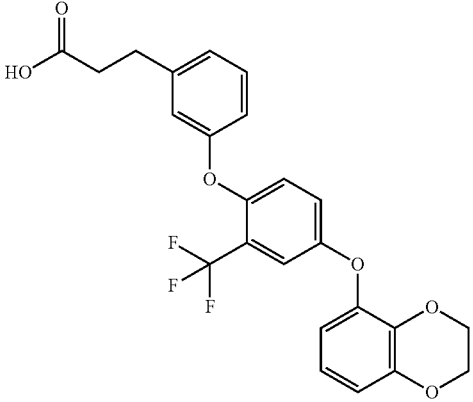<br>3-[3-[4-(2,3-dihydro-1,4-benzodioxin-5-yloxy)-2-(trifluoromethyl)phenoxy]phenyl]propanoic acid | Method-B/ II-B-2 & 5-bromo-2,3-dihydro-1,4-benzodioxine | LCMS: m/z; 461.1 (M + 1)$^+$. $^1$H NMR (DMSO-$d_6$; 400 MHz) 4.19-4.28 (m, 4H); 6.68 (dd, $J_1$ = 1.4 Hz, $J_2$ = 7.8 Hz, 1H); 6.77-6.81 (aromatics, 2H); 6.83-6.88 (aromatics, 1H); 6.92-6.94 (aromatics, 1H); 7.02-7.06 (aromatics, 2H); 7.15 (dd, $J_1$ = 3.4 Hz, $J_2$ = 9.3 Hz, 1H); 7.25-7.31 (aromatics, 2H); 12.11 (bs, 1H). |
| A-12 | 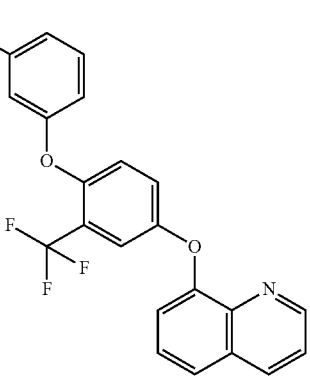<br>3-[3-[4-(8-quinolyloxy)-2-(trifluoromethyl)phenoxy]phenyl]propanoic acid | Method-A/ II-A-2 & 8-hydroxyquinoline | LCMS: m/z; 454.1 (M + 1)$^+$. $^1$H NMR (DMSO-$d_6$; 400 MHz) 2.52-2.57 (m, 2H); 2.82 (t, J = 7.3 Hz, 2H); 6.80 (dd, $J_1$ = 2.4 Hz, $J_2$ = 8.3 Hz, 1H); 6.94-7.16 (aromatics, 4H); 7.27-7.38 (aromatics, 2H); 7.50 (d, J = 1.0 Hz, 1H); 7.60-7.63 (aromatics, 2H); 7.89 (d, J = 8.3 Hz, 1H); 8.46 (dd, $J_1$ = 1.5 Hz, $J_2$ = 8.8 Hz, 1H); 8.88 (d, J = 3.9 Hz, 1H); 12.05 (bs, 1H). |

| No. | Structure & IUPAC name | Method/ Intermediates used | Analytical data |
|---|---|---|---|
| A-13 | 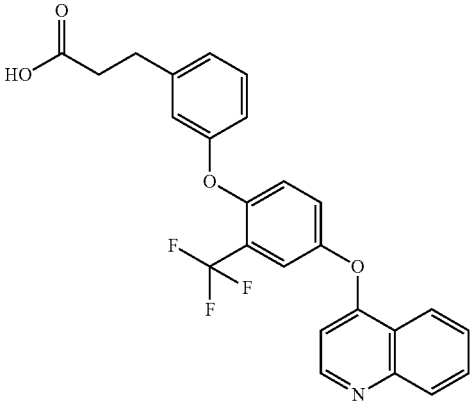<br>3-[3-[4-(4-quinolyloxy)-2-(trifluoromethyl)phenoxy]phenyl]propanoic acid | Method-A/ II-A-2 & 4-hydroxyquinoline | LCMS: m/z; 454.1 (M + 1)⁺. ¹H NMR (DMSO-d₆; 400 MHz) 2.58 (t, J = 7.3 Hz, 2H); 2.88 (t, J = 7.4 Hz, 2H); 6.18 (d, J = 7.8 Hz, 1H); 7.02 (dd, J₁ = 2.0 Hz, J₂ = 8.3 Hz, 1H); 7.05 (d, J = 8.8 Hz, 1H); 7.12 (s, 1H); 7.14-7.18 (aromatics, 2H); 7.39-7.44 (aromatics, 2H); 7.61-7.66 (aromatics, 1H); 7.82 (dd, J₁ = 2.5 Hz, J₂ = 8.8 Hz, 1H); 8.01 (d, J = 7.9 Hz, 1H); 8.07 (d, J = 2.5 Hz, 1H); 8.22 (dd, J₁ = 1.5 Hz, J₂ = 7.8 Hz, 1H); 12.20 (bs, 1H). |
| A-14 | 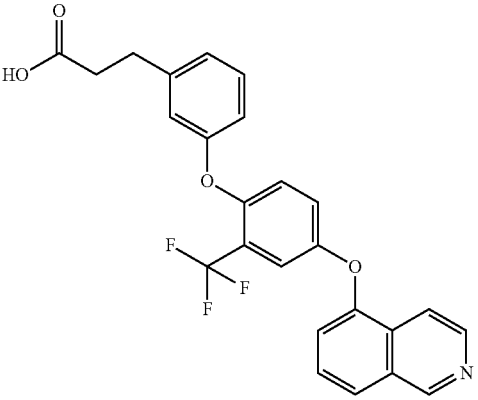<br>3-[3-[4-(5-isoquinolyloxy)-2-(trifluoromethyl)phenoxy]phenyl]propanoic acid | Method-A/ II-A-2 & 5-hyrdoxyisoquinoline | LCMS: m/z; 454.1 (M + 1)⁺. ¹H NMR (DMSO-d₆; 400 MHz) 2.54 (t, J = 7.8 Hz, 2H); 2.83 (t, J = 7.9 Hz, 2H); 6.84-6.88 (aromatics, 1H); 6.98-6.99 (aromatics, 1H); 7.05-7.11 (aromatics, 2H); 7.29-7.40 (aromatics, 3H); 7.58 (d, J = 3.4 Hz, 1H); 7.64-7.69 (aromatics, 1H); 7.94-7.99 (aromatics, 2H); 8.59 (d, J = 5.9 Hz, 1H); 9.41 (s, 1H); 12.14 (bs, 1H). |
| A-15 | 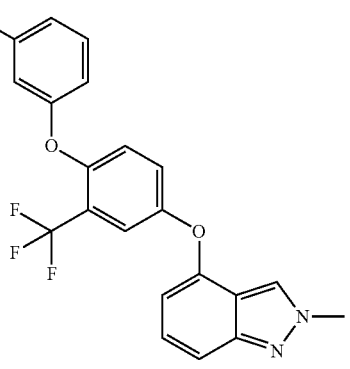<br>2-[3-[4-(2-methylindazol-4-yl)oxy-2-(trifluoromethyl)phenoxy]phenyl]acetic acid | Method-B\ II-B-1 & 4-bromo-2-methylindazole | LCMS: m/z; 443.1 (M + 1)⁺. ¹H NMR (DMSO-d₆; 400 MHz) 3.59 (s, 2H); 4.15 (s, 3H); 6.53 (d, J = 7.4 Hz, 1H); 6.92 (dd, J₁ = 2.2 Hz, J₂ = 8.3 Hz, 1H); 6.98-7.02 (aromatics, 1H); 7.07-7.11 (aromatics, 2H); 7.17-7.22 (aromatics, 1H); 7.30-7.38 (aromatics, 2H); 7.40 (d, J = 8.6 Hz, 1H); 7.49 (d, J = 3.0 Hz, 1H); 8.29 (s, 1H). |

-continued

| No. | Structure & IUPAC name | Method/ Intermediates used | Analytical data |
|---|---|---|---|
| A-16 | 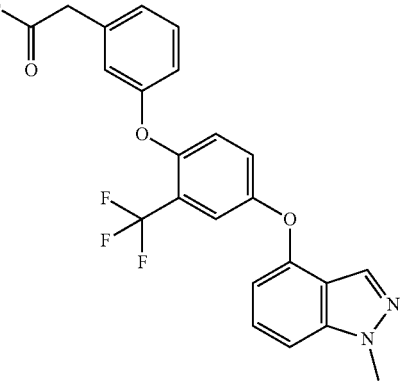<br>2-[3-[4-(1-methylindazol-4-yl)oxy-2-(trifluoromethyl)phenoxy]phenyl]acetic acid | Method-B/ II-B-1 & 4-bromo-1-methylindazole | LCMS: m/z; 443.1 (M + 1)⁺. ¹H NMR (DMSO-d₆; 400 MHz) 3.60 (s, 2H); 4.07 (s, 3H); 6.63 (d, J = 7.3 Hz, 1H); 6.93 (dd, J₁ = 2.2 Hz, J₂ = 7.8 Hz, 1H); 7.00-7.04 (aromatics, 1H); 7.07-7.12 (aromatics, 2H); 7.33-7.45 (aromatics, 4H); 7.52 (d, J = 2.9 Hz, 1H); 7.91 (d, J = 0.8 Hz, 1H); 12.38 (bs, 1H). |
| A-17 | 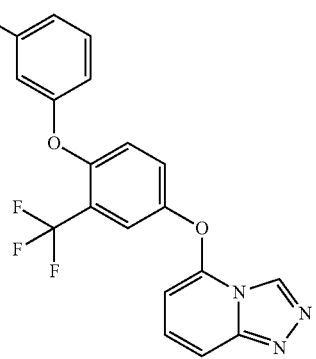<br>2-[3-[4-([1,2,4]triazolo[4,3-a]pyridin-5-yloxy)-2-(trifluoromethyl)phenoxy]phenyl]acetic acid | Method-B/ II-B-1 & 5-bromo-[1,2,4]triazolo[4,3-a]pyridine | LCMS: m/z; 430.1 (M + 1)⁺. ¹H NMR (CDCl₃; 400 MHz) 3.62 (s, 2H); 6.16 (d, J = 8.3 Hz, 1H); 6.99 (d, J = 7.8 Hz, 1H); 7.06 (s, 1H); 7.13 (d, J = 7.5 Hz, 1H); 7.18 (d, J = 9.1 Hz, 1H); 7.32-7.41 (aromatics, 2H); 7.53 (d, J = 9.1 Hz, 1H); 7.73 (dd, J₁ = 1.9 Hz, J₂ = 9.0 Hz, 1H); 7.97 (d, J = 2.6 Hz, 1H); 9.45 (s, 1H); 12.40 (bs, 1H). |
| A-18 | 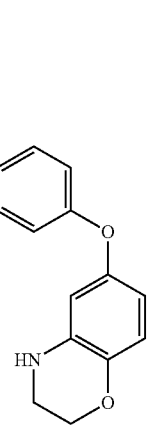<br>2-[3-[4-(3,4-dihydro-2H-1,4-benzoxazin-6-yloxy)-2-(trifluoromethyl)phenoxy]phenyl]acetic acid | Method-A/ II-A-1 & 4-benzyl-2,3-dihydro-1,4-benzoxazin-6-ol | Note: N-debenzylation was done by hydrogenation using Pd/C after Ulmann coupling reaction.<br>LCMS: m/z; 446.2 (M + 1)⁺. ¹H NMR (DMSO-d₆; 400 MHz) 3.20-3.30 (m, 2H); 3.58 (s, 2H); 4.08-4.14 (m, 2H); 5.98 (bs, 1H); 6.19 (dd, J₁ = 2.7 Hz, J₂ = 8.5 Hz, 1H); 6.29 (d, J = 2.7 Hz, 1H); 6.66 (d, J = 8.5 Hz, 1H); 6.86 (dd, J₁ = 2.5 Hz, J₂ = 8.1 Hz, 1H); 6.94-6.98 (aromatics, 1H); 7.04-7.09 (aromatics, 2H); 7.21 (d, J₁ = 3.0 Hz, J₂ = 9.1 Hz, 1H); 7.28 (d, J = 3.0 Hz, 1H); 7.30-7.35 (aromatics, 1H); 12.38 (bs, 1H). |

| No. | Structure & IUPAC name | Method/ Intermediates used | Analytical data |
|---|---|---|---|
| A-19 | 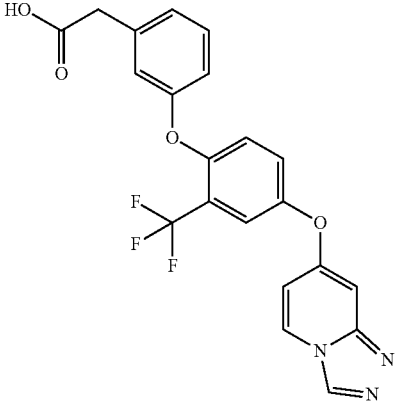 2-[3-[4-([1,2,4]triazolo[4,3-a]pyridin-7-yloxy)-2-(trifluoromethyl)phenoxy]phenyl]acetic acid | Method-B/ II-B-1 & 7-bromo-[1,2,4]triazolo[4,3-a]pyridine | LCMS: m/z; 430.2 (M + 1)$^+$. $^1$H NMR (DMSO-d$_6$; 400 MHz) 3.62 (s, 2H); 6.94 (dd, J$_1$ = 1.9 Hz, J$_2$ = 7.5 Hz, 1H); 7.00 (dd, J$_1$ = 2.0 Hz, J$_2$ = 8.4 Hz, 1H); 7.05-7.16 (aromatics, 4H); 7.35-7.39 (aromatics, 1H); 7.53 (dd, J$_1$ = 2.5 Hz, J$_2$ = 9.3 Hz, 1H); 7.66 (d, J = 3.0 Hz, 1H); 8.60 (d, J = 7.3 Hz, 1H); 9.17 (s, 1H); 12.38 (bs, 1H). |
| A-20 | 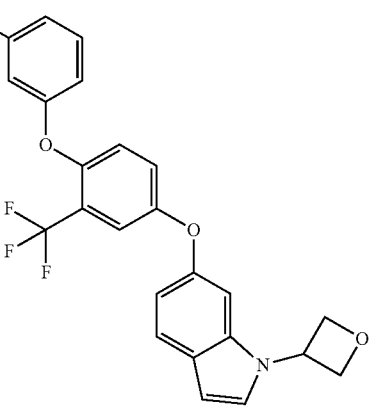 2-[3-[4-[1-(oxetan-3-yl)indol-6-yl]oxy-2-(trifluoromethyl)phenoxy]phenyl]acetic acid | Method-B/ II-B-1 & 6-bromo-1-(oxetan-3-yl)indole (ref: AngewandteChemie, International Edition, 6685; 2013) | LCMS: m/z; 484.2 (M + 1)$^+$. $^1$H NMR (DMSO-d$_6$; 400 MHz) 3.58 (s, 2H); 4.89 (t, J = 6.6 Hz, 2H); 5.01 (t, J = 7.4 Hz, 2H); 5.70-5.80 (m, 1H); 6.60 (d, J = 3.2 Hz, 1H); 6.84-6.89 (aromatics, 2H); 6.95-6.98 (aromatics, 1H); 7.04-7.10 (aromatics, 2H); 7.23 (dd, J$_1$ = 2.9 Hz, J$_2$ = 9.0 Hz, 1H); 7.31-7.35 (aromatics, 2H); 7.40 (d, J = 1.8 Hz, 1H); 7.62 (d, J = 8.3 Hz, 1H); 7.80 (d, J = 3.5 Hz, 1H); 12.38 (bs, 1H). |

-continued

| No. | Structure & IUPAC name | Method/ Intermediates used | Analytical data |
|---|---|---|---|
| A-21 | 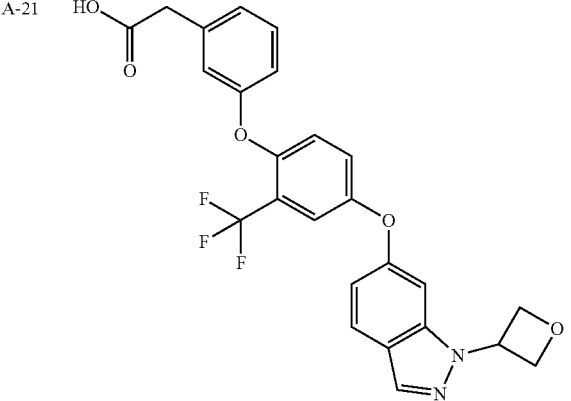<br>2-[3-[4-[1-(oxetan-3-yl)indazol-6-yl]oxy-2-(trifluoromethyl)phenoxy]phenyl]acetic acid | Method-B/ II-B-1 & III-B-4 [6-bromo-1-(oxetan-3-yl)indazole] | LCMS: m/z; 485.1 (M + 1)$^+$. $^1$H NMR (DMSO-d$_6$; 400 MHz) 3.60 (s, 2H); 4.95-5.03 (m, 4H); 5.98-6.06 (m, 1H); 6.92 (dd, J$_1$ = 2.4 Hz, J$_2$ = 8.3 Hz, 1H); 6.96 (dd, J$_1$ = 1.9 Hz, J$_2$ = 8.3 Hz, 1H); 6.92-7.04 (aromatics, 1H); 7.07-7.12 (aromatics, 2H); 7.30-7.38 (aromatics, 2H); 7.41-7.46 (aromatics, 2H); 7.83 (d, J = 8.8 Hz, 1H); 8.23 (s, 1H); 12.38 (bs, 1H). |
| A-22 | 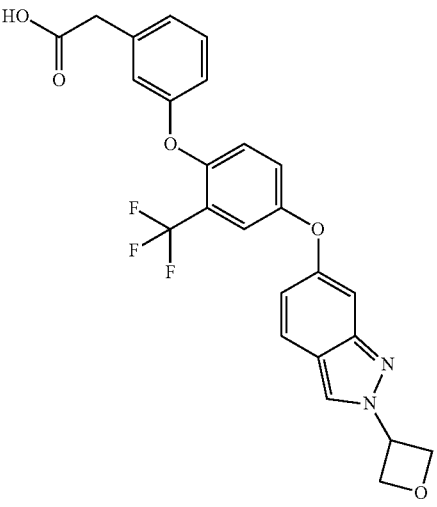<br>2-[3-[4-[2-(oxetan-3-yl)indazol-6-yl]oxy-2-(trifluoromethyl)phenoxy]phenyl]acetic acid | Method-B/ II-B-1 & III-B-5 [6-bromo-2-(oxetan-3-yl)indazole] | LCMS: m/z; 485.1 (M + 1)$^+$. $^1$H NMR (DMSO-d$_6$; 400 MHz) 3.61 (s, 2H); 5.01 (s, 2H); 5.03 (s, 2H); 5.85-5.95 (m, 1H); 6.90-6.96 (aromatics, 2H); 7.00-7.05 (aromatics, 1H); 7.07-7.13 (aromatics, 2H); 7.22 (bs, 1H); 7.32-7.38 (aromatics, 2H); 7.42-7.43 (aromatics, 1H); 7.80 (d, J = 8.8 Hz, 1H); 8.53 (s, 1H); 12.38 (bs, 1H). |

| No. | Structure & IUPAC name | Method/ Intermediates used | Analytical data |
|---|---|---|---|
| A-23 | 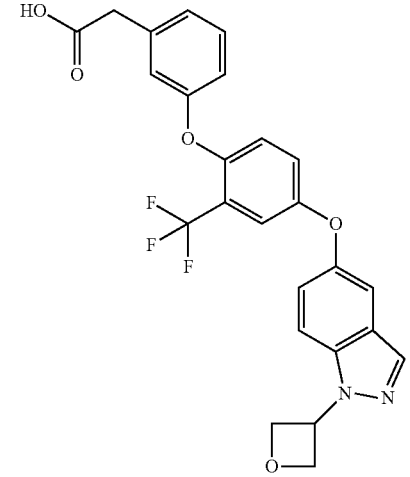<br>2-[3-[4-[1-(oxetan-3-yl)indazol-5-yl]oxy-2-(trifluoromethyl)phenoxy]phenyl]acetic acid | Method-B/ II-B-1 & III-B-6 [5-bromo-1-(oxetan-3-yl)indazole] | LCMS: m/z; 485.1 (M + 1)+. $^1$H NMR (DMSO-$d_6$; 400 MHz) 3.59 (s, 2H); 4.98-5.05 (m, 4H); 6.04-6.09 (m, 1H); 6.89 (dd, $J_1$ = 2.0 Hz, $J_2$ = 8.3 Hz, 1H); 6.96-7.00 (aromatics, 1H); 7.05-7.11 (aromatics, 2H); 7.23-7.36 (aromatics, 4H); 7.50 (d, J = 1.6 Hz, 1H); 7.79 (d, J = 9.3 Hz, 1H); 8.21 (s, 1H); 12.36 (bs, 1H). |
| A-24 | 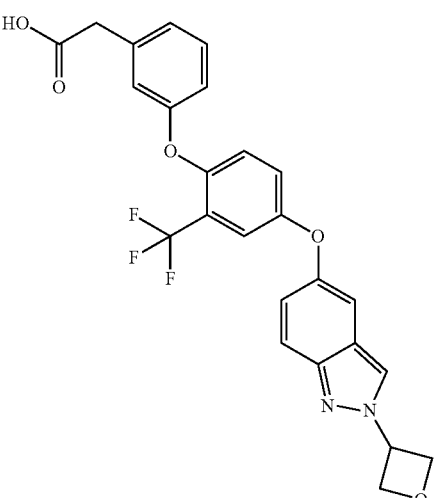<br>2-[3-[4-[2-(oxetan-3-yl)indazol-5-yl]oxy-2-(trifluoromethyl)phenoxy]phenyl]acetic acid | Method-B/ II-B-1 & III-B-7 [5-bromo-2-(oxetan-3-yl)indazole] | LCMS: m/z; 485.1 (M + 1)+. $^1$H NMR (DMSO-$d_6$; 400 MHz) 3.59 (s, 2H); 5.02 (s, 2H); 5.03 (s, 2H); 5.86-5.92 (m, 1H); 6.90 (dd, $J_1$ = 1.9 Hz, $J_2$ = 8.4 Hz, 1H); 6.98-7.00 (aromatics, 1H); 7.06-7.11 (aromatics, 2H); 7.14 (dd, $J_1$ = 2.4 Hz, $J_2$ = 9.3 Hz, 1H); 7.28 (dd, $J_1$ = 3.0 Hz, $J_2$ = 8.8 Hz,, 1H); 7.32-7.38 (aromatics, 3H); 7.78 (d, J = 9.3 Hz, 1H); 8.46 (s, 1H); 12.38 (bs, 1H). |

| No. | Structure & IUPAC name | Method/ Intermediates used | Analytical data |
|---|---|---|---|
| A-25 | 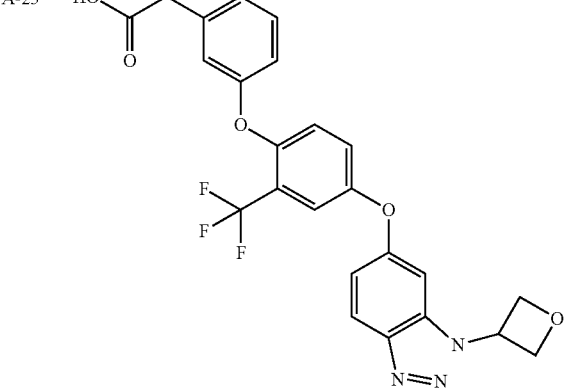<br>2-[3-[4-[3-(oxetan-3-yl)benzotriazol-5-yl]oxy-2-(trifluoromethyl)phenoxy]phenyl]acetic acid | Method-B/ II-B-1 & III-B-10 [6-bromo-1-(oxetan-3-yl)benzotriazole] | LCMS: m/z; 486.1 (M + 1)+. $^1$H NMR (DMSO-$d_6$; 400 MHz) 3.61 (s, 2H); 5.06-5.11 (m, 4H); 6.14-6.22 (m, 1H); 6.93 (dd, $J_1$ = 2.0, $J_2$ = 7.9 Hz, 1H); 7.00-7.04 (bs 1H); 7.08-7.13 (aromatics, 2H); 7.24 ($J_1$ = 2.0, $J_2$ = 8.8 Hz, 1H); 7.34-7.40 (aromatics, 2H); 7.52 (d, J = 3.0 Hz, 1H); 7.54 (d, J = 1.9 Hz, 1H); 8.13 (d, J = 8.8 Hz, 1H); 12.40 (bs, 2H). |
| A-26 | 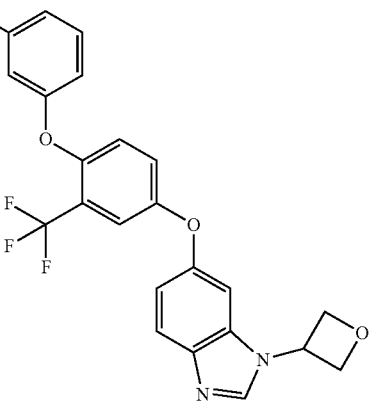<br>2-[3-[4-[3-(oxetan-3-yl)benzimidazol-5-yl]oxy-2-(trifluoromethyl)phenoxy]phenyl]acetic acid | Method-B/ II-B-1 & III-B-11 [6-bromo-1-(oxetan-3-yl)benzimidazole] | LCMS: m/z; 499.3 (M + 1)+. $^1$H NMR (DMSO-$d_6$; 400 MHz) 3.59 (s, 2H); 4.96 (t, J = 6.9 Hz, 2H); 5.05 (t, J = 7.4 Hz, 2H); 5.70-5.76 (m, 1H); 6.89 (dd, $J_1$ = 1.9 Hz, $J_2$ = 8.3 Hz, 1H); 6.96-6.98 (aromatics, 1H); 7.02-7.12 (aromatics, 3H); 7.28 (dd, $J_1$ = 2.9 Hz, $J_2$ = 8.8 Hz, 1H); 7.31-7.35 (aromatics, 1H); 7.37 (d, J = 3.0 Hz, 1H); 7.54 (d, J = 2.4 Hz, 1H); 7.74 (d, J = 8.8 Hz, 1H); 8.55 (s, 1H); 12.38 (bs, 1H). |

-continued

| No. | Structure & IUPAC name | Method/ Intermediates used | Analytical data |
|---|---|---|---|
| A-27 | 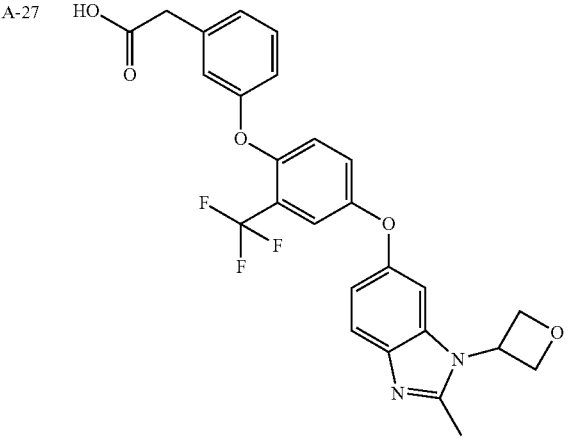<br>2-[3-[4-[2-methyl-3-(oxetan-3-yl)benzimidazol-5-yl]oxy-2-(trifluoromethyl)phenoxy]phenyl]acetic acid | Method-B/ II-B-1 & III-B-12 [6-bromo-2-methyl-1-(oxetan-3-yl)benzimidazole] | LCMS: m/z; 499.3 (M + 1)$^+$. $^1$H NMR (DMSO-d$_6$; 400 MHz) 2.47 (s, 3H); 3.55 (s, 2H); 4.90-5.12 (m, 4H); 5.58-5.62 (m, 1H); 6.70-7.15 (aromatics, 5H); 7.24-7.40 (aromatics, 3H); 7.55-7.70 (aromatics, 2H); 12.31 (bs, 1H). |
| A-28 | 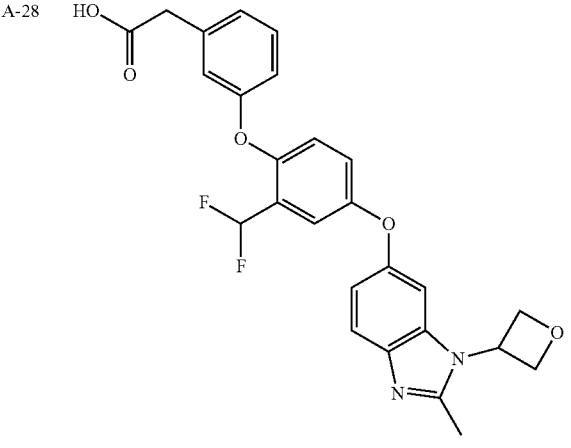<br>2-[3-[2-(difluoromethyl)-4-[2-methyl-3-(oxetan-3-yl)benzimidazol-5-yl]oxy-phenoxy]phenyl]acetic acid | Method-B/ II-B-5 & III-B-12 [6-bromo-2-methyl-1-(oxetan-3-yl)benzimidazole] | LCMS: m/z; 481.2 (M + 1)$^+$. $^1$H NMR (DMSO-d$_6$; 400 MHz) 2.50 (s, 3H); 3.58 (s, 2H); 4.95-4.99 (m, 2H); 5.06-5.10 (m, 2H); 5.62-5.70 (m, 1H); 6.85-6.90 (aromatics, 1H); 6.95-7.06 (aromatics, 4H); 7.12-7.36 (aromatics, 4H); 7.62 (d, J = 8.8 Hz, 1H); 7.65 (d, J = 1.9 Hz, 1H); 12.40 (bs, 1H). |

| No. | Structure & IUPAC name | Method/ Intermediates used | Analytical data |
|---|---|---|---|
| A-29 | 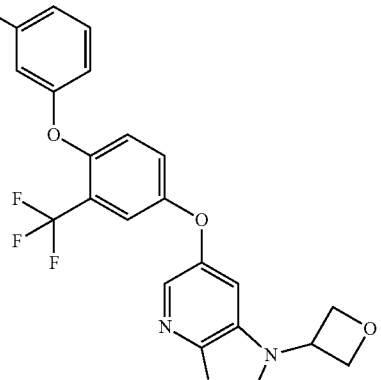<br>2-[3-[4-[1-(oxetan-3-yl)imidazo[4,5-b]pyridin-6-yl]oxy-2-(trifluoromethyl)phenoxy]phenyl]acetic acid | Method-B/ II-B-1 & III-B-8 {6-bromo-1-(oxetan-3-yl)imidazo[4,5-b]pyridine} | LCMS: m/z; 486.2 (M + 1)+. $^1$H NMR (DMSO-d$_6$; 400 MHz) 3.59 (s, 2H); 5.00 (t, J = 7.4 Hz, 2H); 5.18 (t, J = 6.8 Hz, 2H); 5.80-5.90 (m, 1H); 6.90 (dd, J$_1$ = 2.5 Hz, J$_2$ = 8.3 Hz, 1H); 6.96-7.00 (aromatics, 1H); 7.05-7.10 (aromatics, 2H); 7.29 (dd, J$_1$ = 3.0 Hz, J$_2$ = 9.3 Hz, 1H); 7.31-7.36 (aromatics, 1H); 7.42 (d, J = 2.9 Hz, 1H); 7.99 (d, J = 2.5 Hz, 1H); 8.36 (d, J = 2.4 Hz, 1H); 8.79 (s, 1H); 12.35 (bs, 1H). |
| A-30 | 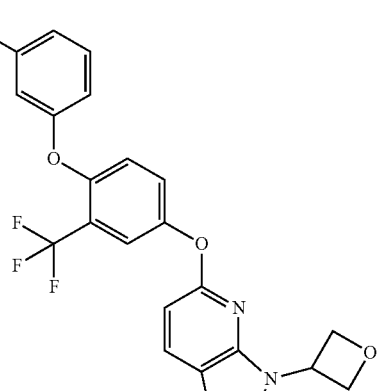<br>2-[3-[4-[1-(oxetan-3-yl)pyrrolo[2,3-b]pyridin-6-yl]oxy-2-(trifluoromethyl)phenoxy]phenyl]acetic acid | Method-B/ II-B-1 & III-B-9 {6-bromo-1-(oxetan-3-yl)pyrrolo[2,3-b]pyridine} | LCMS: m/z; 485.1 (M + 1)+. $^1$H NMR (DMSO-d$_6$; 400 MHz) 3.67 (s, 2H); 5.04 (s, 2H); 5.06 (s, 2H); 5.92-5.97 (m, 1H); 6.54 (d, J = 3.4 Hz, 1H); 6.79 (d, J = 8.3 Hz, 1H); 6.99-7.05 (aromatics, 3H); 7.08-7.14 (aromatics, 1H); 7.31-7.37 (aromatics, 2H); 7.41 (d, J = 3.4 Hz, 1H); 7.47 (d, J = 2.4 Hz, 1H); 7.91 (d, J = 8.8 Hz, 1H). |

| No. | Structure & IUPAC name | Method/ Intermediates used | Analytical data |
|---|---|---|---|
| A-31 | 6-[4-[3-(carboxymethyl)phenoxy]-3-(trifluoromethyl)phenoxy]imidazo[1,5-a]pyridine-3-carboxylic acid | Method-B/ II-B-1 & methyl 6-bromoimidazo[1,5-a]pyridine-3-carboxylate | LCMS: m/z; 473.1 (M + 1)+. $^1$H NMR (DMSO-$d_6$; 400 MHz) 3.60 (s, 2H); 6.90-6.92 (aromatics, 1H); 7.00-7.04 (aromatics, 1H); 7.08-7.20 (aromatics, 3H); 7.34-7.44 (aromatics, 2H); 7.56-7.60 (aromatics, 1H); 7.73 (s, 1H); 7.94 (d, J = 9.8 Hz, 1H); 9.05 (s, 1H); 12.50 (bs, 1H). |
| A-32 | 2-[3-[4-[1-(carboxymethyl)indol-5-yl]oxy-2-(trifluoromethyl)phenoxy]phenyl]acetic acid | Method-B/ II-B-1 & methyl 2-(5-bromoindol-1-yl)acetate | LCMS: m/z; 486.1 (M + 1)+. $^1$H NMR (DMSO-$d_6$; 400 MHz) 3.59 (s, 2H); 5.04 (s, 2H); 6.45 (d, J = 3.0 Hz, 1H); 6.87 (d, J = 7.8 Hz, 1H); 6.92-6.98 (aromatics, 2H); 7.02-7.10 (aromatics, 2H); 7.18-7.24 (aromatics, 1H); 7.26-7.36 (aromatics, 3H); 7.41 (d, J = 3.4 Hz, 1H); 7.46 (d, J = 8.8 Hz, 1H); 12.60 (bs, 2H). |

| No. | Structure & IUPAC name | Method/ Intermediates used | Analytical data |
|---|---|---|---|
| A-33 | 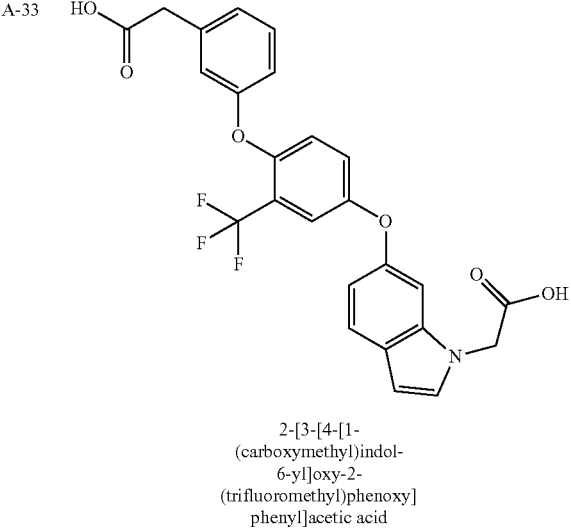 2-[3-[4-[1-(carboxymethyl)indol-6-yl]oxy-2-(trifluoromethyl)phenoxy] phenyl]acetic acid | Method-B/ II-B-1 & methyl 2-(6-bromoindol-1-yl)acetate | LCMS: m/z; 486.1 (M + 1)+. 1H NMR (DMSO-d6; 400 MHz) 3.59 (s, 2H); 4.99 (s, 2H); 6.48 (d, J = 2.9 Hz, 1H); 6.82-6.88 (aromatics, 2H); 6.94-6.98 (aromatics, 1H); 7.04-7.10 (aromatics, 2H); 7.21-7.35 (aromatics, 5H); 7.59 (d, J = 8.3 Hz, 1H); 12.60 (bs, 2H). |
| A-34 | 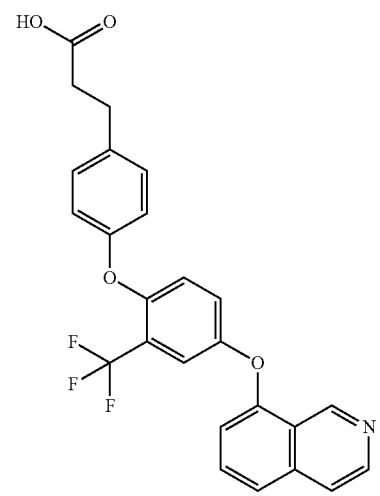 3-[4-[4-(8-isoquinolyloxy)-2-(trifluoromethyl)phenoxy] phenyl]propanoic acid | Method-A/ II-A-3 & 8-hyroxyisoquinoline | LCMS: m/z; 454.2 (M + 1)+. 1H NMR (DMSO-d6; 400 MHz) 2.54 (J = 7.8 Hz, 2H); 2.82 (t, J = 7.3 Hz, 2H); 7.01 (d, J = 8.5 Hz, 2H); 7.06 (dd, J1 = 1.4 Hz, J2 = 6.8 Hz, 1H); 7.11 (d, J = 9.1 Hz, 1H); 7.29 (d, J = 8.6 Hz, 2H); 7.46 (dd, J1 = 2.9 Hz, J2 = 9.0 Hz, 1H); 7.65 (d, J = 3.0 Hz, 1H); 7.70-7.76 (aromatics, 2H); 7.90 (d, J = 5.9 Hz, 1H); 8.61 (d, J = 5.9 Hz, 1H); 9.59 (s, 1H); 12.18 (bs, 1H). |

-continued

| No. | Structure & IUPAC name | Method/ Intermediates used | Analytical data |
|---|---|---|---|
| A-35 | 3-[3-[4-(2-methylindazol-5-yl)oxy-2-(trifluoromethyl)phenoxy]phenyl]propanoic acid | Method-B/ II-B-2 & 5-bromo-2-methyl-indazole | LCMS: m/z; 457.2 (M + 1)+. $^{1}$H NMR (DMSO-$d_6$; 400 MHz) 2.53 (t, J = 7.5 Hz, 2H); 2.81 (t, J = 7.6 Hz, 2H); 4.06 (s, 3H); 6.81 (dd, $J_1$ = 1.9 Hz, $J_2$ = 8.0 Hz, 1H); 6.94 (s, 1H); 7.00-7.08 (aromatics, 2H); 7.21-7.35 (aromatics, 3H); 7.44-7.50 (aromatics, 2H); 7.72 (d, J = 9.0 Hz, 1H); 8.01 (s, 1H); 12.18 (bs, 1H). |
| A-36 | 2-[3-[[5-(8-isoquinolyloxy)-3-(trifluoromethyl)-2-pyridyl]oxy]phenyl]acetic acid | Method-B/ II-B-3 & 8-hyrdoxyisoquinoline | LCMS: m/z; 517.2 (M + 1)+. $^{1}$H NMR (DMSO-$d_6$; 400 MHz) 3.62 (s, 2H); 7.06 (d, J = 6.6 Hz, 1H); 7.08-7.15 (aromatics, 2H); 7.16 (d, J = 7.9 Hz, 1H); 7.36-7.41 (aromatics, 1H); 7.66-7.76 (aromatics, 2H); 7.90 (d, J = 5.7 Hz, 1H); 8.29 (d, J = 2.7 Hz, 1H); 8.42 (d, J = 2.7 Hz, 1H); 8.62 (d, J = 5.6 Hz, 1H); 9.63 (s, 1H); 12.38 (bs, 1H). |

| No. | Structure & IUPAC name | Method/ Intermediates used | Analytical data |
|---|---|---|---|
| A-37 | 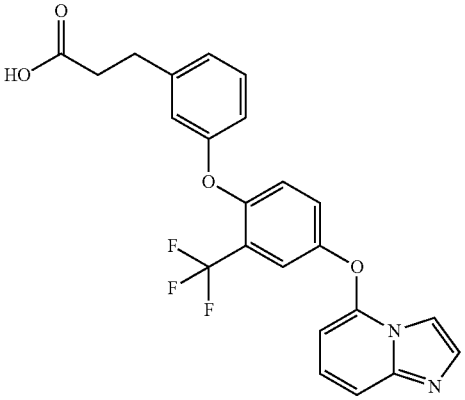<br>3-[3-[4-imidazo[1,2-a]pyridin-5-yloxy-2-(trifluoromethyl)phenoxy]phenyl]propanoic acid | Method-B/<br>II-B-1 & 5-bromoimidazo[1,2-a]pyridine | LCMS: m/z; 443.2 (M + 1)⁺. ¹H NMR (DMSO-$d_6$; 400 MHz) 2.56 (t, J = 7.5 Hz, 2H); 2.85 (t, J = 7.6 Hz, 2H); 6.25 (d, J = 7.5 Hz, 1H); 6.92 (dd, $J_1$ = 2.1 Hz, $J_2$ = 8.0 Hz, 1H); 7.03 (bs, 1H); 7.00 (d, J = 7.1 Hz, 1H); 7.14 (d, J = 9.1 Hz, 1H); 7.29-7.42 (aromatics, 3H); 7.64 (dd, $J_1$ = 3.3 Hz, $J_2$ = 9.1 Hz, 1H); 7.71 (s, 1H); 7.87 (d, J = 2.7 Hz, 1H); 8.03 (s, 1H); 12.18 (bs, 1H). |
| A-38 | 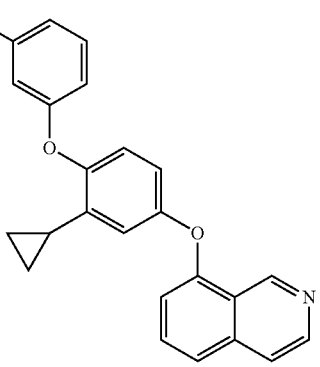<br>2-[3-[2-cyclopropyl-4-(8-isoquinolyloxy)phenoxy]phenyl]acetic acid | Method-B/<br>II-B-4 & 8-hydroxyisoquinoline | LCMS: m/z; 412.3 (M + 1)⁺. ¹H NMR (DMSO-$d_6$; 400 MHz) 0.68-0.72 (m, 2H); 0.84-0.88 (m, 2H); 1.97-2.01 (m, 1H); 3.57 (s, 2H); 6.51 (s, 1H); 6.81 (dd, $J_1$ = 2.0 Hz, $J_2$ = 8.0 Hz, 1H); 6.89-7.03 (aromatics, 5H); 7.27-7.32 (aromatics, 1H); 7.67-7.72 (aromatics, 2H); 7.87 (dd, $J_1$ = 0.8 Hz, $J_2$ = 5.6 Hz, 1H); 8.59 (d, J = 5.6 Hz, 1H); 9.58 (s, 1H); 12.32 (bs, 1H). |
| A-39 | 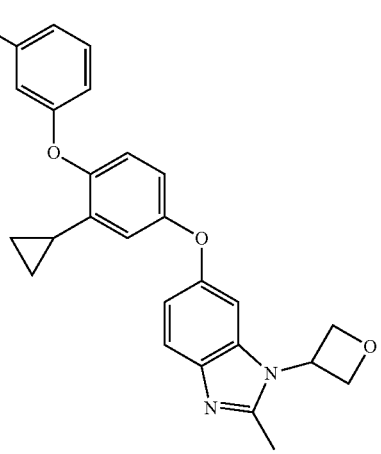<br>2-[3-[2-cyclopropyl-4-[2-methyl-3-(oxetan-3-yl)benzimidazol-5-yl]oxy-phenoxy]phenyl]acetic acid | Method-B/<br>II-B-4 & III-B-12 [6-bromo-2-methyl-1-(oxetan-3-yl)benzimidazole] | LCMS: m/z; 471.2 (M + 1)+. ¹H NMR (DMSO-$d_6$; 400 MHz) 0.59-0.63 (m, 2H); 0.80-0.90 (m, 2H); 1.90-1.98 (m, 1H); 2.49 (s, 3H); 3.54 (s, 2H); 4.93-4.96 (m, 2H); 5.05-5.12 (m, 2H); 5.58-5.64 (m, 1H); 6.67 (d, J = 3.0 Hz, 1H); 6.75 (dd, $J_1$ =1.9 Hz, $J_2$ = 7.8 Hz, 1H); 6.80 (dd, $J_1$ = 3 Hz, $J_2$ = 8.8 Hz, 1H); 6.81-6.83 (aromatics, 1H); 6.92-6.96 (aromatics, 3H); 7.23-7.28 (aromatics, 1H); 7.56-7.58 (aromatics, 2H); 12.35 (bs, 1H). |

Synthesis of 2-[3-[4-[(1-chloro-8-isoquinolyl)oxy]-2-(trifluoromethyl)phenoxy]phenyl]acetic Acid (A-40)

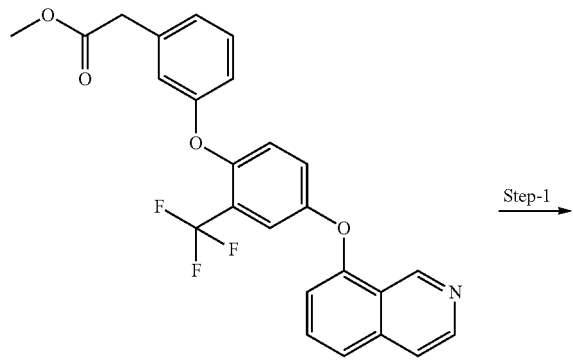

A-1-I

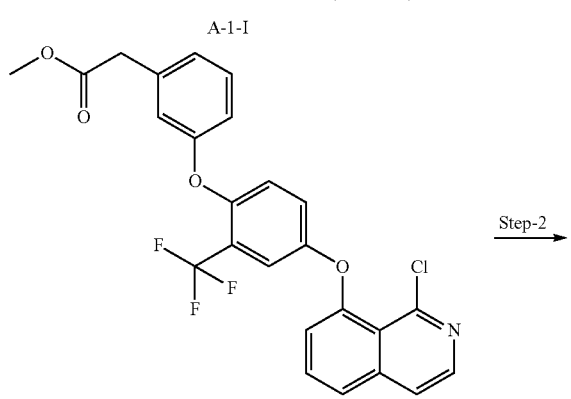

A-40-I

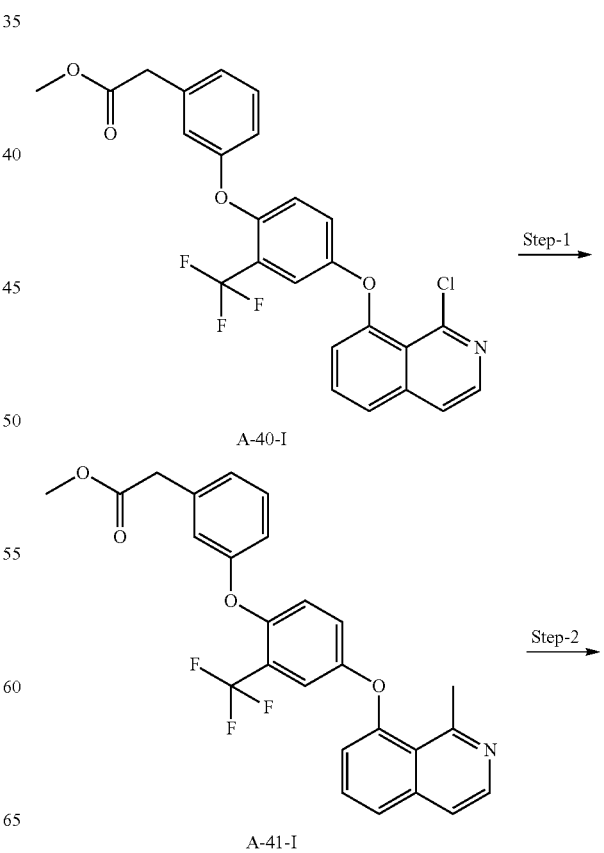

A-40

Step-1: methyl 2-[3-[4-[(1-chloro-8-isoquinolyl)oxy]-2-(trifluoromethyl)phenoxy]phenyl]acetate (A-40-I)

Intermediate A-1-I (1 g, 2.2 mmol) was dissolved in CH$_2$Cl$_2$ (20 mL); to which 3-chloroperbenzoic acid (70%, 0.82 g, 3.3 mmol) was added and the reaction mixture was stirred at room temperature for 4 h. After completion consumption of starting material, it was diluted using saturated sodium thiosulfate solution (30 mL) and extraction was carried out using CH$_2$Cl$_2$ (30 mL×2). The combined organic layers were washed with saturated NaHCO$_3$ solution (30 mL×2); brine (30 mL); dried over anhydrous Na$_2$SO$_4$, filtered and concentrated under reduced pressure. The residue obtained was purified using silica gel column chromatography (0-5% MeOH in CH$_2$Cl$_2$) to provide corresponding N-oxide derivative (0.42 g). LCMS: m/z; 470.2 (M+1)$^+$. This was stirred in POCl$_3$ (3 mL) at 90° C. for 5 h. After completion of the reaction, POCl$_3$ was removed under reduced pressure and saturated NaHCO$_3$ solution (30 mL) was added to it. Extraction was carried out using EtOAc (30 mL×2). The combined organic layers were washed with water (50 mL); brine (50 mL); dried over anhydrous Na$_2$SO$_4$, filtered and concentrated under reduced pressure. The residue obtained was purified using silica gel column chromatography (0-30% EtOAc in hexane) to provide desired intermediate A-40-1 (0.2 g, 18% for 2 steps). LCMS: m/z; 488.2 (M+1)$^+$.

Step-2: 2-[3-[4-[(1-chloro-8-isoquinolyl)oxy]-2-(trifluoromethyl)phenoxy]phenyl]acetic Acid (A-40)

As described in step-2 for the synthesis of A-1.A-40 (0.05 g, 51% yield) obtained from A-40-I (0.1 g). LCMS: m/z; 474.1 (M+1)$^+$. $^1$H NMR (DMSO-d$_6$; 400 MHz) 3.61 (s, 2H); 6.91 (dd, J$_1$=2.5 Hz, J$_2$=7.8 Hz, 1H); 7.00 (s, 1H); 7.06-7.12 (aromatics, 2H); 7.27 (dd, J$_1$=3.2 Hz, J$_2$=8.8 Hz, 1H); 7.33-7.37 (aromatics, 2H); 7.46 (d, J=3.0 Hz, 1H); 7.82-7.87 (aromatics, 1H); 7.92-7.97 (aromatics, 2H); 8.34 (d, J=5.6 Hz, 1H); 12.38 (bs, 1H).

Synthesis of 2-[3-[4-[(1-methyl-8-isoquinolyl)oxy]-2-(trifluoromethyl)phenoxy]phenyl]acetic Acid (A-41)

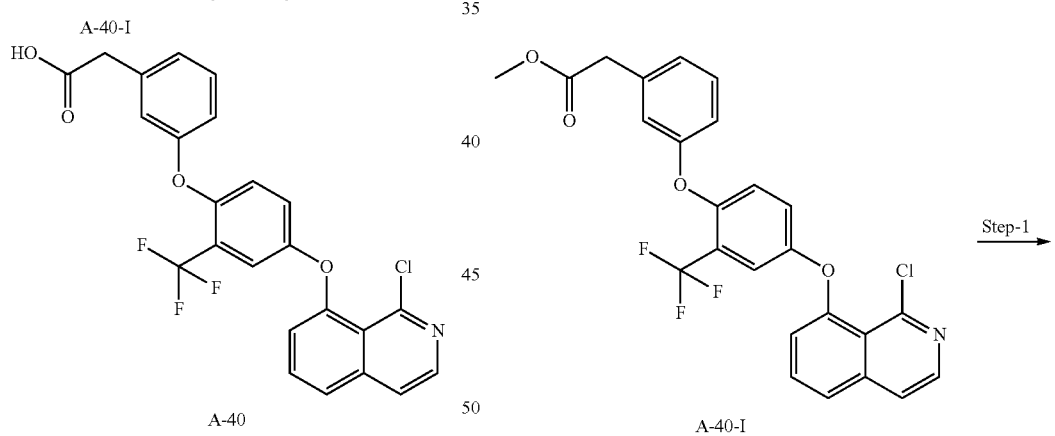

A-40-I

A-41-I

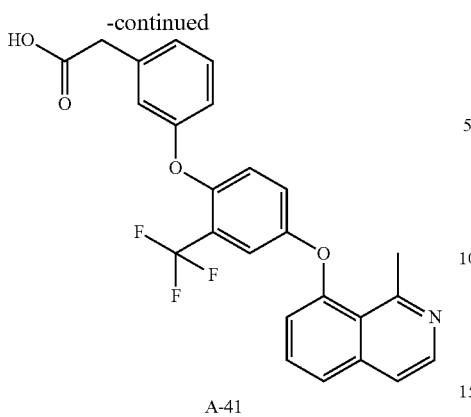

A-41

Step-1: Methyl 2-[3-[4-[(1-methyl-8-isoquinolyl)oxy]-2-(trifluoromethyl)phenoxy]phenyl]acetate (A-41-I)

To a solution of intermediate A-40-I (0.1 g, 0.2 mmol), iron(III)acetylacetonate (0.007 g, 0.02 mmol) and NMP (0.032 g, 0.27 mmol) in anhydrous THF (3 mL) was added MeMgBr (1.3 mL, 1.33 mmol). The reaction mixture was stirred at room temperature for 18 h. Saturated NH₄Cl solution (20 mL) was added to it and extraction was carried out using EtOAc (10 mL×3). The combined organic layers were washed with water (30 mL); brine (30 mL); dried over anhydrous Na₂SO₄, filtered and concentrated under reduced pressure. The residue obtained was purified using silica gel column chromatography (0-30% EtOAc in hexane) to provide desired intermediate A-41-1 (0.075 g, 78% yield). LCMS: m/z; 468.2 (M+1)⁺.

Step-2: 2-[3-[4-[(1-methyl-8-isoquinolyl)oxy]-2-(trifluoromethyl)phenoxy]phenyl]acetic Acid (A-41)

As described in step-2 for the synthesis of A-1.A-41 (0.045 g, 62% yield) obtained from A-41-I (0.075 g). LCMS: m/z; 454.2 (M+1)⁺. ¹H NMR (DMSO-d₆; 400 MHz) 3.08 (s, 3H); 3.61 (s, 2H); 6.95 (dd, J₁=2.0 Hz, J₂=8.1 Hz, 1H); 7.03 (s, 1H); 7.10 (d, J=7.6 Hz, 1H); 7.15 (d, J=8.8 Hz, 2H); 7.34-7.38 (aromatics, 1H); 7.42 (dd, J₁=2.6 Hz, J₂=8.8 Hz, 1H); 7.61 (d, J=3.0 Hz, 1H); 7.76-7.82 (aromatics, 2H); 7.88 (d, J=5.9 Hz, 1H); 8.41 (d, J=5.9 Hz, 1H); 12.37 (bs, 1H).

Synthesis of 3-[3-[4-(8-isoquinolyloxy)-2-(trifluoromethyl)phenoxy]phenyl]propanoic Acid (A-42)

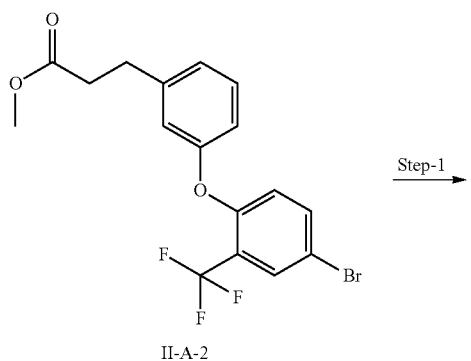

II-A-2

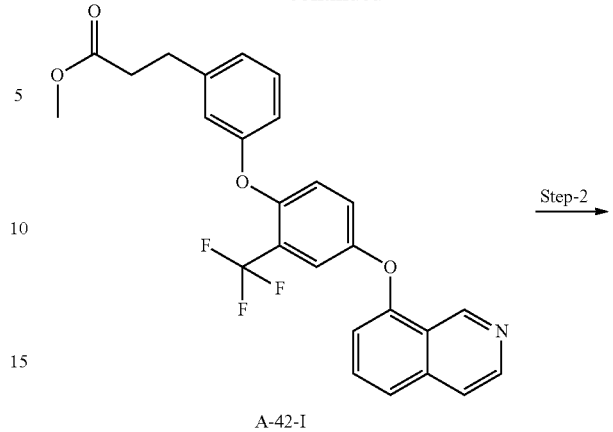

A-42-I

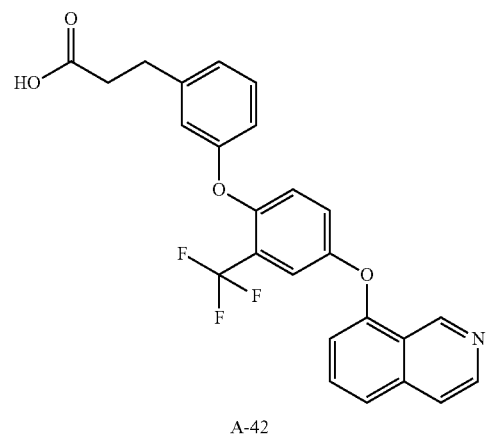

A-42

Step-1: Methyl 3-[3-[4-(8-isoquinolyloxy)-2-(trifluoromethyl)phenoxy]phenyl]propanoate (A-42-I)

Intermediate A-42-I (0.175 g, 15% yield) was synthesized by following procedure described in step-1, method-B for the synthesis of A1; using intermediate II-A-2 (1 g, 2.5 mmol), 8-hydroxyisoquinoline (0.47 g, 3.22 mmol), CuCl (0.37 g, 3.7 mmol), 2,2,6,6-tetramethyl-3,5-heptanedione (0.26 mL, 1.24 mmol), Cs₂CO₃ (1.6 g, 5 mmol) in NMP (12 mL). LCMS: m/z; 467.9 (M+1)⁺.

Step-2: 3-[3-[4-(8-isoquinolyloxy)-2-(trifluoromethyl)phenoxy]phenyl]propanoic Acid (A-42)

As described in step-2 for the synthesis of A-1 using A-42-I (0.06 g). 64% yield. LCMS: m/z; 454.1 (M+1)⁺. ¹H NMR (DMSO-d₆; 400 MHz) 2.55 (t, J=7.9 Hz, 2H); 2.84 (t, J=7.3 Hz, 2H); 6.89 (d, J=8.3 Hz, 1H); 7.01 (s, 1H); 7.06-7.13 (aromatics, 3H); 7.31-7.35 (aromatics, 1H); 7.46 (dd, J₁=2.9 Hz, J₂=8.8 Hz, 1H); 7.66 (d, J=3.0 Hz, 1H); 7.70-7.75 (aromatics, 2H); 7.90 (d, J=5.9 Hz, 1H); 8.61 (d, J=5.8 Hz, 1H); 9.58 (s, 1H); 12.18 (bs, 1H).

Synthesis of 3-[3-[4-(1,2,3,4-tetrahydroisoquinolin-8-yloxy)-2-(trifluoromethyl)phenoxy]phenyl]propanoic Acid (A-43)

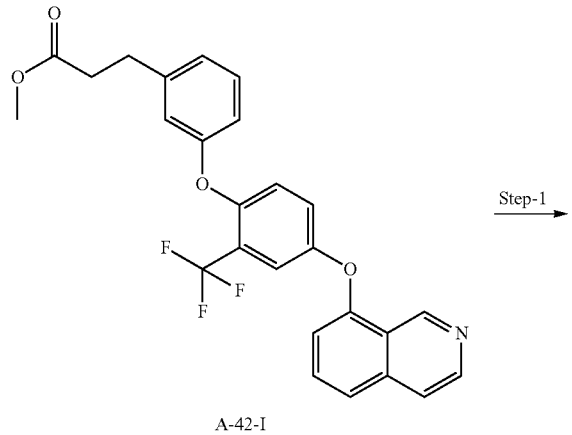

Step-1: Methyl 3-[3-[4-(1,2,3,4-tetrahydroisoquinolin-8-yloxy)-2-(trifluoromethyl)phenoxy]phenyl]propanoate (A-43-I)

A solution of A-42-I (0.175 g) and PtO$_2$ (30 mg) in MeOH (20 mL) was hydrogenated (50 psi) for 5 h. After completion of the reaction, the catalyst was filtered off through celite and washed with MeOH (10 mL×12). The combined organic layers were concentrated under reduced pressure and the residue was purified using silica gel column chromatography (0-5% MeOH in CH$_2$Cl$_2$) to provide desired intermediate A-43-I (0.15 g). LCMS: m/z; 471.9 (M+1)$^+$.

Step-2: 3-[3-[4-(1,2,3,4-tetrahydroisoquinolin-8-yloxy)-2-(trifluoromethyl)phenoxy]phenyl]propanoic Acid (A-43)

A-43 (0.018 g) was synthesized as described in step-2 for the synthesis of A-1 using A-43-I (0.05 g). LCMS: m/z; 458.2 (M+1)$^+$. $^1$H NMR (DMSO-d$_6$; 400 MHz) 2.45-2.55 (m, 2H); 2.68-2.80 (m, 4H); 3.08-3.14 (m, 2H); 3.92 (s, 2H); 6.80-6.84 (aromatics, 2H); 6.93 (bs, 1H); 6.99-7.09 (aromatics, 3H); 7.18-7.26 (aromatics, 2H); 7.28-7.36 (aromatics, 2H).

Synthesis of 3-[3-[4-indan-1-yloxy-2-(trifluoromethyl)phenoxy]phenyl]propanoic acid (A-44)

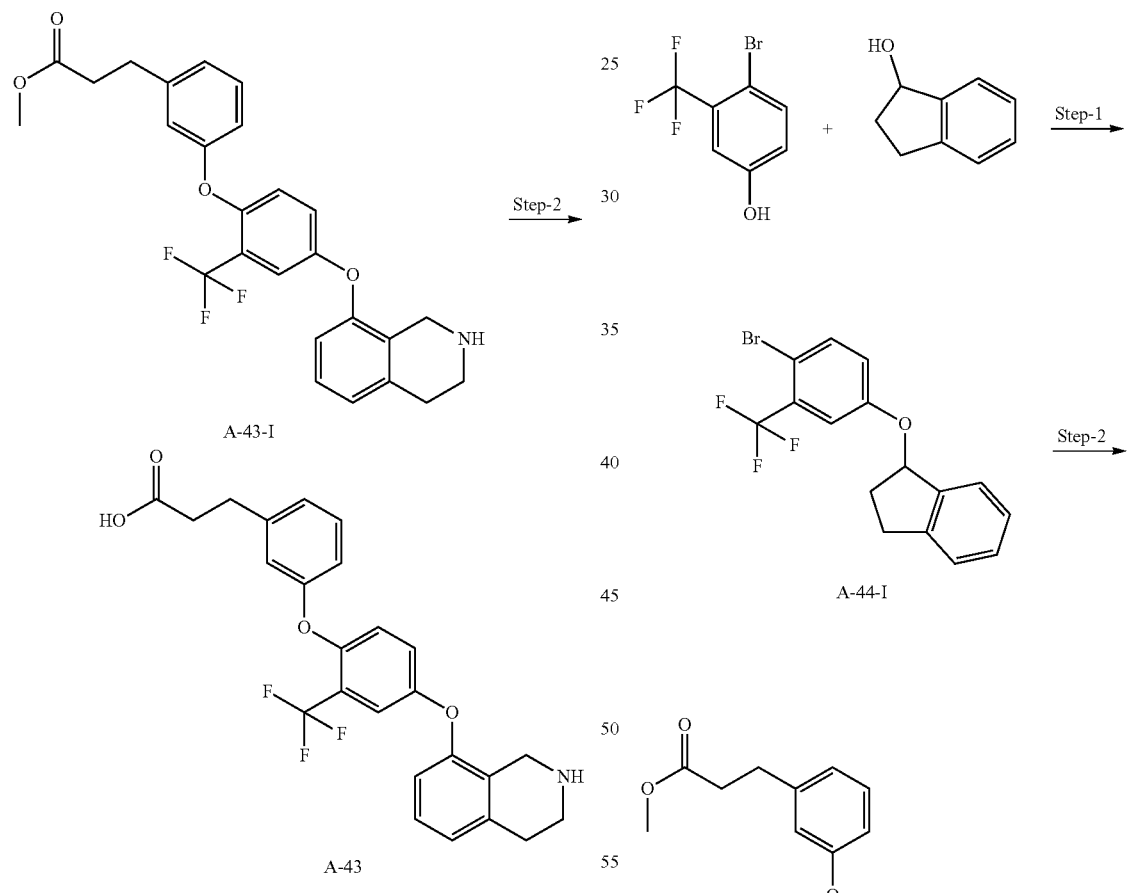

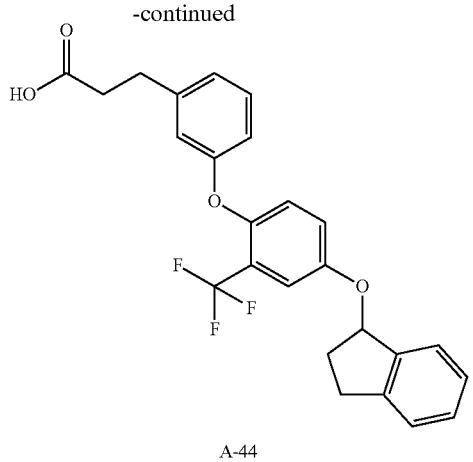

A-44

Step-1: 1-[4-bromo-3-(trifluoromethyl)phenoxy]indane (A-44-I)

To a solution of 4-bromo-3-(trifluoromethyl)phenol (0.5 g, 3.72 mmol), indan-1-ol (1.7 g, 7.5 mmol) and PPh$_3$ (1.46 g, 5.6 mmol) in anhydrous THF (10 mL) was added DIAD (1.1 mL, 5.6 mmol) at 0° C. The reaction mixture was allowed to come to room temperature and stirred for 18 h. It was then diluted using water (30 mL) and extraction was carried out using EtOAc (30 mL×2). The combined organic layers were washed with brine (50 mL); dried over anhydrous Na$_2$SO$_4$, filtered and concentrated under reduced pressure. The residue obtained was purified using silica gel column chromatography (0-10% EtOAc in hexane) to provide desired intermediate A-44-I (0.65 g, 87% yield). $^1$H NMR (CDCl$_3$; 400 MHz) 2.15-2.23 (m, 1H); 2.52-2.61 (m, 1H); 2.91-2.99 (m, 1H); 3.12-3.20 (m, 1H); 5.74-5.77 (m, 1H); 7.02 (dd, J$_1$=2.9 Hz, J$_2$=8.8 Hz, 1H); 7.23-7.28 (aromatics, 1H); 7.30-7.36 (aromatics, 3H); 7.40 (d, J=7.3 Hz, 1H); 7.61 (d, J=8.8 Hz, 1H).

Step-2: Methyl 3-[3-[4-indan-1-yloxy-2-(trifluoromethyl)phenoxy]phenyl]propanoate (A-44-II)

A-44-II (0.032 g, 17% yield) was synthesized using Ulamann coupling reaction between A-44-I (0.15 g) and methy 3-(3-hydroxyphenyl)propionate (0.11 g) using reaction conditions as described in step-1 of synthesis of A-42. $^1$H NMR (CDCl$_3$; 400 MHz) 2.19-2.27 (m, 1H); 2.53-2.57 (m, 1H); 2.62 (t, J=7.4 Hz, 2H); 2.95 (t, J=7.8 Hz, 2H); 2.97-2.99 (m, 1H); 3.13-3.21 (m, 1H); 3.67 (s, 2H); 5.73-5.76 (m, 1H); 6.80-6.83 (aromatics, 2H); 6.93-6.96 (aromatics, 2H); 7.10 (dd, J$_1$=5.8 Hz, J$_2$=8.8 Hz, 1H); 7.22-7.34 (aromatics, 4H); 7.42 (d, J=7.3 Hz, 1H).

Step-3: 3-[3-[4-indan-1-yloxy-2-(trifluoromethyl)phenoxy]phenyl]propanoic Acid (A-44)

As described in step-2 for the synthesis of A-1 using A-44-II. LCMS: m/z; 441.3 (M-1)$^+$. $^1$H NMR (DMSO-d$_6$; 400 MHz) 2.02-2.10 (m, 1H); 2.50-2.60 (m, 3H); 2.82 (t, J=7.5 Hz, 2H); 2.86-2.94 (m, 1H); 3.02-3.10 (m, 1H); 5.92-5.96 (m, 1H); 6.77 (dd, J$_1$=2.7 Hz, J$_2$=8.1 Hz, 1H); 6.91 (bs, 1H); 7.01 (d, J=7.5 Hz, 1H); 7.07 (d, J=9.7 Hz, 1H); 7.22-7.32 (aromatics, 2H); 7.34-7.44 (aromatics, 5H); 12.11 (bs, 1H).

Synthesis of 3-[3-[4-(1H-indazol-5-yloxy)-2-(trifluoromethyl)phenoxy]phenyl]propanoic Acid (A-45)

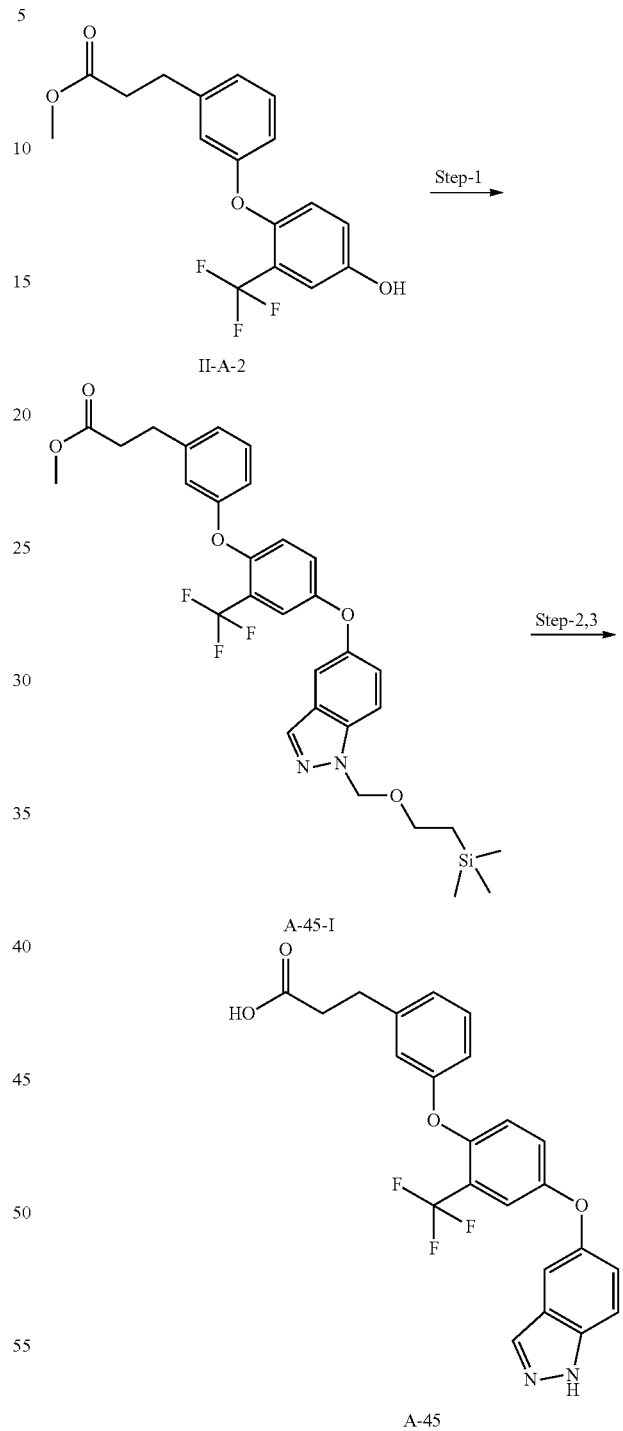

Step-1: Methyl 3-[3-[2-(trifluoromethyl)-4-[1-(2-trimethylsilylethoxymethyl)indazol-5-yl]oxy-phenoxy]phenyl]propanoate (A-45-I)

Argon was purged through a solution of II-A-2 (1 g, 2.9 mmol), 2-[(5-bromoindazol-1-yl)methoxy]ethyl-trimethylsilane (1.14 g, 3.5 mmol), picolinic acid (0.172 g, 1.4 mmol)

and $K_3PO_4$ (1.22 g, 5.8 mmol) in DMSO (10 mL) for 15 min. CuI (0.14 g, 0.72 mmol) was then added to it and purging was continued for 15 min more. The reaction mixture was then stirred at 100° C. for 16 h. It was cooled to room temperature, diluted using EtOAc (50 mL) and filtered through celite. The organic layer was then washed with water (50 mL×2); brine (50 mL); dried over anhydrous $Na_2SO_4$, filtered and concentrated under reduced pressure. The residue obtained was purified using silica gel column chromatography (0-20% EtOAc in hexane) to provide desired intermediate A-45-I (0.4 g, 23% yield). LCMS: m/z; 587 (M+1)$^+$.

Step-2, 3: 3-[3-[4-(1H-indazol-5-yloxy)-2-(trifluoromethyl)phenoxy]phenyl]propanoic Acid (A-45)

Intermediate A-45-I (0.1 g, 0.17 mmol) was dissolved in $CH_2Cl_2$ (2 mL), to which TFA (0.55 mL) was added and the reaction mixture was stirred at room temperature for 4-5 h. After completion of the reaction, dichloromethane was removed under reduced pressure. Saturated $NaHCO_3$ solution (20 mL) was added to the residue and extraction was carried out using EtOAc (20 mL×2). The combined organic layers were washed with water (30 mL); brine (30 mL); dried over anhydrous $Na_2SO_4$, filtered and concentrated under reduced pressure. The residue obtained was purified using silica gel column chromatography to provide desired intermediate (corresponding SEM de-protected intermediate) (0.031 g), which was subjected to ester hydrolysis (as described in step-2 for the synthesis of A-1) to provide A-45 (0.018 g). LCMS: m/z; 443.1 (M+1)$^+$. $^1$H NMR (DMSO-d$_6$; 400 MHz) 2.53 (t, J=7.8 Hz, 2H); 2.82 (t, J=7.8 Hz, 2H); 6.81 (dd, J$_1$=1.5 Hz, J$_2$=8.1 Hz, 1H); 6.94-6.96 (aromatics, 1H); 7.02-7.07 (aromatics, 2H); 7.19 (dd, J$_1$=2.2 Hz, J$_2$=8.8 Hz, 1H); 7.23 (dd, J$_1$=2.9 Hz, J$_2$=8.8 Hz, 1H); 7.28-7.33 (aromatics, 2H); 7.46 (d, J=1.9 Hz, 1H); 7.61 (d, J=8.8 Hz, 1H); 8.05 (s, 1H); 12.02 (bs, 1H); 13.20 (bs, 1H).

Following compound was synthesized using similar scheme and procedure as described for the synthesis of A-45.

| No. | Structure (IUPAC name) | Analytical data |
|---|---|---|
| A-46 | 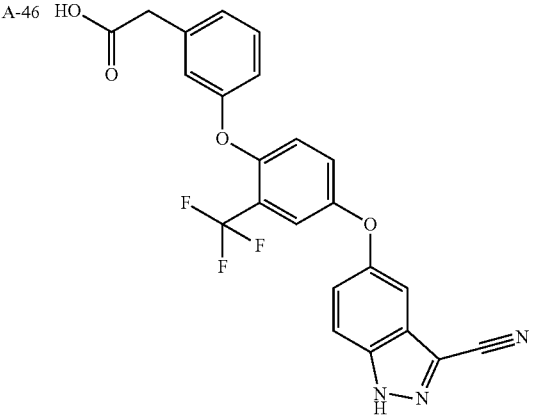<br>2-[3-[4-[3-cyano-1H-indazol-5-yl)oxy]-2-(trifluoromethyl)phenoxy]phenyl]acetic acid | LCMS: m/z; 454.1 (M + 1)$^+$. $^1$H NMR (DMSO-d$_6$; 400 MHz) 3.60 (s, 2H); 6.92 (d, J = 7.8 Hz, 1H); 7.00 (s, 1H); 7.07-7.11 (aromatics, 2H); 7.31-7.42 (aromatics, 3H); 7.45 (d, J = 3.0 Hz, 1H); 7.54 (s, 1H); 7.84 (d, J = 9.3 Hz, 1H); 12.38 (bs, 1H); 14.45 (bs, 1H). |
| A-47 | 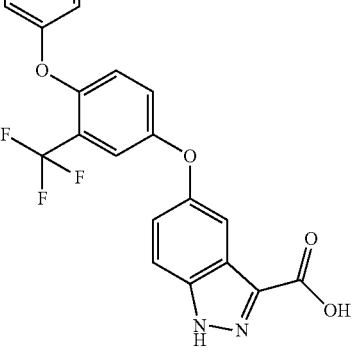<br>5-[4-[3-(carboxymethyl)phenoxy]-3-(trifluoromethyl)phenoxy]-1H-indazole-3-carboxylic acid | LCMS: m/z; 473.1 (M + 1)$^+$. $^1$H NMR (DMSO-d$_6$; 400 MHz) 3.59 (s, 2H); 6.88-6.91 (m, 1H); 6.98 (bs, 1H); 7.08 (t, J = 9.2 Hz, 2H); 7.26-7.30 (m, 2H); 7.34 (t, J = 8.0 Hz, 1H); 7.40 (d, J = 1.2 Hz, 1H); 7.63 (bs, 1H); 7.72 (d, J = 9.2 Hz, 1H); 12.25-12.80 (bs, 2H); 13.90 (bs, 1H). |

Synthesis of 2-[3-[4-(1H-indazol-4-yloxy)-2-(trifluoromethyl)phenoxy]phenyl]acetic Acid (A-48)

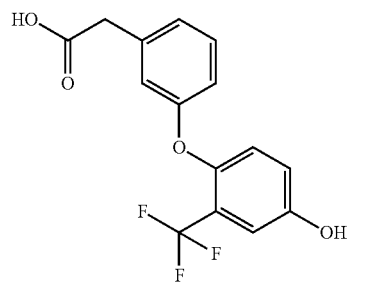

II-B-1

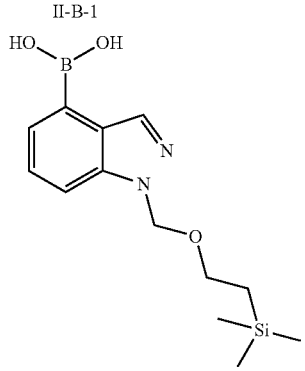

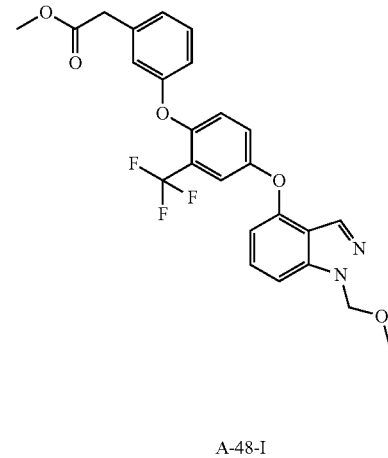

A-48

Step-1: Methyl 2-[3-[2-(trifluoromethyl)-4-[1-(2-trimethylsilylethoxymethyl)indazol-4-yl]oxy-phenoxy]phenyl]acetate (A-48-I)

To a solution of II-B-1 (0.4 g, 0.77 mmol), [1-(2-trimethylsilylethoxymethyl)indazol-4-yl]boronic acid (0.44 g, 1.5 mmol), pyridine (0.3 mL, 3.8 mmol) in $CH_2Cl_2$ (6 mL) was added and copper(II) acetate (0.13 g, 0.77 mmol) and 4 A° molecular sieves (0.1 g); and the reaction mixture was stirred at room temperature for 48 h. It was then diluted using $CH_2Cl_2$ (50 mL) and washed with water (50 mL) and brine (50 mL). The combined organic layers were then dried over anhydrous $Na_2SO_4$, filtered and concentrated under reduced pressure. The residue was purified using silica gel column chromatography (0-10% EtOAc in hexane) to provide desired intermediate A-48-I (0.55 g, 78% yield). LCMS: m/z; 573.2 $(M+1)^+$.

Step-2, 3: 2-[3-[4-(1H-indazol-4-yloxy)-2-(trifluoromethyl)phenoxy]phenyl]acetic Acid (A-48)

As described in step-2, 3 for the synthesis of A-45. 0.1 g A-48 obtained from 0.55 g of A-48-I. LCMS: m/z; 429.2 $(M+1)^+$. $^1$H NMR (DMSO-$d_6$; 400 MHz) 3.61 (s, 2H); 6.60 (dd, $J_1$=1.5 Hz, $J_2$=6.9 Hz, 1H); 6.94 (dd, $J_1$=1.7 Hz, $J_2$=8.1 Hz, 1H); 7.02-7.04 (aromatics, 1H); 7.08-7.13 (aromatics, 2H); 7.29-7.41 (aromatics, 4H); 7.52 (d, J=2.9 Hz, 1H); 7.94 (d, J=0.5 Hz, 1H); 12.38 (bs, 1H); 13.30 (bs, 1H).

Synthesis of 2-[3-[4-imidazo[1,5-a]pyridin-5-yloxy-2-(trifluoromethyl)phenoxy]phenyl]acetic Acid (B-1)

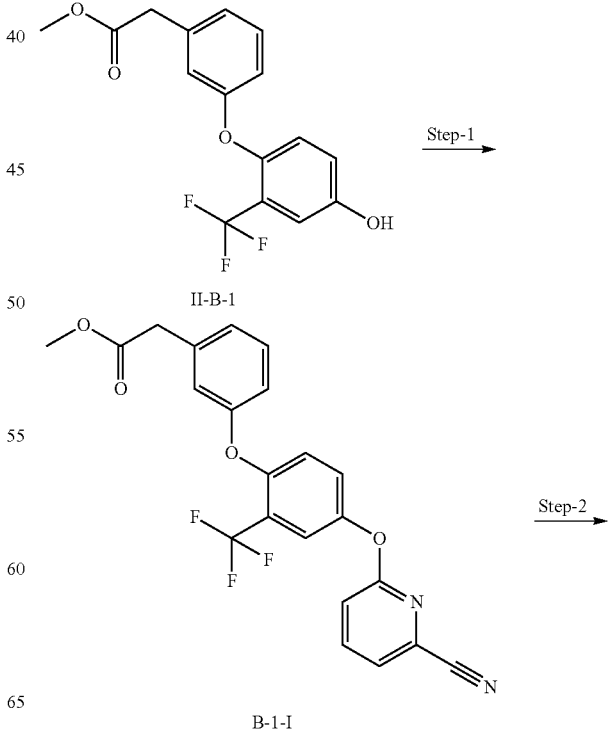

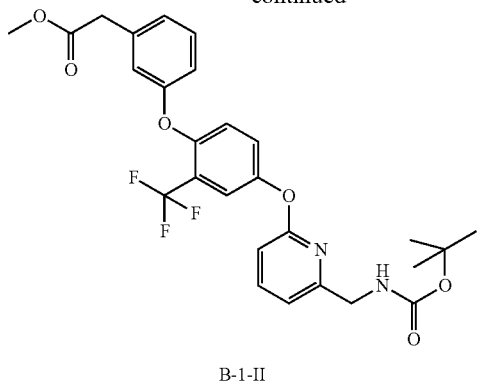

B-1-II

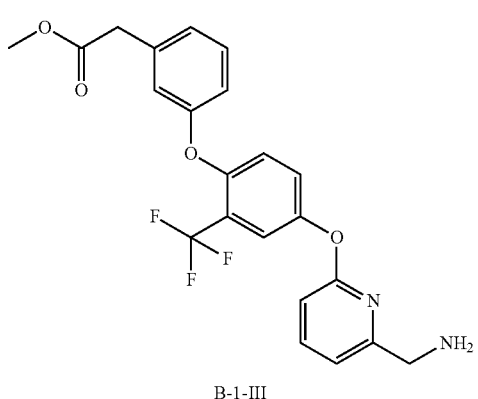

B-1-III

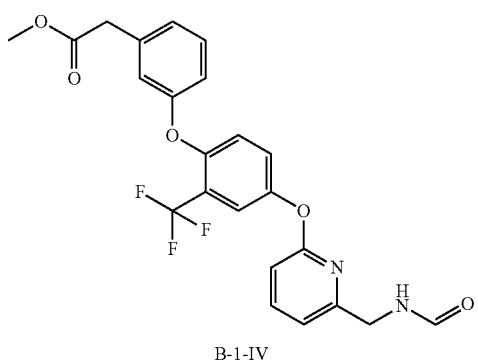

B-1-IV

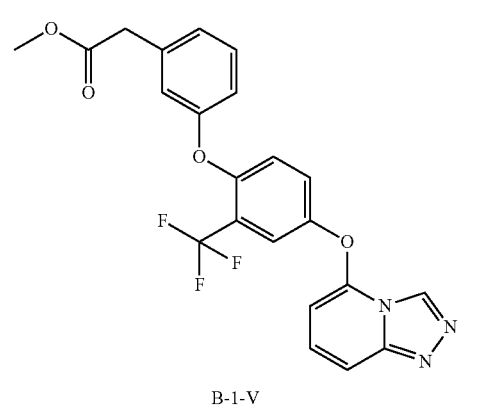

B-1-V

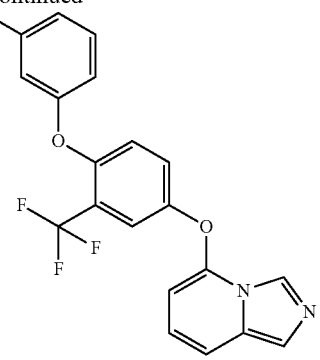

B-1

Step-1: methyl 2-[3-[4-[(6-cyano-2-pyridyl)oxy]-2-(trifluoromethyl)phenoxy]phenyl]acetate (B-1-I)

A solution of II-B-1 (1.2 g, 3.7 mmol), 6-fluoropyridine-2-carbonitrile (0.67 g, 5.5 mmol) and $Cs_2CO_3$ (2.4 g, 7.4 mmol) in DMF (10 mL) was stirred at 90° C. for 1 h. After completion of the reaction, it was cooled to room temperature and diluted using water (50 mL). Extraction was carried out using EtOAc (30 mL×3); the combined organic layers were washed with water (50 mL×2); brine (50 mL); dried over anhydrous $Na_2SO_4$, filtered and concentrated under reduced pressure. The residue obtained was purified using silica gel column chromatography (0-40% EtOAc in hexane) to provide desired intermediate B-1-I (1.25 g, 79%). LCMS: m/z; 428.9 (M+1)+. $^1$H NMR ($CDCl_3$; 400 MHz) 3.64 (s, 2H); 3.71 (s, 3H); 6.96-7.01 (aromatics, 2H); 7.04-7.06 (aromatics, 1H); 7.10 (d, J=7.6 Hz, 1H); 7.21 (dd, $J_1$=0.8 Hz, $J_2$=8.6 Hz, 1H); 7.24-7.28 (aromatics, 1H); 7.32-7.36 (aromatics, 1H); 7.43-7.46 (aromatics, 2H); 7.84 (dd, $J_1$=7.3 Hz, $J_2$=8.4 Hz, 1H).

Step-2: Methyl 2-[3-[4-[[6-[(tert-butoxycarbonylamino)methyl]-2-pyridyl]oxy]-2-(trifluoromethyl)phenoxy]phenyl]acetate (B-1-II)

A solution of B-1-I (1.15 g, 2.7 mmol), 10% Pd/C (0.17 g) and $(Boc)_2O$ (1.8 mL, 8.06 mmol) in MeOH (15 mL) was stirred under hydrogen atmosphere (bladder pressure) for 4-5 h. After completion of the reaction, the catalyst was filtered off through celite and washed with MeOH (10 mL×3). The combined organic layers were concentrated under reduced pressure and the residue was purified using silica gel column chromatography (0-40% EtOAc in hexane) to provide desired intermediate B-1-II (1.15 g, 80% yield). LCMS: m/z; 533 (M+1)+.

Step-3: Methyl 2-[3-[4-[[6-(aminomethyl)-2-pyridyl]oxy]-2-(trifluoromethyl)phenoxy]phenyl] acetate (B-1-III)

To a solution of intermediate B-1-II (1.15 g) in dioxane (15 mL) was added a solution of 4M HCl in dioxane (15 mL). It was stirred at room temperature for 4-5 h. After completion of the reaction, dioxane was removed under reduced pressure and the residue was made alkaline using saturated $NaHCO_3$ solution (30 mL). Extraction was carried out using EtOAc (30 mL×3); the combined organic layers were washed with water (50 mL×2); brine (50 mL); dried over anhydrous $Na_2SO_4$, filtered and concentrated under reduced pressure. The residue obtained was purified using silica gel column chromatography (0-5% MeOH in dichloromethane) to provide desired intermediate B-1-III (0.65 g, 69%).LCMS: m/z; 432.9 (M+1)+. $^1$H NMR ($CDCl_3$; 400 MHz) 3.63 (s, 2H); 3.71 (s, 3H); 3.85 (s, 2H); 6.76 (d, J=8.4

Hz, 1H); 6.92-7.02 (aromatics, 4H); 7.07 (d, J=7.8 Hz, 1H); 7.24-7.27 (aromatics, 1H); 7.29-7.34 (aromatics, 1H); 7.49 (d, J=2.9 Hz, 1H); 7.65-7.69 (aromatics, 1H).

Step-4: Methyl 2-[3-[4-[[6-(formamidomethyl)-2-pyridyl]oxy]-2-(trifluoromethyl)phenoxy]phenyl]acetate (B-1-IV)

To a solution of B-1-III (0.65 g, 1.5 mmol), formic acid (0.17 mL, 4.5 mmol) and DIPEA (1 mL, 6 mmol) in DMF (6 mL) was added HATU (1.13 g, 2 mmol). The reaction mixture was stirred at room temperature for 16 h, before it was diluted with water (30 mL). Extraction was carried out using EtOAc (30 mL×3); the combined organic layers were washed with water (50 mL×2); brine (50 mL); dried over anhydrous $Na_2SO_4$, filtered and concentrated under reduced pressure. The residue obtained was purified using silica gel column chromatography (0-5% MeOH in dichloromethane) to provide desired intermediate B-1-IV (0.6 g, 86%).LCMS: m/z; 460.9 $(M+1)^+$. $^1$H NMR ($CDCl_3$; 400 MHz) 3.62 (s, 2H); 3.68 (s, 3H); 4.49 (d, J=5.4 Hz, 2H); 6.80 (d, J=8.3 Hz, 1H); 6.92-7.99 (aromatics, 4H); 7.06 (d, J=8.0 Hz, 1H); 7.21-7.27 (aromatics, 1H); 7.29-7.33 (aromatics, 1H); 7.47 (d, J=2.7 Hz, 1H); 7.67-7.71 (aromatics, 1H); 8.22 (bs, 1H).

Step-5: Methyl 2-[3-[4-imidazo[1,5-a]pyridin-5-yloxy-2-(trifluoromethyl)phenoxy]phenyl]acetate (B-1-V)

A solution of intermediate B-1-IV (0.4 g, 0.87 mmol), $POCl_3$ (0.25 mL, 2.6 mmol) in toluene (3 mL) was stirred at 50° C. for 1 h. After completion of the reaction, toluene was removed under reduced pressure and saturated $NaHCO_3$ solution (20 mL) was added to the residue. Extraction was carried out using EtOAc (20 mL×3); the combined organic layers were washed with water (50 mL×2); brine (50 mL); dried over anhydrous $Na_2SO_4$, filtered and concentrated under reduced pressure. The residue obtained was purified using silica gel column chromatography (0-2% MeOH in dichloromethane) to provide desired intermediate B-1-V (0.28 g, 73%).LCMS: m/z; 443 $(M+1)^+$.

Step-6: 2-[3-[4-imidazo[1,5-a]pyridin-5-yloxy-2-(trifluoromethyl)phenoxy]phenyl]acetic Acid (B-1)

As described in step-2 for the synthesis of A-1. 0.37 g of B-1 obtained from 0.5 g of B-1-V. LCMS: m/z; 429.1 $(M+1)^+$. $^1$H NMR (DMSO-$d_6$; 400 MHz) 3.62 (s, 2H); 5.95 (d, J=7.1 Hz, 1H); 6.78-6.82 (aromatics, 1H); 6.98 (dd, $J_1$=2.0 Hz, $J_2$=7.8 Hz, 1H); 7.04-7.06 (aromatics, 1H); 7.11-7.17 (aromatics, 2H); 7.35-7.40 (aromatics, 2H); 7.49 (s, 1H); 7.65 (dd, $J_1$=2.9 Hz, $J_2$=9.1 Hz, 1H); 7.87 (d, J=2.9 Hz, 1H); 8.47 (s, 1H); 12.29 (bs, 1H).

Following compounds were synthesized using similar synthetic scheme and experimental procedures as described for the synthesis of B-1.

| No. | Structure (IUPAC name) | Analytical data |
|---|---|---|
| B-2 | 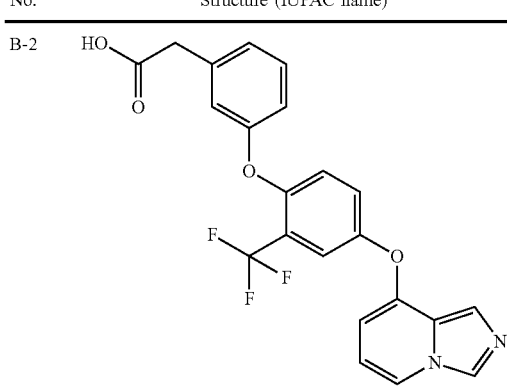<br>2-[3-[4-imidazo[1,5-a]pyridin-8-yloxy-2-(trifluoromethyl)phenoxy]phenyl]acetic acid | LCMS: m/z; 428.9 $(M + 1)^+$. $^1$H NMR (DMSO-$d_6$; 400 MHz) 3.61 (s, 2H); 6.20 (d, J = 7.2 Hz, 1H); 6.59-6.63 (aromatics, 1H); 6.95 (dd, $J_1$ = 2.2 Hz, $J_2$ = 7.8 Hz, 1H); 7.01-7.03 (aromatics, 1H); 7.09-7.13 (aromatics, 2H); 7.34-7.38 (aromatics, 2H); 7.48 (dd, $J_1$ = 3.0 Hz, $J_2$ = 8.9 Hz, 1H); 7.62 (d, J = 3.0 Hz, 1H); 8.17 (d, J = 7.0 Hz, 1H); 8.47 (s, 1H); 12.38 (bs, 1H). |
| B-3 | 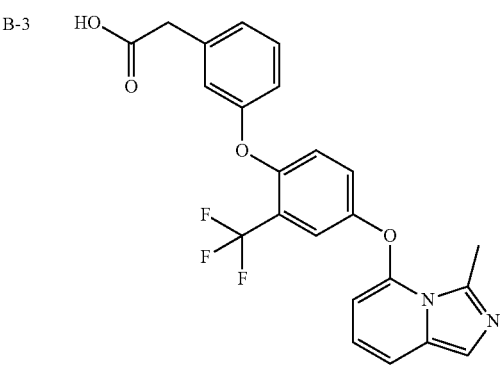<br>2-[3-[4-(3-methylimidazo[1,5-a]pyridin-5-yl)oxy-2-(trifluoromethyl)phenoxy]phenyl]acetic acid | LCMS: m/z; 443.2 $(M + 1)^+$. $^1$H NMR (DMSO-$d_6$; 400 MHz) 2.83 (s, 3H); 3.60 (s, 2H); 5.77 (d, J = 6.6 Hz, 1H); 6.61 (dd, $J_1$ = 7.1 Hz, $J_2$ = 9.1 Hz, 1H); 6.97 (d, J = 8.1 Hz, 1H); 7.04 (s, 1H); 7.11 (d, J = 7.1 Hz, 1H); 7.15 (d, J = 9.1 Hz, 1H); 7.21 (d, J = 8.8 Hz, 1H); 7.26 (s, 1H); 7.34-7.39 (aromatics, 1H); 7.60 (dd, $J_1$ = 2.7 Hz, $J_2$ = 9.3 Hz, 1H); 7.82 (d, J = 2.7 Hz, 1H); 12.50 (bs, 1H). |

| No. | Structure (IUPAC name) | Analytical data |
|---|---|---|
| B-4 | 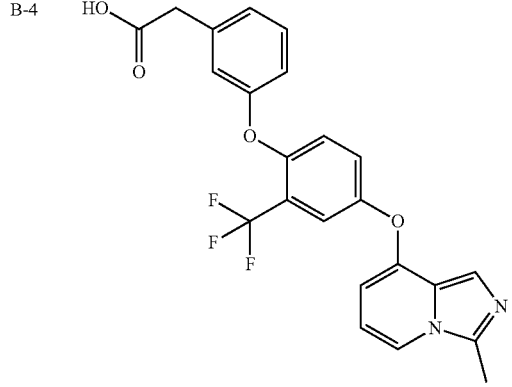<br>2-[3-[4-(3-methylimidazo[1,5-a]pyridin-8-yl)oxy-2-(trifluoromethyl)phenoxy]phenyl]acetic acid | LCMS: m/z; 443.1 (M + 1)$^+$. $^1$H NMR (DMSO-$d_6$; 400 MHz) 2.62 (s, 3H); 3.61 (s, 2H); 6.20 (d, J = 7.1 Hz, 1H); 6.61-6.65 (aromatics, 1H); 6.94 (dd, $J_1$ = 1.9 Hz, $J_2$ = 8.0 Hz, 1H); 7.00-7.02 (aromatics, 1H); 7.08-7.12 (aromatics, 2H); 7.29 (s, 1H); 7.34-7.38 (aromatics, 1H); 7.45 (dd, $J_1$ = 2.9 Hz, $J_2$ = 9.1 Hz, 1H); 7.59 (d, J = 2.9 Hz, 1H); 7.93 (d, J = 7.1 Hz, 1H); 12.38 (bs, 1H). |
| B-5 | 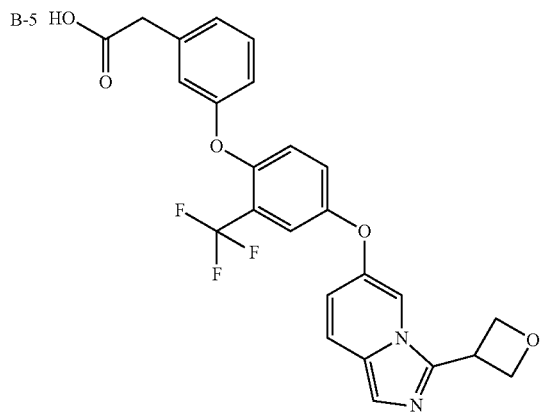<br>2-[3-[4-[3-(oxetan-3-yl)imidazo[1,5-a]pyridin-6-yl]oxy-2-(trifluoromethyl)phenoxy]phenyl]acetic acid | Note: i) $T_3P$ used for acid-amine coupling in step-4; ii) Burgess reagent used for cyclisation in step-5.<br>LCMS: m/z; 485.1 (M + 1)$^+$. $^1$H NMR (DMSO-$d_6$; 400 MHz) 3.59 (s, 2H); 3.47-3.48 (m, 1H); 4.87-4.97 (m, 4H); 6.70 (dd, $J_1$ = 1.4 Hz, $J_2$ = 9.7 Hz, 1H); 6.88 (dd, $J_1$ = 2.0 Hz, $J_2$ =7.9 Hz, 1H); 6.96 (s, 1H); 7.06-7.10 (aromatics, 2H); 7.31-7.36 (aromatics, 2H); 7.43 (d, J = 2.9 Hz, 1H); 7.48 (s, 1H); 7.66 (d, J = 9.3 Hz, 1H); 8.20 (s, 1H); 12.38 (bs, 1H). |

109

Synthesis of 2-[3-[4-(8-isoquinolyloxy)-2-(trifluoromethyl)phenoxy]phenyl]-N-methylsulfonyl-acetamide (C-1)

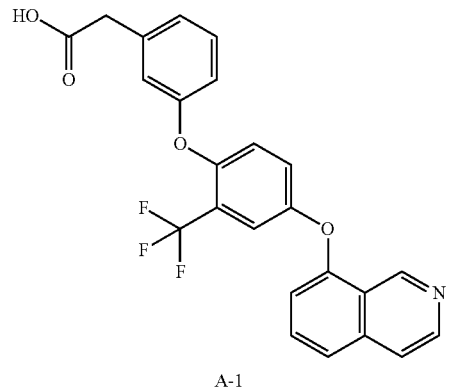

A-1

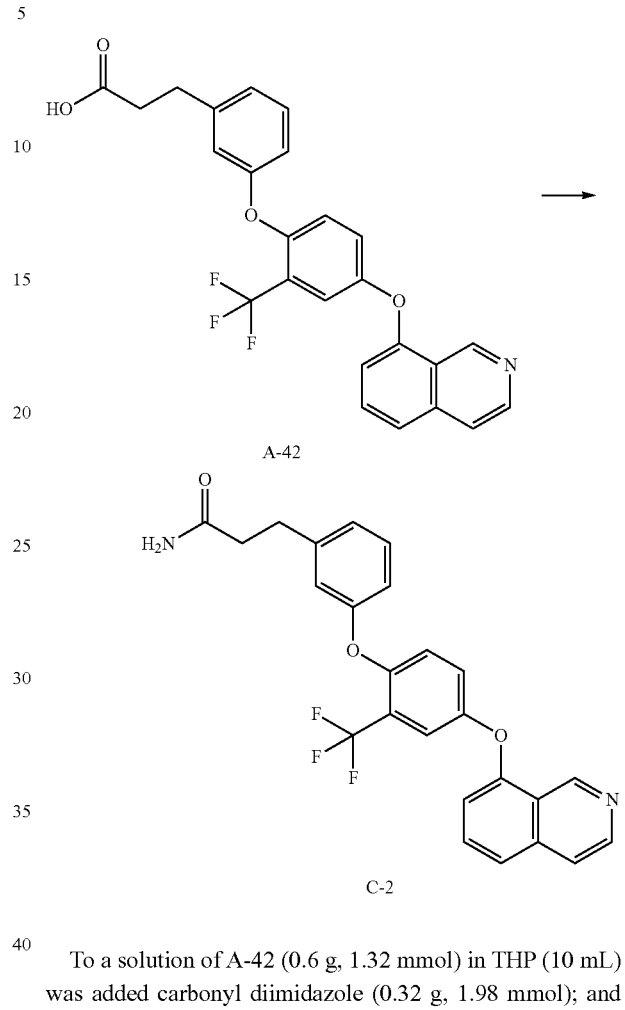

C-1

To a solution of A-1 (0.2 g, 0.45 mmol), methane sulfonamide (0.051 g, 0.54 mmol) and DMAP (0.219 g, 1.8 mmol) in $CH_2Cl_2$ (3 mL) was added EDC-HCl (0.083 g, 0.54 mmol) and the reaction mixture was stirred at room temperature for 16 h. After completion of the reaction, it was diluted using water and extraction was carried out using $CH_2Cl_2$ (15 mL×3). The combined organic layers were washed with water (30 mL); brine (30 mL); dried over anhydrous $Na_2SO_4$, filtered and concentrated under reduced pressure. The residue obtained was purified using silica gel column chromatography (0-4% MeOH in $CH_2Cl_2$) to provide desired compound C-1 (0.06 g, 25% yield). LCMS: m/z; 517.2 (M+1)$^+$. $^1$H NMR (DMSO-d$_6$; 400 MHz) 3.23 (s, 3H); 3.65 (s, 2H); 6.99 (dd, $J_1$=1.9 Hz, $J_2$=8.1 Hz, 1H); 7.03 (s, 1H); 7.07-7.10 (aromatics, 2H); 7.16 (d, J=9.1 Hz, 1H); 7.36-7.42 (aromatics, 1H); 7.48 (dd, $J_1$=2.9 Hz, $J_2$=9.1 Hz, 1H); 7.67 (d, J=2.7 Hz, 1H); 7.70-7.74 (aromatics, 2H); 7.90 (d, J=5.6 Hz, 1H); 8.61 (d, J=5.7 Hz, 1H); 9.58 (s, 1H); 11.98 (bs, 1H).

110

Synthesis of 3-[3-[4-(8-isoquinolyloxy)-2-(trifluoromethyl)phenoxy]phenyl]propanamide (C-2)

A-42

C-2

To a solution of A-42 (0.6 g, 1.32 mmol) in THP (10 mL) was added carbonyl diimidazole (0.32 g, 1.98 mmol); and the reaction mixture was stirred at 45° C. for 2 h. It was the cooled to 0° C. and ammonium carbonate (1.27 g, 13.2 mmol) was added it. The reaction mixture was stirred at room temperature before it was diluted using water (30 mL). Extraction was carried out using EtOAc (30 mL×3); the combined organic layers were washed with water (50 mL×2); brine (50 mL); dried over anhydrous $Na_2SO_4$, filtered and concentrated under reduced pressure. The residue obtained was purified using silica gel column chromatography (0-2% MeOH in dichloromethane) to provide desired compound C-2 (0.55 g, 92% yield).LCMS: m/z; 453.2 (M+1)$^+$. $^1$H NMR (DMSO-d$_6$; 400 MHz) 2.36 (t, J=7.4 Hz, 2H); 2.82 (t, J=7.9 Hz, 2H); 6.77 (bs, 1H); 6.88 (dd, $J_1$=1.9 Hz, $J_2$=8.2 Hz, 1H); 6.98-7.01 (aromatics, 1H); 7.02-7.14 (aromatics, 3H); 7.28 (bs, 1H); 7.31-7.35 (aromatics, 1H); 7.47 (dd, $J_1$=2.5 Hz, $J_2$=8.8 Hz, 1H); 7.66 (d, J=3.0 Hz, 1H); 7.70-7.76 (aromatics, 2H); 7.90 (d, J=5.4 Hz, 1H); 8.61 (d, J=5.8 Hz, 1H); 9.58 (s, 1H).

Following compound was synthesized using similar procedure as described for the synthesis of C-2.

| No. | Structure (IUPAC name) | Analytical data |
|---|---|---|
| C-3 | 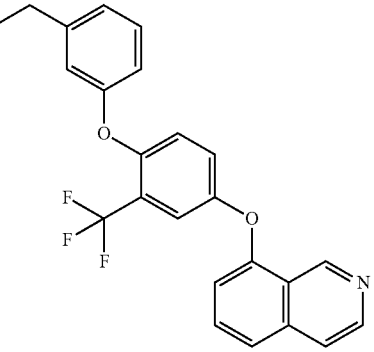

2-[3-[4-(8-isoquinolyloxy)-2-(trifluoromethyl)phenoxy]phenyl]acetamide | LCMS: m/z; 439.1 (M + 1)$^+$. $^1$H NMR (CDCl$_3$; 400 MHz) 3.59 (s, 2H); 5.41 (bs, 2H); 6.94 (dd, J$_1$ = 2.1 Hz, J$_2$ = 6.5 Hz, 1H); 6.95-7.04 (aromatics, 3H); 7.08 (d, J = 8.1 Hz, 1H); 7.24 (dd, J$_1$ = 2.7 Hz, J$_2$ = 8.6 Hz, 1H); 7.34-7.39 (aromatics, 1H); 7.47 (d, J = 3.0 Hz, 1H); 7.59-7.61 (aromatics, 2H); 7.69 (dd, J$_1$ = 0.8 Hz, J$_2$ = 5.6 Hz, 1H); 8.62 (d, J = 5.7 Hz, 1H); 9.64 (s, 1H). |

Synthesis of 8-[4-[3-[2-(4H-1,2,4-triazol-3-yl)ethyl]phenoxy]-3-(trifluoromethyl)phenoxy]isoquinoline (D-1)

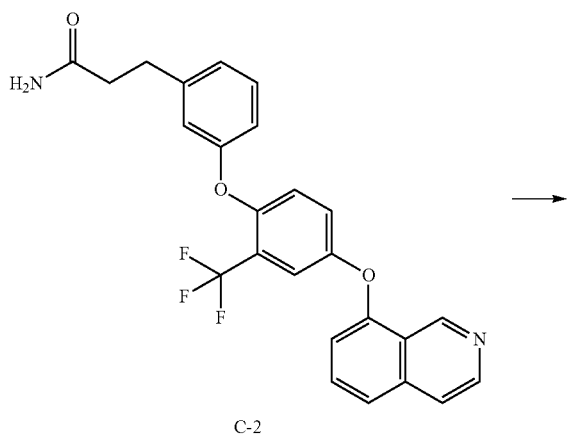

C-2 (0.26 g, 0.57 mmol) was stirred in dimethylformamide-dimethylacetal (0.34 g, 2.87 mmol) at 120° C. for 1.5 h. Volatiles were removed under reduced pressure and the residue was stirred at 90° C. in AcOH (3 mL). It was cooled to room temperature and diluted with 2M NaOH solution. Extraction was carried out using EtOAc (15 mL×3). The combined organic layers were washed with water (30 mL); brine (30 mL); dried over anhydrous Na$_2$SO$_4$, filtered and concentrated under reduced pressure. The residue obtained was purified using silica gel column chromatography (0-3% MeOH in CH$_2$Cl$_2$) to provide desired compound D-1 (0.07 g, 25% yield). LCMS: m/z; 477.2 (M+1)$^+$. $^1$H NMR (DMSO-d$_6$; 400 MHz) 2.90-3.04 (m, 4H); 6.94-6.98 (aromatics, 2H); 7.04-7.08 (aromatics, 3H); 7.30-7.38 (aromatics, 1H); 7.46-7.50 (aromatics, 1H); 7.65 (d, J=2.4 Hz, 1H); 7.70-7.79 (aromatics, 3H); 7.90 (d, J=5.9 Hz, 1H); 8.61 (d, J=5.9 Hz, 1H); 13.50-13.60 (m, 1H).

Synthesis of 8-[4-[3-[2-(1H-tetrazol-5-yl)ethyl]phenoxy]-3-(trifluoromethyl)phenoxy]isoquinoline (D-2)

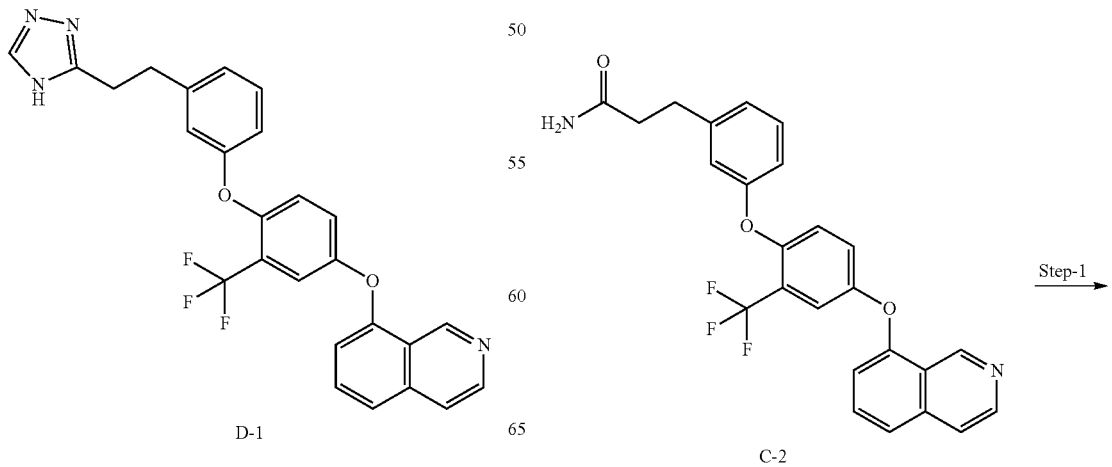

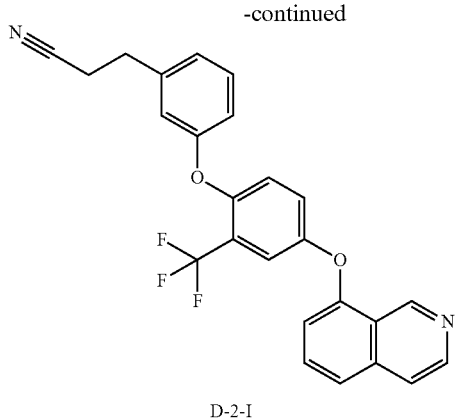

D-2-I

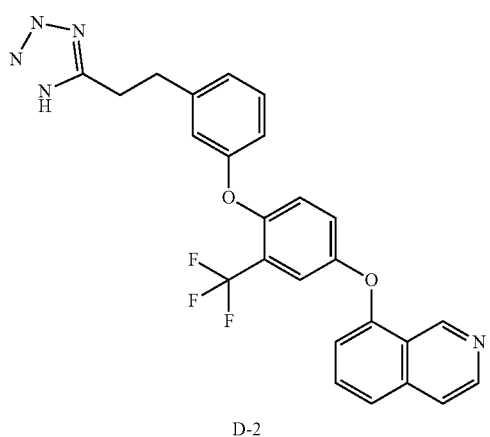

D-2

Step-1: 3-[3-[4-(8-isoquinolyloxy)-2-(trifluoromethyl)phenoxy]phenyl]propanenitrile (D-2-I)

To a solution of C-2 (0.27 g, 0.59 mmol) in anhydrous THF (4 mL) was added trifluoroacetic anhydride (0.19 g, 0.89 mmol) and triethyl amine (0.18 g, 1.8 mmol) sequentially at 0° C. The reaction mixture was stirred at 0° C. for 1 h and at room temperature for 1 h, before it was dilute using water (20 mL). Extraction was carried out using EtOAc (15 mL×3). The combined organic layers were washed with water (30 mL); brine (30 mL); dried over anhydrous $Na_2SO_4$, filtered and concentrated under reduced pressure. The residue obtained was purified using silica gel column chromatography (0-5% MeOH in $CH_2Cl_2$) to provide desired intermediate D-2-I (0.22 g, 85% yield). LCMS: m/z; 435 (M+1)$^+$.

Step-2: 8-[4-[3-[2-(1H-tetrazol-5-yl)ethyl]phenoxy]-3-(trifluoromethyl)phenoxy]isoquinoline (D-2)

A solution of D-2-I (0.22 g, 0.5 mmol), ammonium chloride (0.4 g, 7.6 mmol) and sodium azide (0.49 g, 7.6 mmol) in DMF (8 mL) was stirred at 90-100° C. for 18 h. After completion of the reaction, it was cooled to room temperature and diluted using water (30 mL). Extraction was carried out using EtOAc (20 mL×3). The combined organic layers were washed with water (30 mL); brine (30 mL); dried over anhydrous $Na_2SO_4$, filtered and concentrated under reduced pressure. The residue obtained was purified using silica gel column chromatography (0-5% MeOH in $CH_2Cl_2$) to provide desired compound D-2 (0.12 g, 49% yield). LCMS: m/z; 478.2 (M+1)$^+$. $^1$H NMR (DMSO-$d_6$; 400 MHz) 3.06 (t, J=7.8 Hz, 2H); 3.21 (t, J=7.8 Hz, 2H); 6.91 (dd, J=2.0 Hz, $J_2$=7.8 Hz, 1H); 6.96 (bs, 1H); 7.05-7.09 (aromatics, 3H); 7.31-7.38 (aromatics, 1H); 7.46 (dd, $J_1$=2.9 Hz, $J_2$=8.8 Hz, 1H); 7.66 (d, J=3.0 Hz, 1H); 7.71-7.77 (aromatics, 2H); 7.91 (d, J=5.8 Hz, 1H); 8.61 (d, J=5.4 Hz, 1H); 9.58 (s, 1H); 16.0 (bs, 1H).

Following compound was synthesized using similar experimental procedure as described for the synthesis of D-2.

| No. | Structure (IUPAC name) | Analytical data |
|---|---|---|
| D-3 | 8-[4-[3-(1H-tetrazol-5-ylmethyl)phenoxy]-3-(trifluoromethyl)phenoxy]isoquinoline | LCMS: m/z; 464.1 (M + 1)$^+$. $^1$H NMR (DMSO-$d_6$; 400 MHz) 4.33 (s, 2H); 6.96-7.00 (aromatics, 1H); 7.05-7.09 (aromatics, 3H); 7.16 (d, J = 8.9 Hz, 1H); 7.37-7.41 (aromatics, 1H); 7.48 (dd, $J_1$ = 2.9 Hz, $J_2$ = 9.1 Hz, 1H); 7.67 (d, J = 2.9 Hz, 1H); 7.71-7.76 (aromatics, 2H); 7.90 (d, J = 5.9 Hz, 1H); 8.62 (d, J = 5.6 Hz, 1H); 9.58 (s, 1H); 16.20 (bs, 1H). |

Synthesis of 2-[3-[4-(8-isoquinolyloxy)-3-(trifluoromethyl)phenoxy]phenyl]acetic Acid (E-1)

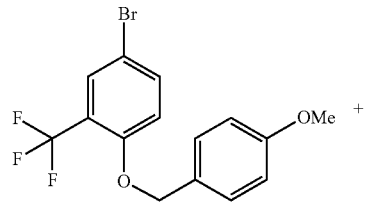

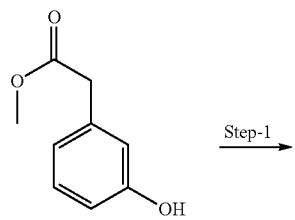

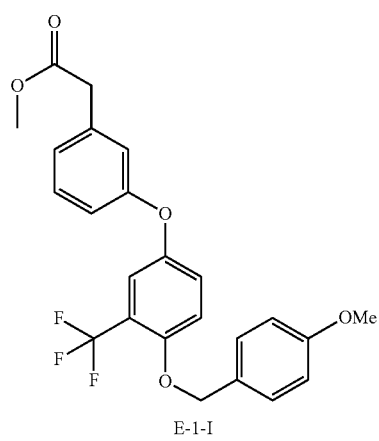

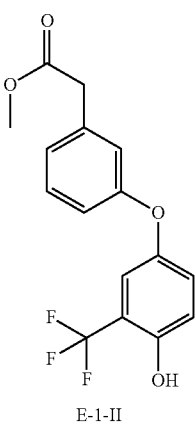

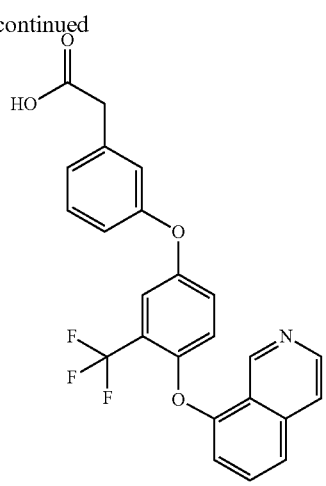

Step-1: methyl 2-[3-[4-[(4-methoxyphenyl)methoxy]-3-(trifluoromethyl)phenoxy]phenyl]acetate (E-1-I)

E-1-I (1.4 g, 58% yield) was synthesized using Ulmann coupling reaction between methyl-2-(3-hyroxyphenyl)acetate (1.2 g, 7.2 mmol) and 4-bromo-1-[(4-methoxyphenyl)methoxy]-2-(trifluoromethyl)benzene (2 g, 5.54 mmol), following procedure as described for the synthesis of II-B-4a. Here, CuI (0.25 equivalent) was used as the catalyst and 1,4-dioxane was used as the solvent. $^1$H NMR (CDCl$_3$; 400 MHz) 3.60 (s, 2H); 3.70 (s, 3H); 3.82 (s, 3H); 5.10 (s, 2H); 6.82-6.85 (aromatics, 1H); 6.88-6.90 (aromatics, 1H); 6.91-6.94 (aromatics, 2H); 6.98-7.04 (aromatics, 2H); 7.12 (dd, J$_1$=3.0 Hz, J$_2$=9.2 Hz, 1H); 7.25-7.29 (aromatics, 2H); 7.35-7.39 (aromatics, 2H).

Step-2: methyl 2-[3-[4-hydroxy-3-(trifluoromethyl)phenoxy]phenyl]acetate (E-1-II)

To a solution of E-1-I (1.4 g) in CH$_2$Cl$_2$ (10 mL) was added TFA (10 mL, excess) at 0° C. and stirred for 10-15 min. After completion of the reaction, solvents were removed under reduced pressure and saturated NaHCO$_3$ solution (50 mL) was added to the residue. Extraction was carried out using EtOAc (30 mL×3); the combined organic layers were washed with water (50 mL); brine (50 mL); dried over anhydrous Na$_2$SO$_4$, filtered and concentrated under reduced pressure. The residue obtained was purified using silica gel column chromatography (0.15% EtOAc in hexane) to provide desired intermediate E-1-II (0.8 g, 80% yield). $^1$H NMR (CDCl$_3$; 400 MHz) 3.60 (s, 2H); 3.70 (s, 3H); 6.82-6.85 (aromatics, 1H); 6.88-6.90 (aromatics, 1H); 6.93 (d, J=8.8 Hz, 1H); 7.01 (d, J=7.3 Hz, 1H); 7.10 (dd, J$_1$=3.0 Hz, J$_2$=8.8 Hz, 1H); 7.19 (d, J=2.9 Hz, 1H); 7.29 (d, J=7.9 Hz, 1H).

Step-3, 4: 2-[3-[4-(8-isoquinolyloxy)-3-(trifluoromethyl)phenoxy]phenyl]acetic Acid (E-1)

E-1 was synthesized following similar reaction conditions as described in step-1,2 for the synthesis of A-1 (25 mol % of CuI was used as the catalyst and DMF as the solvent for Ulmann coupling). LCMS: m/z; 440.1 (M+1)$^+$. $^1$H NMR (DMSO-d$_6$; 400 MHz) 3.62 (s, 2H); 7.00-7.11 (aromatics, 4H); 7.34-7.40 (aromatics, 3H); 7.49 (s, 1H); 7.72-7.76 (aromatics, 2H); 7.92 (d, J=5.9 Hz, 1H); 8.63 (d, J=5.9 Hz, 1H); 9.54 (s, 1H); 12.38 (bs, 1H).

Example 3

Biological Assay
Human GPR91 Calcium Mobilization Assay

To determine $IC_{50}$ in CHO NFAT cells over expressing human GPR91 receptor calcium mobilization assay in flex station mode was carried out.

Tissue Culture

Grow CHO-K1 NFAT cells over expressing human GPR91 receptors in alpha MEM media were supplemented with 10% FBS (heat inactivated), 0.5 mg/ml of G-418, 0.5 mg/ml of Zeocin and 0.6 mg/ml of Hygromycin B.

The cells were seeded at least 21 hours before the experiment at the density of 25000/well in 96 well plate (Corning cat #no. 3603). It was made sure that cells were at least 95% confluent on the day of assay. No antibiotics were used for seeding purpose.

Dye Loading (Fluo4, AM)

On the day of assay the media was discarded from plates and plates were washed with 100 µl of HBSS assay buffer. The plates were loaded with Fluo4 AM at 2 µM concentration. Pluronic F-127 dye was solubilized in calcium assay buffer containing 0.1% BSA, i.e., 20 µl dye+20 µl Pluronic F127 for 10 ml. Appropriate amounts of 100× probenecid was added to the loading mixture 1× final (100 µl per 10 ml). Total volume of dye loaded was made 100 µl. The plate was then wrapped in aluminium foil to protect from light and were incubated for 90 mins at 37 degrees in cell culture incubator. At the end of incubation the plates was washed again with 100 µl of HBSS buffer without BSA and 75 µl of HBSS buffer was added (without BSA) to the plate.

Further, 8 point-Dose response curve of the compounds of the present disclosure was prepared in 100% DMSO followed by 57.14-fold dilution to 1.75× in 1.75% DMSO in assay buffer. 100 µL of 1.75×NCE was added to the wells as shown below and incubated at room temp on orbital shaker at 300 rpm for 15 min. Flexstation [excitation @ 485 nm and emission @ 525 nm] for a total time of 60 seconds. 25 µL of 8× agonist (800 µM sodium succinate) was added to each well using the flexstation after establishing the baseline for 20 sec, Measurement—Max-Min over 60 sec. Using the above protocol results obtained are tabulate din the Table 1 below:

TABLE 1

| Compound No. | hGPR91 $IC_{50}$ (µM)* |
| --- | --- |
| A-1 | +++ |
| A-2 | +++ |
| A-3 | +++ |
| A-4 | +++ |
| A-5 | +++ |
| A-6 | ++ |
| A-7 | + |
| A-8 | +++ |
| A-9 | +++ |
| A-10 | + |
| A-11 | + |
| A-12 | + |
| A-13 | + |
| A-14 | +++ |
| A-15 | +++ |
| A-16 | +++ |
| A-17 | + |
| A-18 | +++ |

TABLE 1-continued

| Compound No. | hGPR91 $IC_{50}$ (µM)* |
| --- | --- |
| A-19 | + |
| A-20 | +++ |
| A-21 | +++ |
| A-22 | +++ |
| A-23 | + |
| A-24 | + |
| A-25 | +++ |
| A-26 | +++ |
| A-27 | +++ |
| A-28 | +++ |
| A-29 | + |
| A-30 | + |
| A-31 | +++ |
| A-32 | + |
| A-33 | +++ |
| A-34 | +++ |
| A-35 | +++ |
| A-36 | +++ |
| A-37 | + |
| A-38 | +++ |
| A-39 | +++ |
| A-40 | +++ |
| A-41 | +++ |
| A-42 | +++ |
| A-43 | + |
| A-44 | ++ |
| A-45 | +++ |
| A-46 | +++ |
| A-47 | +++ |
| A-48 | +++ |
| B-1 | +++ |
| B-2 | +++ |
| B-3 | +++ |
| B-4 | ++ |
| B-5 | ++ |
| C-1 | NA |
| C-2 | ++ |
| C-3 | +++ |
| D-1 | + |
| D-2 | ++ |
| D-3 | ++ |
| E-1 | + |

The above mentioned compounds have potency to be developed as drugs to treat diseases or conditions associated with GPR91.

The foregoing examples provide the details about the synthesis, activities, and applications of the compounds of the present disclosure. It should be understood the following is representative only, and that the invention is not limited by the details set forth in these examples.

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention.

Table 1 illustrates that most of the tested compounds were found to be active against the human GPR91 receptor. The $IC_{50}$ values display the efficacy of the compounds in inhibiting the human GPR91 receptor. $IC_{50}$ value indicates how much of a particular drug or a compound is needed to inhibit a given biological process or component of a process such as an enzyme. The inference drawn from the Table 1 is: + means >10 µM, ++ means 5-10 µM, +++ means <5 µM; NA means not available The above-mentioned compounds have potency to be developed as inhibitors of GPR91 useful for the treatment of disease states mediated by GPR91.

Although the subject matter has been described in considerable detail with reference to certain preferred embodiments thereof, other embodiments are possible. As such, the spirit and scope of the appended claims should not be limited to the description of the preferred embodiment contained therein.

What is claimed is:
1. Compounds of Formula (I) their tautomers, stereoisomers, and pharmaceutically acceptable salts thereof,

Formula (I)

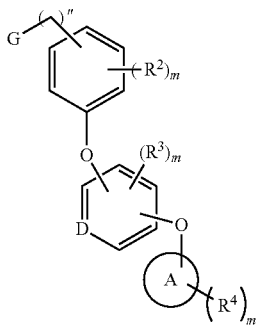

wherein
A is substituted or unsubstituted fused bicyclic or polycyclic fully or partially unsaturated heterocyclic ring having 1-5 heteroatoms independently selected from O, N, or S;
D is selected from $CR^1$, or N;
G is selected from —C(O)$OR^1$, —C(O)$NR^aR^b$, —$NR^1SO_2R^1$, or 5 membered monocyclic fully or partially unsaturated heterocyclic ring having 1-4 heteroatoms independently selected from O, N or S;
$R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl;
$R^3$ is selected from hydrogen, $C_{1-6}$ alkyl, $C_{3-6}$ cycloalkyl, $C_{2-6}$ alkenyl, $C_{2-6}$ alkynyl, $C_{1-6}$ alkoxy, C(O)$R^1$, $R^1$C(O)$NR^aR^b$, —OC(O)$R^1$, $R^6$, —$(CR^aR^b)_mC(O)R^6$, —$(CR^aR^b)_mNR^7R^8$, —$NR^aC(O)$—, —$C_{1-6}$ alkoxy C(O)$NR^aR^b$, —$SO_2NR^aR^b$—, —$NR^aC(O)NR^aR^b$, $C_{1-6}$ alkoxyamino, azido, cyano, halogen, hydroxy, $C_{1-6}$ alkylhydroxy, $C_{1-6}$ haloalkyl, perhalo $C_{1-6}$ alkyl, —C(S)$R^a$, OC(O) $C_{1-6}$ alkyloxy, $OR^aC(O)OR^b$—$C_{1-6}$ alkylOC(O)O $C_{1-6}$ alkyloxy, —$SO_3H$, —$S(O)_pR^6$, —$S(O)_2NR^7R^8 C_{1-6}$alkylthio or nitro;
$R^2$, and $R^4$ are independently selected from hydrogen, $C_{1-6}$ alkyl, $C_{3-6}$ cycloalkyl, $C_{2-6}$ alkenyl, $C_{2-6}$ alkynyl, $C_{1-6}$ alkoxy, C(O)$R^1$, $R^1$C(O)$NR^aR^b$, —OC(O)$R^1$, $R^6$, —$(CR^aR^b)_mC(O)R^6$, —$(CR^aR^b)_mNR^7R^8$, —$NR^aC(O)$—, —$C_{1-6}$ alkoxy C(O)$NR^aR^b$, —$SO_2NR^aR^b$—, $NR^aC(O)NR^aR^b$, $C_{1-6}$ alkoxyamino, azido, cyano, halogen, hydroxy, $C_{1-6}$ alkylhydroxy, $C_{1-6}$ haloalkyl, perhalo $C_{1-6}$ alkyl, —C(S)$R^a$, —C(O)$OR^1$, $C_{1-6}$ alkyl C(O)$R^b$, OC(O) $C_{1-6}$ alkyloxy, $OR^aC(O)OR^b$—$C_{1-6}$ alkylOC(O)O $C_{1-6}$ alkyloxy, —$SO_3H$, —$S(O)_pR^6$, —$S(O)_2NR^7R^8 C_{1-6}$alkylthio or nitro;
$R^6$ is selected from the group consisting of hydrogen, —$(CR^aR^b)_mOR^6$, halogen, $C_{1-6}$ haloalkyl, —$(CR^aR^b)_m$C(O)$R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl;

wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —C(O)$OR^1$, $OR^5$, —OC(O)$R^6$, —$(CR^aR^b)_mC(O)NR^7R^8$, —$NR^6C(O)R^6$, —$SR^6$, —$S(O)_pR^6$, —$S(O)_2NR^7R^8$, or —$NR^6S(O)_2R^6$;
$R^5$, $R^7$, and $R^8$ are independently selected from the group consisting of hydrogen, —$(CR^aR^b)_mOR^6$, $C_{1-6}$ haloalkyl, —$(CR^aR^b)_mC(O)R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or
$R^7$ and $R^8$ can be taken together to form a monocyclic or a bicyclic saturated or partially unsaturated carbocyclyl or heterocyclyl ring optionally having 1-5 heteroatoms selected from O, N or S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, —$(CR^aR^b)_mOR^6$, —$SR^6$, —$(CR^aR^b)_mNR^7R^8$, oxo, $C_{1-6}$ alkylsulfonyl, —$(CR^aR^b)_mCOOR^6$, —$(CR^aR^b)_mC(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$, and $C_{5-10}$ heteroaryl are optionally substituted with $C_{1-6}$ alkyl;
$R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl or
$R^a$, and $R^b$ can be taken together to form a monocyclic or a bicyclic ring saturated or partially unsaturated optionally having 1-5 heteroatoms selected from O, N or S;
m is 0 to 4;
n is 1 to 3;
p is 0-2.

2. The compounds of Formula (I) their tautomers, stereoisomers, and pharmaceutically acceptable salts thereof, as claimed in claim 1, wherein
A is substituted or unsubstituted 5-10 membered bicyclic or polycyclic unsaturated or partially unsaturated heterocyclic ring having 1-5 heteroatom independently selected from O, N or S;
D is selected from $CR^1$ or N;
G is selected from —C(O)$OR^1$, —C(O)$NR^aR^b$, —$NR^1SO_2R^1$ or 5 membered monocyclic fully or partially unsaturated heterocyclic ring having 1-4 heteroatoms independently selected from O, N, or S;
$R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl;
$R^2$, $R^3$, and $R^4$ are independently selected from hydrogen, $C_{1-6}$ alkyl, $C_{3-6}$ cycloalkyl, $C_{1-6}$ alkoxy, C(O)$R^1$, $R^1$C(O)$NR^aR^b$, —OC(O)$R^1$, $R^6$, —$(CR^aR^b)_mC(O)R^6$, —$(CR^aR^b)_mNR^7R^8$, —$NR^aC(O)$—, —$C_{1-6}$ alkoxy C(O)$NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, OC(O) $C_{1-6}$ alkyloxy, $OR^aC(O)OR^b$—$C_{1-6}$ alkylOC(O)O $C_{1-6}$ alkyloxy, or nitro;
$R^6$ is selected from the group consisting of hydrogen, —$(CR^aR^b)_mOR^6$, halogen, $C_{1-6}$ haloalkyl, —$(CR^aR^b)_m$C(O)$R^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, or $C_{5-10}$ heterocyclyl, wherein $C_{6-10}$ aryl, $C_{5-10}$ heteroaryl, $C_{3-6}$ cycloalkyl, $C_{5-10}$ heterocyclyl are optionally substituted with $C_{1-6}$ alkyl;

wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$, or —NR$^6$S(O)$_2$R$^6$;

R$^5$, R$^7$, and R$^8$ are independently selected from the group consisting of hydrogen, —(CR$^a$R$^b$)$_m$OR$^6$, $C_{1-6}$ haloalkyl, —(CR$^a$R$^b$)$_m$C(O)R$^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or R$^7$ and R$^8$ can be taken together to form a monocyclic or a bicyclic saturated or partially unsaturated carbocyclyl or heterocyclyl ring optionally having 1-5 heteroatoms selected from O, N or S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, —(CR$^a$R$^b$)$_m$OR$^6$, —SR$^6$, —(CR$^a$R$^b$)$_m$NR$^7$R$^8$, oxo, $C_{1-6}$ alkylsulfonyl, —(CR$^a$R$^b$)$_m$COOR$^6$, —(CR$^a$R$^b$)$_m$C(O)NR$^7$R$^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl;

R$^a$, and R$^b$ are independently selected from the group consisting of hydrogen, —OR$^6$, halogen, $C_{1-6}$ haloalkyl, perhalo $C_{1-6}$ alkyl, —SO$_p$R$^1$, and $C_{1-6}$ alkyl or R$^a$, and R$^b$ can be taken together to form a monocyclic or a bicyclic ring saturated or partially unsaturated optionally having 1-5 heteroatoms selected from O, N or S;

m is 0 to 4;

n is 1 to 3;

p is 0-2.

3. The compounds of Formula (I) their tautomers, stereoisomers, and pharmaceutically acceptable salts thereof, as claimed in claim 1, wherein A is substituted or unsubstituted 5-10 membered bicyclic or polycyclic unsaturated or partially unsaturated heterocyclic ring having 1-5 heteroatom independently selected from O, N or S;

D is selected from CR$^1$ or N;

G is selected from —C(O)OR$^1$, —C(O)NR$^a$R$^b$, —NR$^1$SO$_2$R$^1$ or 5 membered monocyclic fully unsaturated or partially unsaturated heterocyclic ring having 1-4 heteroatom independently selected from O, N, or S;

R$^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl;

R$^2$, R$^2$, and R$^4$ are independently selected from hydrogen, $C_{1-6}$ alkyl, $C_{3-6}$ cycloalkyl, $C_{1-6}$ alkoxy, C(O)R$^1$, R$^1$C(O)NH$_2$, —OC(O)R$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy C(O)NR$^a$R$^b$, —NR$^a$C(O)NR$^a$R$^b$, NR$^a$OH, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, OC(O) $C_{1-6}$ alkyloxy, OR$^a$C(O)OR$^b$—$C_{1-6}$ alkylOC(O)O $C_{1-6}$ alkyloxy, or nitro;

R$^6$ is selected from the group consisting of hydrogen, —(CR$^a$R$^b$)$_m$OR$^6$, halogen, $C_{1-6}$ haloalkyl, —(CR$^a$R$^b$)$_m$C(O)R$^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl;

wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —C(O)OR$^1$, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

R$^5$, R$^7$, and R$^8$ are independently selected from the group consisting of hydrogen, —(CR$^a$R$^b$)$_m$OR$^6$, $C_{1-6}$ haloalkyl, —(CR$^a$R$^b$)$_m$C(O)R$^6$, $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, $C_{5-10}$ heterocyclyl, wherein, $C_{6-10}$ aryl, $C_{5-10}$ heteroaryl, $C_{3-6}$ cycloalkyl, and $C_{5-10}$ heterocyclyl are optionally substituted with $C_{1-6}$ alkyl or R$^7$ and R$^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halogen, $C_{1-6}$ alkyl, $C_{2-6}$ alkenyl, $C_{2-6}$ alkynyl, nitro, cyano, —(CR$^a$R$^b$)$_m$OR$^6$, —SR$^6$, —(CR$^a$R$^b$)$_m$NR$^7$R$^8$, oxo, $C_{1-6}$ alkylsulfonyl, —(CR$^a$R$^b$)$_m$COOR$^6$, —(CR$^a$R$^b$)$_m$C(O)NR$^7$R$^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl;

R$^a$, and R$^b$ are independently selected from the group consisting of hydrogen, —OR$^6$, halogen, $C_{1-6}$ haloalkyl, perhalo $C_{1-6}$ alkyl, —SO$_p$R$^1$, and $C_{1-6}$ alkyl or R$^a$, and R$^b$ can be taken together to form a monocyclic or a bicyclic ring saturated or partially unsaturated optionally having 1-5 heteroatoms selected from O, N, or S;

m is 0 to 4;

n is 1 to 3;

p is 0-2.

4. The compounds of Formula (I) their tautomers, stereoisomers, and pharmaceutically acceptable salts thereof, as claimed in claim 1, wherein A is substituted or unsubstituted 5-10 membered bicyclic or polycyclic unsaturated or partially unsaturated heterocyclic ring having 1-5 heteroatom independently selected from O, N or S;

D is selected from CR$^1$ or N;

G is selected from —C(O)OR$^1$, —C(O)NR$^a$R$^b$, —NR$^1$SO$_2$R$^1$ or 5 membered monocyclic fully unsaturated or partially unsaturated heterocyclic ring having 1-4 heteroatom independently selected from O, N, or S;

R$^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl;

R$^2$, R$^2$, and R$^4$ are independently selected from hydrogen, $C_{1-6}$ alkyl, $C_{3-6}$ cycloalkyl, $C_{1-6}$ alkoxy, C(O)R$^1$, R$^1$C(O)NH$_2$, —OC(O)R$^1$, R$^6$, —(CR$^a$R$^b$)$_m$C(O)R$^6$, —(CR$^a$R$^b$)$_m$NR$^7$R$^8$, —NR$^a$C(O)—, —C$_{1-6}$ alkoxy $C(O)NR^aR^b$, $—NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $OC(O)$ $C_{1-6}$ alkyloxy, $OR^aC(O)OR^b$—$C_{1-6}$ alkylOC(O) $OC_{1-6}$ alkyloxy, or nitro;

$R^6$ is selected from the group consisting of hydrogen, $—(CR^aR^b)_mOR^6$, halogen, $C_{1-6}$ haloalkyl, $—(CR^aR^b)_m$ $C(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl;

wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, $—C(O)OR^1$, $OR^5$, $—OC(O)R^6$, $—(CR^aR^b)_mC(O)NR^7R^8$, $—NR^6C(O)R^6$, $—SR^6$, $—S(O)_pR^6$, $—S(O)_2NR^7R^8$, or $—NR^6S(O)_2R^6$;

$R^5$, $R^7$, and $R^8$ are independently selected from the group consisting of hydrogen, $—(CR^aR^b)_mOR^6$, $C_{1-4}$ haloalkyl, $—(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl or $R^7$ and $R^8$ can be taken together to form a monocyclic or a bicyclic saturated or partially unsaturated carbocyclyl or heterocyclyl ring optionally having 1-5 heteroatoms selected from O, N, or S, wherein the monocyclic or a bicyclic ring carbocyclyl or heterocyclyl is further optionally substituted with 1 to 4 substituents independently selected from halo, $C_{1-6}$ alkyl, $C_{2-6}$ alkenyl, $C_{2-6}$ alkynyl, nitro, cyano, $—(CR^aR^b)_mOR^6$, $—SR^6$, $—(CR^aR^b)_mNR^7R^8$, oxo, $C_{1-6}$ alkylsulfonyl, $—(CR^aR^b)_mCOOR^6$, $—(CR^aR^b)_mC(O)NR^7R^8$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl;

$R^a$, and $R^b$ are independently selected from the group consisting of hydrogen, $—OR^6$, halogen, $C_{1-6}$ haloalkyl, perhalo $C_{1-6}$ alkyl, $—SO_pR^1$, and $C_{1-6}$ alkyl or $R^a$, and $R^b$ can be taken together to form a monocyclic or a bicyclic ring saturated or partially unsaturated optionally having 1-5 heteroatoms selected from O, N or S;

m is 0 to 4;

n is 1 to 3;

p is 0-2.

5. The compounds of Formula (I) their tautomers, stereoisomers, and pharmaceutically acceptable salts thereof, as claimed in claim 1, wherein A is substituted or unsubstituted $C_{5-10}$ bicyclic or polycyclic unsaturated or partially unsaturated heterocyclic ring having 1-5 heteroatom independently selected from O, N or S;

D is selected from $CR^1$ or N;

G is selected from $—C(O)OR^1$, $—C(O)NR^aR^b$, $—NR^1SO_2R^1$ or 5 membered monocyclic fully unsaturated or partially unsaturated heterocyclic ring having 1-4 heteroatom independently selected from O, N, or S;

$R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl;

$R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NH_2$, $—OC(O)R^1$, $R^6$, $—(CR^aR^b)_mC(O)R^6$, $—(CR^aR^b)_mNR^7R^8$, $—NR^aC(O)—$, $—C_{1-6}$ alkoxy $C(O)NR^aR^b$, $—NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $OC(O)$ $C_{1-6}$ alkyloxy, $OR^aC(O)OR^b$—$C_{1-6}$ alkylOC(O) $OC_{1-6}$ alkyloxy, or nitro;

$R^6$ is selected from the group consisting of hydrogen, $—(CR^aR^b)_mOR^6$, halogen, $C_{1-6}$ haloalkyl, $—(CR^aR^b)_m$ $C(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl;

wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, $—C(O)OR^1$, $OR^5$, $—OC(O)R^6$, $—(CR^aR^b)_mC(O)NR^7R^8$, $—NR^6C(O)R^6$, $—SR^6$, $—S(O)_pR^6$, $—S(O)_2NR^7R^8$ or $—NR^6S(O)_2R^6$;

$R^5$, $R^7$, and $R^8$ are independently selected from the group consisting of hydrogen, $—(CR^aR^b)_mOR^6$, $C_1$-4 haloalkyl, $—(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl; or $R^7$ and $R^8$ can be taken together to form a monocyclic or a bicyclic saturated or partially unsaturated carbocyclyl or heterocyclyl ring optionally having 1-4 heteroatoms selected from O, N, or S, wherein the monocyclic or a bicyclic ring carbocyclyl or heterocyclyl is further optionally substituted with 1 to 4 substituents independently selected from halo, $C_{1-6}$ alkyl, cyano, $—(CR^aR^b)_mOR^6$, $—SR^6$, oxo, $—(CR^aR^b)_mCOOR^6$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl;

$R^a$, and $R^b$ are independently selected from the group consisting of hydrogen, $—OR^6$, halogen, $C_{1-6}$ haloalkyl, perhalo $c_{1-6}$ alkyl, $—SO_p^1$, and $C_{1-6}$ alkyl; or $R^a$, and $R^b$ can be taken together to form a monocyclic or a bicyclic ring saturated or partially unsaturated optionally having 1-5 heteroatoms selected from O, N, or S;

m is 0 to 4;

n is 1 to 3;

p is 0-2.

6. The compounds of Formula (I) their tautomers, stereoisomers, and pharmaceutically acceptable salts thereof, as claimed in claim 1, wherein A is substituted or unsubstituted 5-10 membered bicyclic or polycyclic unsaturated or partially unsaturated heterocyclic ring having 1-5 heteroatom independently selected from O, N, or S;

D is selected from $CR^1$ or N;

G is selected from $—C(O)OR^1$, $—C(O)NR^aR^b$, $—NR^1SO_2R^1$ or 5 membered monocyclic fully unsaturated or partially unsaturated heterocyclic ring having 1-4 heteroatom independently selected from O, N, or S;

$R^1$ is selected from hydrogen, $C_{1-6}$ haloalkyl, $C_{1-6}$ alkyl, $C_{5-10}$ heteroaryl, or $C_{3-6}$ cycloalkyl, wherein $C_{3-6}$ cycloalkyl, and $C_{5-10}$ heteroaryl are optionally substituted with $C_{1-6}$ alkyl;

$R^2$, $R^3$, and $R^4$ are independently selected from hydrogen, $C_{1-6}$ alkyl, $C_{3-6}$ cycloalkyl, $C_{1-6}$ alkoxy, $C(O)R^1$, $R^1C(O)NH_2$, —$OC(O)R^1$, $R^6$, —$(CR^aR^b)_mC(O)R^6$, —$(CR^aR^b)_mNR^7R^8$, —$NR^aC(O)$—, —$C_{1-6}$ alkoxy $C(O)NR^aR^b$, —$NR^aC(O)NR^aR^b$, $NR^aOH$, $C_{1-6}$ alkoxyamino, azido, cyano, halogen, hydroxy, $C_{1-6}$ alkyl hydroxy, $C_{1-6}$ haloalkyl, perhalo $C_{1-6}$ alkyl, $OC(O)$ $C_{1-6}$ alkyloxy, $OR^aC(O)OR^b$—$C_{1-6}$ alkylOC(O) $OC_{1-6}$ alkyloxy, or nitro;

$R^6$ is selected from the group consisting of hydrogen, —$(CR^aR^b)_mOR^6$, halogen, $C_{1-6}$ haloalkyl, —$(CR^aR^b)mC(O)R^6$, $C_{1-6}$ alkyl, $C_{5-10}$ heteroaryl, $C_{3-6}$ cycloalkyl, or $C_{5-10}$ heterocyclyl, wherein $C_{5-10}$ heteroaryl, $C_{3-6}$ cycloalkyl, $C_{5-10}$ heterocyclyl are optionally substituted with $C_{1-6}$ alkyl;

wherein $C_{1-6}$ alkyl, $C_{2-6}$ alkenyl, $C_{2-6}$ alkynyl, $C_{6-10}$ aryl, $C_{5-10}$ heteroaryl, $C_{3-6}$ cycloalkyl, and $C_{5-10}$ heterocyclyl are optionally substituted with one or more substituents selected from hydroxy, $C_{1-6}$ alkyl, $C_{1-6}$ alkoxy, $C_{1-6}$ alkoxyalkyl, halogen, $C_{1-6}$ haloalkyl, perhalo-$C_{1-6}$ alkyl, cyano, -cyano $C_{1-6}$ alkyl-, amino, —$C(O)OR^1$, $OR^5$, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$, or —$NR^6S(O)_2R^6$;

$R^5$, $R^7$, and $R^8$ are independently selected from the group consisting of hydrogen, —$(CR^aR^b)_mOR^6$, $C_1$-4 haloalkyl, —$(CR^aR^b)_mC(O)R^6$, $C_{1-4}$ alkyl, $C_{2-4}$ alkenyl, $C_{2-4}$ alkynyl, $C_{6-8}$ aryl, 5-7 membered heteroaryl, $C_{3-5}$ cycloalkyl, 5-7 membered heterocyclyl, wherein, $C_{6-8}$ aryl, 5-7 membered heteroaryl, $C_{3-5}$ cycloalkyl, and 5-7 membered heterocyclyl are optionally substituted with $C_{1-6}$ alkyl; or $R^7$ and $R^8$ can be taken together to form a monocyclic or a bicyclic saturated or partially unsaturated carbocyclyl or heterocyclyl ring optionally having 1-4 heteroatoms selected from O, N, or S, wherein the monocyclic or a bicyclic ring carbocyclyl or heterocyclyl is further optionally substituted with 1 to 4 substituents independently selected from halo, $C_{1-6}$ alkyl, cyano, —$(CR^aR^b)_mOR^6$, —$SR^6$, oxo, —$(CR^aR^b)_mCOOR^6$, $C_{3-6}$ cycloalkyl, $C_{6-10}$ aryl, $C_{5-10}$ heterocyclyl, or $C_{5-10}$ heteroaryl, wherein $C_{3-6}$ cycloalkyl, $C_{6-10}$ aryl, $C_{5-10}$ heterocyclyl, and $C_{5-10}$ heteroaryl are optionally substituted with $C_{1-6}$ alkyl;

$R^a$, and $R^b$ are independently selected from the group consisting of hydrogen, —$OR^6$, halogen, $C_{1-6}$ haloalkyl, perhalo $C_{1-6}$ alkyl, —$SO_pR^1$, and $C_{1-6}$ alkyl; or m is 0 to 3;

n is 1 to 3;

p is 0-2.

7. The compound of Formula (I) as claimed in claim 1, tautomers, stereoisomers, and pharmaceutically acceptable salts thereof, which is selected from a group consisting of:

2-[3-[4-(8-isoquinolyloxy)-2-(trifluoromethyl)phenoxy] phenyl]acetic acid (A1),

2-[3-[4-phthalazin-5-yloxy-2-(trifluoromethyl)phenoxy] phenyl]acetic acid (A2),

3-[3-[4-phthalazin-5-yloxy-2-(trifluoromethyl)phenoxy] phenyl]propanoic acid (A3), 2-[3-[4-(8-chlorophthalazin-5-yl)oxy-2-(trifluoromethyl) phenoxy]phenyl]acetic acid (A4), 2-[3-[4-(1-methylindazol-7-yl)oxy-2-(trifluoromethyl) phenoxy]phenyl]acetic acid (A5), 2-[3-[4-(6-quinolyloxy)-2-(trifluoromethyl)phenoxy]phenyl]acetic acid (A6), 3-[3-[4-imidazo[1,2-a]pyridin-8-yloxy-2-(trifluoromethyl)phenoxy]phenyl]propanoic acid (A7), 2-[3-[4-[(5-fluoro-8-isoquinolyl)oxy-2-(trifluoromethyl) phenoxy]phenyl]acetic acid (A8), 2-[3-[4-quinazolin-5-yloxy-2-(trifluoromethyl)phenoxy] phenyl]acetic acid (A9), 3-[3-[4-[(2-methyl-3,4-dihydro-1H-isoquinolin-8-yl) oxy]-2-(trifluoromethyl) phenoxy] phenyl]propanoic acid (A10), 3-[3-[4-(2,3-dihydro-1,4-benzodioxin-5-yloxy)-2-(trifluoromethyl)phenoxy]phenyl]propanoic acid (A11), 3-[3-[4-(8-quinolyloxy)-2-(trifluoromethyl)phenoxy]phenyl]propanoic acid (A12), 3-[3-[4-(4-quinolyloxy)-2-(trifluoromethyl)phenoxy]phenyl]propanoic acid (A13), 3-[3-[4-(5-isoquinolyloxy)-2-(trifluoromethyl)phenoxy] phenyl]propanoic acid (A14), 2-[3-[4-(2-methylindazol-4-yl)oxy-2-(trifluoromethyl) phenoxy]phenyl]acetic acid (A15), 2-[3-[4-(1-methylindazol-4-yl)oxy-2-(trifluoromethyl) phenoxy]phenyl]acetic acid (A16), 2-[3-[4-([1,2,4]triazolo[4,3-a]pyridin-5-yloxy)-2-(trifluoromethyl)phenoxy]phenyl]acetic acid (A17), 2-[3-[4-(3,4-dihydro-2H-1,4-benzoxazin-6-yloxy)-2-(trifluoromethyl)phenoxy]phenyl]acetic acid (A18), 2-[3-[4-([1,2,4]triazolo [4,3-a]pyridin-7-yloxy)-2-(trifluoromethyl)phenoxy] phenyl] acetic acid (A19), 2-[3-[4-[1-(oxetan-3-yl)indol-6-yl]oxy-2-(trifluoromethyl)phenoxy]phenyl]acetic acid (A20), 2-[3-[4-[1-(oxetan-3-yl)indazol-6-yl]oxy-2-(trifluoromethyl)phenoxy]phenyl]acetic acid (A21), 2-[3-[4-[2-(oxetan-3-yl)indazol-6-yl]oxy-2-(trifluoromethyl)phenoxy]phenyl]acetic acid (A22), 2-[3-[4-[1-(oxetan-3-yl)indazol-5-yl]oxy-2-(trifluoromethyl)phenoxy]phenyl]acetic acid (A23), 2-[3-[4-[2-(oxetan-3-yl)indazol-5-yl]oxy-2-(trifluoromethyl)phenoxy]phenyl]acetic acid (A24), 2-[3-[4-[3-(oxetan-3-yl)benzotriazol-5-yl]oxy-2-(trifluoromethyl) phenoxy]phenyl]acetic acid (A25), 2-[3-[4-[3-(oxetan-3-yl)benzimidazol-5-yl]oxy-2-(trifluoromethyl)phenoxy] phenyl]acetic acid (A26), 2-[3-[4-[2-methyl-3-(oxetan-3-yl)benzimidazol-5-yl] oxy-2-(trifluoromethyl) phenoxy] phenyl]acetic acid (A27), 2-[3-[2-(difluoromethyl)-4-[2-methyl-3-(oxetan-3-yl) benzimidazol-5-yl]oxy-phenoxy] phenyl]acetic acid (A28), 2-[3-[4-[1-(oxetan-3-yl)imidazo[4,5-b]pyridin-6-yl]oxy-2-(trifluoromethyl) phenoxy] phenyl]acetic acid (A29), 2-[3-[4-[1-(oxetan-3-yl)pyrrolo[2,3-b]pyridin-6-yl]oxy-2-(trifluoromethyl) phenoxy] phenyl]acetic acid (A30), 6-[4-[3-(carboxymethyl)phenoxy]-3-(trifluoromethyl) phenoxy]imidazo[1,5-a]pyridine-3-carboxylic acid (A31), 2-[3-[4-[1-(carboxymethyl)indol-5-yl]oxy-2-(trifluoromethyl)phenoxy]phenyl]acetic acid (A32), 2-[3-[4-[1-(carboxymethyl)indol-6-yl]oxy-2-(trifluoromethyl)phenoxy]phenyl]acetic acid (A33), 3-[4-[4-(8-isoquinolyloxy)-2-(trifluoromethyl)phenoxy] phenyl]propanoic acid (A34), 3-[3-[4-(2-methylindazol-5-yl)oxy-2-(trifluoromethyl) phenoxy]phenyl]propanoic acid (A35), 2-[3-[[5-(8-isoquinolyloxy)-3-(trifluoromethyl)-2-pyridyl]oxy]phenyl]acetic acid (A36), 3-[3-[4-imidazo[1,2-a]pyridin-5-yloxy-2-(trifluoromethyl)phenoxy]phenyl]propanoic acid (A37),
2-[3-[2-cyclopropyl-4-(8-isoquinolyloxy)phenoxy]phenyl]acetic acid (A38),
2-[3-[2-cyclopropyl-4-[2-methyl-3-(oxetan-3-yl)benzimidazol-5-yl]oxy-phenoxy] phenyl]acetic acid (A39),
2-[3-[4-[(1-chloro-8-isoquinolyl)oxy]-2-(trifluoromethyl)phenoxy]phenyl]acetic acid (A40),
2-[3-[4-[(1-methyl-8-isoquinolyl)oxy]-2-(trifluoromethyl)phenoxy]phenyl]acetic acid (A41),
3-[3-[4-(8-isoquinolyloxy)-2-(trifluoromethyl)phenoxy]phenyl]propanoic acid (A42),
3-[3-[4-(1,2,3,4-tetrahydroisoquinolin-8-yloxy)-2-(trifluoromethyl) phenoxy] phenyl] propanoic acid (A43),
3-[3-[4-indan-1-yloxy-2-(trifluoromethyl)phenoxy]phenyl]propanoic acid (A44),
3-[3-[4-(1H-indazol-5-yloxy)-2-(trifluoromethyl)phenoxy]phenyl]propanoic acid (A45),
2-[3-[4-[(3-cyano-1H-indazol-5-yl)oxy]-2-(trifluoromethyl) phenoxy]phenyl]acetic acid (A46),
5-[4-[3-(carboxymethyl)phenoxy]-3-(trifluoromethyl)phenoxy]-1H-indazole-3-carboxylic acid (A47),
2-[3-[4-(1H-indazol-4-yloxy)-2-(trifluoromethyl)phenoxy]phenyl]acetic acid (A48),
2-[3-[4-imidazo[1,5-a]pyridin-5-yloxy-2-(trifluoromethyl)phenoxy]phenyl]acetic acid (B1),
2-[3-[4-imidazo[1,5-a]pyridin-8-yloxy-2-(trifluoromethyl) phenoxy]phenyl]acetic acid (B2),
2-[3-[4-(3-methylimidazo[1,5-a]pyridin-5-yl)oxy-2-(trifluoromethyl)phenoxy]phenyl]acetic acid (B3),
2-[3-[4-(3-methylimidazo[1,5-a]pyridin-8-yl)oxy-2-(trifluoromethyl)phenoxy]phenyl]acetic acid (B4),
2-[3-[4-[3-(oxetan-3-yl)imidazo[1,5-a]pyridin-6-yl]oxy-2-(trifluoromethyl) phenoxy] phenyl] acetic acid (B5),
2-[3-[4-(8-isoquinolyloxy)-2-(trifluoromethyl)phenoxy]phenyl]-N-methylsulfonyl-acetamide (C1),
3-[3-[4-(8-isoquinolyloxy)-2-(trifluoromethyl)phenoxy]phenyl]propanamide (C2),
2-[3-[4-(8-isoquinolyloxy)-2-(trifluoromethyl)phenoxy]phenyl]acetamide (C3),
8-[4-[3-[2-(4H-1,2,4-triazol-3-yl)ethyl]phenoxy]-3-(trifluoromethyl)phenoxy]isoquinoline (D1),
8-[4-[3-[2-(1H-tetrazol-5-yl)ethyl]phenoxy]-3-(trifluoromethyl)phenoxy]isoquinoline (D2),
8-[4-[3-(1H-tetrazol-5-ylmethyl)phenoxy]-3-(trifluoromethyl) phenoxy]isoquinoline (D3), and
2-[3-[4-(8-isoquinolyloxy)-3-(trifluoromethyl)phenoxy]phenyl]acetic acid (E1).

8. A pharmaceutical composition comprising a compound of Formula (I), their tautomers, stereoisomers, or a pharmaceutically acceptable salt thereof as claimed in claim 1 together with a pharmaceutically acceptable carrier, optionally in combination with one or more other pharmaceutical compositions.

9. The pharmaceutical composition as claimed in claim 8, wherein the composition is in the form of a tablet, capsule, powder, syrup, solution, aerosol, or suspension.

10. A method for the treatment of neovascularization, macular degeneration, diabetic nephropathy, liver diseases, inflammation, cancer, metabolic diseases, cardiovascular disease, hypertension, non alcoholic steatohepetitis (NAASH), fatty liver disease (FLD), non alcoholic fatty liver disease (NAFLD), or retinal angiogenesis, said method comprising administering a combination of the compounds as claimed in claim 1, with other clinically relevant cytotoxic agents or non-cytotoxic agents to a subject in need thereof.

11. A method of treatment of as claimed in claim 10, wherein the other clinically relevant cytotoxic agents or non-cytotoxic agents are immune modulators.

\* \* \* \* \*